(12) United States Patent
Am Ende et al.

(10) Patent No.: US 6,641,840 B2
(45) Date of Patent: Nov. 4, 2003

(54) SUSTAINED RELEASE FORMULATIONS FOR GROWTH HORMONE SECRETAGOGUES

(75) Inventors: Mary T. Am Ende, Waterford, CT (US); William J. Curatolo, Niantic, CT (US); Scott M. Herbig, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/940,097

(22) Filed: Aug. 27, 2001

(65) Prior Publication Data

US 2002/0137765 A1 Sep. 26, 2002

Related U.S. Application Data

(60) Provisional application No. 60/229,074, filed on Aug. 30, 2000.

(51) Int. Cl.[7] .............................. A61K 9/28; A61K 9/20; A61K 9/48
(52) U.S. Cl. ...................... 424/474; 424/400; 424/451; 424/458; 424/464; 424/468
(58) Field of Search .................................. 424/473, 489, 424/464, 451, 457, 468, 474, 400; 514/303

(56) References Cited

U.S. PATENT DOCUMENTS

| | | | |
|---|---|---|---|
| 5,723,441 A | 3/1998 | Higley et al. | |
| 5,723,616 A | 3/1998 | Houghton et al. | |
| 5,773,441 A | 6/1998 | Hipskind et al. | |
| 5,840,331 A | 11/1998 | Van Cauter et al. | |
| 5,919,777 A | 7/1999 | Hansen et al. | |
| 5,945,412 A | 8/1999 | Fuh et al. | |
| 5,948,757 A | 9/1999 | Sommer et al. | |
| 6,107,306 A | 8/2000 | Carpino et al. | |
| 6,228,398 B1 * | 5/2001 | Devane et al. | 424/451 |

FOREIGN PATENT DOCUMENTS

| | | |
|---|---|---|
| WO | WO9413696 | 6/1994 |
| WO | WO9530422 | 11/1995 |
| WO | WO9724369 | 7/1997 |
| WO | WO9744042 | 11/1997 |
| WO | WO9748412 | 12/1997 |
| WO | WO9858947 | 12/1998 |
| WO | WO9901113 | 1/1999 |
| WO | WO9901120 | 1/1999 |
| WO | WO9901121 | 1/1999 |
| WO | WO9901122 | 1/1999 |
| WO | WO9924062 | 5/1999 |
| WO | WO9965486 | 12/1999 |
| WO | WO9965488 | 12/1999 |
| WO | WO0012047 | 9/2000 |

OTHER PUBLICATIONS

R. G. Clark, et al., *Intravenous growth hormone: growth responses to patterned infusions in hypophysectomized rats; Journal of Endocrinology*; (1985), p. 53–61.

R. G. Clark, et al., *Paradoxical growth–promoting effects induced by patterned infusions of somatostatin in female rats, Endocrinology*; (1988), p. 2675–2682.

Evelien F. Gevers, et al., *Growth, Growth Hormone (GH)–Binding Protein, and GH Receptors are Differentially Regulated by Peak and Trough Components of the GH Secretory Pattern in the Rat, Endocrinology*; (1996), p. 1013–1018.

Wendy C. Huhn, et al., *Twenty–four–hour Growth Hormone (GH)–releasing Peptide (GHRP) Infusion Enhances Pulsatile GH Secretion and Specifically Attenuates the Response to a Subsequent GHRP Bolus; Journal of Clinical Endocrinology and Metabolism*; (1993), p. 1202–1207.

Mark L. Hartman, et al., *Temporal structure of in vivo growth hormone secretory events in humans, The American Physiological Society*; (1991), p. E101–E110.

B. B. Bercu, et al., *Sex Differences in Growth Hormone (GH) Secretion by Rats Administered GH–Releasing Hexapeptide, Endocrinology*; (1991), p. 2592–2598.

R. G. Smith, et al., *Peptidomimetic Regulation of Growth Hormone Secretion, Endocrine Reviews*; (1997), p. 621–645.

G. Van Den Berghe, et al., *The Somatotropic Axis in Critical Illness: Effect of Continuous Growth Hormone (GH)–Releasing Hormone and GH–Releasing Peptide–2 Infusion, Journal of Clinical Endocrinology and Metabolism*; (1997), p. 590–599.

* cited by examiner

Primary Examiner—Thurman K. Page
Assistant Examiner—Robert M. Joynes
(74) Attorney, Agent, or Firm—Peter C. Richardson; Gregg C. Benson; John A. Wichtowski

(57) ABSTRACT

The present invention relates to formulations for administering a growth hormone secretagogue. More specifically, the present invention relates to sustained release formulations for administering a growth hormone secretagogue and formulations for administering a growth hormone secretagogue that provide for a part of the dose of the growth hormone secretagogue to be administered using an immediate release formulation and part of the dose of the growth hormone secretagogue to be administered using a sustained release formulation.

3 Claims, No Drawings

SUSTAINED RELEASE FORMULATIONS FOR GROWTH HORMONE SECRETAGOGUES

CROSS REFERENCE TO RELATED APPLICATION

This application claims priority of U.S. provisional patent application No. 60/229,074, filed Aug. 30, 2000, which is hereby incorporated by reference.

FIELD OF THE INVENTION

This invention relates to sustained release and combination formulations for growth hormone secretagogues.

BACKGROUND OF THE INVENTION

Growth hormone (GH), which is secreted by the pituitary gland, stimulates the growth of all tissues of the body that are capable of growing. In addition, growth hormone is known to have the following effects on metabolic processes:
1. increased rate of protein synthesis in substantially all cells;
2. decreased rate of carbohydrate metabolism in cells; and
3. increased mobilization of free fatty acids and use of fatty acids for energy.

A deficiency in GH production and/or secretion can result in various diseases or conditions, such as dwarfism, profound reduction in lean body mass and concomitant increase in total body fat, particularly in the truncal region, decreased skeletal and cardiac muscle mass and muscle strength that can result in significant decreases in exercise capacity, musculoskeletal frailty, which is typically associated with old age, congestive heart failure, insulin resistance, bone fracture, reduction in bone density, delayed wound healing, and osteoporosis. The administration of exogenous growth hormone has been shown to reverse the above-mentioned metabolic changes and has also been shown to lower plasma low density lipoprotein (LDL) cholesterol and improve psychological well being.

With the rapid worldwide growth of the population aged 65 years and over, aging-associated musculoskeletal frailty will become an increasing public health problem. Frailty, in addition to its personal impact on daily functioning and social interaction, is associated with major health consequences such as injurious falls, hip fractures, and nursing home admissions. Annually, in the United States, up to 10% of frail adults over age 74 experience an injurious fall.

The causes of the long term age-associated decline in muscle and bone mass, which after age 40 in both men and women averages 0.5–1% per year, are unknown. A decline in synthesis/secretion of endogenous anabolic hormones may contribute to age-associated changes in body composition, which are characterized by decreased muscle and bone mass and a relative increase in adiposity. For example, in both men and women, growth hormone (GH, also termed somatotropin) secretion declines by 50% between the ages of 30 and 70.

GH is naturally released by the body in a patterned manner with typically large pulses during sleep and subsequent smaller pulses of GH released later. It is also believed that growth hormone releasing hormone [GHRH, also known as growth hormone releasing factor (GRF)] is released from the hypothalamus in a pulsatile or patterned manner and consequently stimulates the release of GH in a correspondingly patterned manner.

In cases where increased levels of growth hormone are desired, the problem has generally been approached by providing exogenous growth hormone, typically by injection, or by administering a compound that stimulates the secretion of growth hormone. Typically, these compounds are peptidyl in nature and need to be administered by injection. As an alternative approach, compounds termed secretagogues have been developed that stimulate the release of endogenous growth hormone. See, for example, U.S. Pat. No. 5,723,616, WO 95/11029, WO 95/17422, WO 95/11697, and WO 94/13696.

Therapeutic intervention using the growth hormone-Insulin-like Growth Factor-I (IGF-1) system is a developing field, and evidence is accumulating that suggests that therapeutic efficacy for different indications may be optimally achieved by stimulation of GH or IGF-1 or both. For some indications such as osteoporosis, it is believed that secretion of endogenous growth hormone results in the subsequent release of IGF-I, and that IGF-I elicits therapeutic effects, e.g., increased bone density. Thus, it would be desirable to have a therapeutic formulation that stimulates the secretion of IGF-I in a patient, but minimally affects the secretion of growth hormone, particularly over time. Minimizing GH levels in this situation may avoid potential adverse sequelae of continuous GH stimulation such as in acromegaly. A formulation that can be orally administered once per day is preferred. Prior to the present invention, it was not known how to prepare a therapeutic formulation containing a growth hormone secretagogue that could be easily administered, and which stimulated the levels of endogenous IGF-I while minimally affecting the release of GH over time. With a sustained release dosage form, it has been found that with steady state treatment using a growth hormone secretagogue (i.e., after 2 or more weeks of treatment), growth hormone plasma concentration peaks will be higher than in the untreated patient (i.e., baseline), but lower than the growth hormone peaks would be during the first few days of treatment. Typically, IGF-1 would be higher at steady state than either baseline or after the first few days of treatment.

It may also be advantageous for some indications to have an orally administerable therapeutic formulation that provides for both a sustained endogenous release of IGF-I and a small but significant release of GH in order to elicit the effects of IGF-I and non-IGF-I mediated effects of GH. Finally, it may be advantageous in some indications such as improving muscle mass to elevate GH while minimally elevating IGF-1.

SUMMARY OF THE INVENTION

The present invention provides sustained release dosage forms for oral administration to a mammal, the dosage forms comprising a growth hormone secretagogue and a pharmaceutically acceptable carrier, which dosage forms result in a maximum growth hormone secretagogue plasma concentration, $C_{max}$, which is less than 80% of the $C_{max}$ that occurs when an equal dose of the growth hormone secretagogue is orally administered using an immediate release dosage form.

In a preferred embodiment, the sustained release dosage forms provide total blood growth hormone secretagogue exposure that is not proportionately decreased as much as $C_{max}$.

In another preferred embodiment of the sustained release dosage from, the dosage form is an osmotic tablet that comprises a core that is coated with an asymmetric membrane, the core comprising:
1) about 4 to about 10 mg of 2-amino-N-[2-(3a-(R)-benzyl-2-methyl-3-oxo-2,3,3a,4,6,7-hexahydro-pyrazolo[4,3-c]

pyridin-5-yl)-1-(R)-benzyloxymethyl-2-oxo-ethyl]-isobutyramide L-tartrate;
2) about 12 to about 50 wt % of the core of an acid selected from fumaric acid, tartaric acid, succinic acid, citric acid, L-aspartic acid, ascorbic acid, or combinations thereof;
3) about 20 to about 63 wt % of the core of an osmotic agent selected from mannitol, sorbitol, lactose, or combinations thereof;
4) about 22 to about 49 wt % of the core microcrysalline cellulose binder; and
5) about 0.5 to about 1.5 wt % of the core magnesium stearate, and the asymmetric membrane comprising cellulose acetate and polyethylene glycol which adds about 10 to about 18 wt % to the core for a core tablet having a weight of about 200 mg or less or about 8 to about 17 wt % to the core tablet for core tablets having a weight of about 300 mg.

In another preferred embodiment of the sustained release dosage forms, the growth hormone secretagogue exhibits an elimination half-life of less than about 6 hours.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyra L-tartrate; 2-amino-N-{1-(R)-(2,4-difluoro-benzyloxymethyl)-2-oxo-2-[3-oxo-3a-(R)-pyridin=2-ylmethyl-2-(2,2,2-trifluoro-ethyl)-2,3,3a,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

In another preferred embodiment of the sustained release dosage forms, the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, and which sustained release dosage forms release about 0.007 to about 0.010 mg/hr/kg for about a 4 mg dose; about 0.007 to about 0.014 mg/hr/kg for about a 6 mg dose; about 0.006 to about 0.019 mg/hr/kg for about an 8 mg dose; about 0.010 to about 0.029 mg/hr/kg for about a 12 mg dose; about 0.013 to about 0.038 mg/hr/kg for about a 16 mg dose; about 0.019 to about 0.057 mg/hr/kg for about a 24 mg dose; or about 0.038 to about 0.114 mg/hr/kg for about a 48 mg dose. (Mg/hr/kg means milligrams of active compound released per hour for each kg of the patient's weight.)

In another preferred embodiment of the sustained release dosage forms immediately above, the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In another preferred embodiment of the sustained release dosage forms, one or more excipients is selected from: ascorbic acid; L-aspartic acid; citric acid; fumaric acid; succinic acid; tartaric acid; sodium bitartrate; microcrystalline cellulose; microcrystalline cellulose, silicified; polyethylene glycol; calcium stearate; or magnesium stearate.

In another preferred embodiment of the sustained release dosage forms, the dosage forms are an osmotic tablet comprising an osmotic agent selected from lactose; mannitol; sodium bitartrate; or sorbitol.

The present invention also provides sustained-release dosage forms for oral administration to a mammal, the dosage forms comprising a growth hormone secretagogue and a pharmaceutically acceptable carrier, which dosage forms result in a growth hormone secretagogue plasma concentration that exceeds the minimum effective concentration for a time, $\Delta T_{T2-T1}$, which is greater than, by at least 30 minutes, the $\Delta T_{T2-T1}$ determined when an equal dose of the growth hormone secretagogue is orally administered using an immediate release dosage form, wherein $\Delta T_{T2-T1}$ is the time period for which the plasma concentration of the growth hormone secretagogue remains above the minimum effective concentration, with T1 being the time the plasma concentration first goes above the minimum effective concentration and T2 being the time when the plasma concentration goes below the minimum effective concentration.

In another preferred embodiment of the sustained release dosage forms, the growth hormone secretagogue exhibits an elimination half-life of less than 6 hours.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate; 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

In another preferred embodiment of the sustained release dosage forms, the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In another preferred embodiment of the sustained release dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, and which dosage forms release about 0.009 to about 0.021 mg/hr/kg for about a 6 mg dose; about 0.006 to about 0.029 mg/hr/kg for about an 8 mg dose; about 0.010 to about 0.043 mg/hr/kg for about a 12 mg dose; about 0.013 to about 0.057 mg/hr/kg for about a 16 mg dose; about 0.019 to about 0.086 mg/hr/kg for about a 24 mg dose; or about 0.034 to about 0.343 mg/hr/kg for about a 48 mg dose.

In another preferred embodiment of the sustained release dosage forms, the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In another preferred embodiment of the sustained release dosage forms, one or more excipients is selected from: ascorbic acid; L-aspartic acid; citric acid; fumaric acid; succinic acid; tartaric acid; sodium bitartrate; microcrystalline cellulose; microcrystalline cellulose, silicified; polyethylene glycol; calcium stearate; or magnesium stearate.

In another preferred embodiment of the sustained release dosage forms, the dosage forms are an osmotic tablet comprising an osmotic agent selected from lactose; mannitol; sodium bitartrate; or sorbitol.

Also provided by the present invention are combination dosage forms for oral administration of a growth hormone secretagogue to a mammal, the dosage forms comprising two portions: 1) a portion that immediately releases an amount of a growth hormone secretagogue; and 2) a portion that provides for sustained release of an amount of a growth hormone secretagogue, which dosage form results in a maximum growth hormone secretagogue plasma concentration, $C_{max}$, which is less than 80% of the $C_{max}$ that occurs when an equal dose of the growth hormone secretagogue is orally administered using an immediate release dosage form.

In a preferred embodiment, the combination dosage forms provide total blood growth hormone secretagogue exposure that is not proportionately decreased as much as $C_{max}$.

In a preferred embodiment of the combination dosage forms, the growth hormone secretagogue exhibits an elimination half-life of less than about 6 hours.

In a preferred embodiment of the combination dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate; 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

In a preferred embodiment of the combination dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

In a preferred embodiment of the combination dosage forms, the sustained release portion of the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

The present invention also provides combination dosage forms for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage forms comprising two portions: 1) a portion that immediately releases an amount of a growth hormone secretagogue; and 2) a portion that provides for sustained release of an amount of a growth hormone secretagogue, the dosage form having the following characteristics for each dose:

| Total Growth Hormone Secretagogue Dose (mg) | Immediate Release Portion (% of Total Growth Hormone Secretagogue Dose) | Sustained Release Portion (% of Total Growth Hormone Secretagogue Dose) | Time Period of Sustained Release (hours) |
| --- | --- | --- | --- |
| about 4 | about 5 to about 50 | about 95 to about 50 | about 4 to about 6 |
| about 4 | about 50 to about 75 | about 50 to about 25 | about 8 to about 10 |
| about 4 | about 75 | about 25 | about 12 to about 18 |
| about 6 | about 40 | about 60 | about 4 |
| about 6 | about 5 to about 40 | about 95 to about 60 | about 6 |
| about 6 | about 5 to about 75 | about 95 to about 25 | about 8 to about 12 |
| about 6 | about 40 to about 75 | about 60 to about 25 | about 14 to about 18 |
| about 12 | about 40 | about 60 | about 4 |
| about 12 | about 5 to about 40 | about 95 to about 60 | about 6 |
| about 12 | about 5 to about 62.5 | about 95 to about 37.5 | about 8 |
| about 12 | about 5 to about 75 | about 95 to about 25 | about 12 to about 18 |
| about 48 | about 5 to about 75 | about 95 to about 25 | about 16 |

In a preferred embodiment of the combination dosage forms, the sustained release portion of the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In a preferred embodiment of the combination dosage forms, the immediate release portion comprises a layer in a multilayer tablet; a coating on a sustained release tablet or multiparticulate; a compression coating on a sustained release tablet, or the immediate release portion can comprise multiparticulates along with sustained release multiparticulates.

In another preferred embodiment of the combination dosage forms, the sustained release portion comprises an osmotic tablet and the immediate release portion comprises a compression coating.

Also provided by the present invention are combination dosage forms for oral administration of a growth hormone secretagogue to a mammal, the dosage forms comprising two portions: 1) a portion that immediately releases an amount of a growth hormone secretagogue; and 2) a portion that provides for sustained release of an amount of a growth hormone secretagogue, which dosage form results in a growth hormone secretagogue plasma concentration that exceeds the minimum effective concentration for a time, $\Delta T_{T2-T1}$, which is greater than, by at least 30 minutes, the $\Delta T_{T2-T1}$ determined when an equal dose of the growth hormone secretagogue is orally administered using an immediate release dosage form, wherein $\Delta T_{T2-T1}$ is the time period for which the plasma concentration of the growth hormone secretagogue remains above the minimum effective concentration, with T1 being the time the plasma concentration first goes above the minimum effective concentration and T2 being the time when the plasma concentration goes below the minimum effective concentration.

In a preferred embodiment of the combination dosage forms, the growth hormone secretagogue exhibits an elimination half-life of less than 6 hours.

In a preferred embodiment of the combination dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate; 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

In another preferred embodiment of the combination dosage forms, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

In another preferred embodiment of the combination dosage forms, the sustained release portion of the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

Also provided are combination dosage forms for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage forms comprising two portions: 1) a portion that immediately releases an amount of a growth hormone secretagogue; and 2) a portion that provides for sustained release of an amount of a growth hormone secretagogue, the dosage forms having the following characteristics for each dose:

| Total Growth Hormone Secretagogue Dose (mg) | Immediate Release Portion (% of Total Growth Hormone Secretagogoue Dose) | Sustained Release Portion (% of the Total Growth Hormone Secretagogue Dose) | Time Period of Sustained Release (hours) |
|---|---|---|---|
| about 6 | about 5 to about 40 | about 95 to about 60 | about 4 |
| about 6 | about 5 to about 75 | about 95 to about 25 | about 6 |
| about 6 | about 5 to about 62.5 | about 95 to about 37.5 | about 8 |
| about 6 | about 5 to about 40 | about 95 to about 60 | about 10 |
| about 12 | about 5 to about 40 | about 95 to about 60 | about 4 |
| about 12 | about 5 to about 75 | about 95 to about 25 | about 6 to about 16 |
| about 12 | about 5 to about 40 | about 95 to about 60 | about 18 |
| about 48 | about 5 to about 75 | about 95 to about 25 | about 16 |

In a preferred embodiment of the combination dosage forms, the sustained release portion of the dosage forms comprise a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In a preferred embodiment of the combination dosage forms, the immediate release portion comprises a layer in a multilayer tablet; a coating on a sustained release tablet or multiparticulate; a compression coating on a sustained release tablet, or the immediate release portion can comprise multiparticulates along with sustained release multiparticulates.

In a preferred embodiment of the combination dosage forms, the sustained release portion comprises an osmotic tablet and the immediate release portion comprises a compression coating.

Also provided by the present invention are sustained release dosage forms comprising 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and a pharmaceutically acceptable carrier, which dosage forms, when tested in a USP-2 apparatus containing 500–900 ml of 0.1N HCl or simulated gastric fluid without enzyme release about 0.50 to about 0.67 mg/hr for about a 4 mg dose; about 0.50 to about 1.00 mg/hr for about a 6 mg dose; about 0.44 to about 1.33 mg/hr for about an 8 mg dose, about 0.67 to about 2.00 mg/hr for about a 12 mg dose; about 0.89 to about 2.67 mg/hr for about a 16 mg dose; about 1.33 to about 4.00 mg/hr for about a 24 mg dose; and about 2.67 to about 8.00 mg/hr for about a 48 mg dose.

Also provided by the present invention are sustained release dosage forms comprising 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and a pharmaceutically acceptable carrier, which dosage forms, when tested in a USP-2 apparatus containing 500–900 ml of 0.1N HCl or simulated gastric fluid without enzyme release about 0.60 to about 1.50 mg/hr for about a 6 mg dose, about 0.44 to about 2.00 mg/hr for about an 8 mg dose, about 0.67 to about 3.00 mg/hr for about a 12 mg dose, about 0.89 to about 4.00 mg/hr for about a 16 mg dose, about 1.33 to about 6.00 mg/hr for about a 24 mg dose, and about 2.40 to about 24.00 mg/hr for about a 48 mg dose.

Also provided by the present invention are combination dosage forms for orally administering 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage forms comprising two portions: 1) a portion that immediately releases an amount of a growth hormone secretagogue; and 2) a portion that provides for sustained release of an amount of a growth hormone secretagogue, which dosage form, when tested in a USP-2 apparatus containing 500–900 ml of 0.1N HCl or simulated gastric fluid without enzyme immediately releases about 5 to about 50% of the growth hormone secretagogue immediately and the rest over about 4 to about 6 hours for about a 4 mg total dose; immediately releases about 50 to about 75% and the rest over about 8 to about 10 hours for about a 4 mg total dose; immediately releases about 75% and the rest over about 12 to about 18 hours for about a 4 mg total dose; immediately releases about 40% and the rest over about 4 hours for about a 6 mg total dose; immediately releases about 5 to about 40% and the rest over about 6 hours for about a 6 mg total dose; immediately releases about 5 to about 75% and the rest over about 8 to about 12 hours for about a 6 mg total dose; immediately releases about 40 to about 75% and the rest over about 14 to about 18 hours for about a 6 mg total dose; immediately releases about 40% and the rest over about 4 hours for about a 12 mg total dose; immediately releases about 5 to about 40% and the rest over about 6 hours for about a 12 mg total dose; immediately releases about 5 to about 62.5% and the rest over about 8 hours for about a 12 mg total dose; immediately releases about 5 to about 75% and the rest over about 12 to about 18 hours for about a 12 mg total dose; or immediately releases about 5 to about 75% and the rest over about 16 hours for about a 48 mg total dose.

In a preferred embodiment of the combination dosage forms, the sustained release portion of the dosage forms comprises a matrix tablet that remains substantially intact during the period of sustained release; a disintegrating matrix tablet; a matrix tablet partially coated with a polymer that impedes the release of the growth hormone secretagogue; an osmotic tablet; a membrane-coated swelling-core tablet; a multiparticulate; or combinations thereof.

In another preferred embodiment of the combination dosage forms the immediate release portion comprises a layer in a multilayer tablet; a coating on a sustained release tablet or multiparticulate; a compression coating on a sustained release tablet, or the immediate release portion can comprise multiparticulates along with sustained release multiparticulates.

In another preferred embodiment of the combination dosage forms, the sustained release portion comprises an osmotic tablet and the immediate release portion comprises a compression coating.

Also provided are methods of increasing the plasma concentration of IGF-1 while minimally affecting the plasma concentration of growth hormone, the methods comprising administering to a mammal in need of increased plasma concentrations of IGF-1 a therapeutically effective amount of a growth hormone secretagogue using a sustained release formulation or a combination of a sustained release and immediate release dosage form.

In a preferred embodiment of the methods, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate; 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

In another preferred embodiment of the methods, the growth hormone secretagogue is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

Also provided is a sustained release dosage form for administration of 2-amino-N-[2-(3a-(R)-benzyl-2-methyl-3-oxo-2,3,3a,4,6,7-hexahydro-pyrazoro[4,3-c]pyridin-5-yl)-1-(R)-benzyloxymethyl-2-oxo-ethyl]-isobutyramide L-tartrate to a mammal, the dosage form comprising a core comprising:

1) 2-amino-N-[2-(3a-(R)-benzyl-2-methyl-3-oxo-2,3,3a,4,6,7-hexahydro-pyrazolo[4,3-c]pyridin-5yl)-1(R)-benzyloxymethyl-2-oxo-ethyl]-isobutyramide L-tartrate;
2) one or more osmotic agents selected from lactose, mannitol, sorbitol, or sodium bitartrate;
3) microcrystalline cellulose;
4) magnesium stearate; and
5) one or more acids selected from ascorbic acid, L-aspartic acid, citric acid, fumaric acid, succinic acid, or tartaric acid upon which core is coated an asymmetric membrane comprising cellulose acetate and polyethylene glycol.

Also provided by the present invention are combination dosage forms for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage forms comprising two portions: A) a portion that immediately releases an amount of a growth hormone secretagogue; and B) a portion that provides for sustained release of an amount of a growth hormone secretagogue, the sustained release portion of the dosage form comprising an asymmetric membrane coated osmotic tablet, the osmotic tablet comprising:

1) 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate;

2) one or more osmotic agents selected from lactose, mannitol, sorbitol, or sodium bitartrate;
3) microcrystalline cellulose;
4) magnesium stearate; and
5) one or more acids selected from ascorbic acid, L-aspartic acid, citric acid, fumaric acid, succinic acid, or tartaric acid;

and the asymmetric membrane comprising:
cellulose acetate and polyethylene glycol; and the immediate release portion comprising a compression coating placed upon the asymmetric membrane coated tablet, wherein the compression coating comprises 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, microcrystalline cellulose, and magnesium stearate.

Also provided is a sustained release dosage form for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage form comprising:

| Component | Weight (mg/tablet) |
|---|---|
| 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate | about 3.89 |
| Mannitol | about 34.00 |
| Fumaric acid | about 12.00 |
| Microcrystalline cellulose | about 48.61 |
| Magnesium stearate | about 1.50 |
| Cellulose acetate | about 11.90 |
| Polyethylene glycol | about 5.10 |

Also provided is a sustained release dosage form for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage form comprising:

| Component | Weight (mg/tablet) |
|---|---|
| 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate | about 12.97 |
| Mannitol | about 113.32 |
| Fumaric acid | about 40.00 |
| Microcrystalline cellulose | about 162.01 |
| Magnesium stearate | about 5.00 |
| Cellulose acetate | about 33.00 |
| Polyethylene glycol | about 22.00 |

Also provided is a combination dosage form for administering a therapeutically active compound to a mammal in need thereof, the dosage form comprising an immediate release portion and a sustained release portion wherein the sustained release portion comprises an osmotic tablet, which has a membrane coating, and the immediate release portion comprises a compression coating on the osmotic tablet.

In a preferred embodiment of the combination dosage form, the therapeutically active compound is a growth hormone secretagogue.

In another preferred embodiment of the combination dosage form, the therapeutically active compound is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

DETAILED DESCRIPTION OF THE INVENTION

The present invention provides sustained release dosage forms for growth hormone secretagogues (GHSECs). The present invention also provides dosage forms that immediately release an amount of a GHSEC and release an amount of a GHSEC in a sustained manner.

The term "sustained release" means that active compound or compounds are released over a period of time. Preferably, the amount of compound released over a period of time is relatively constant.

The term "growth hormone secretagogue" includes the pharmaceutically acceptable salts and prodrugs, and prodrugs of the salts, polymorphs, hydrates, solvates, and stereoisomers of the growth hormone secretagogue.

The terms "active compound" or "active agent" means a compound that exerts a pharmacological effect on a patient. These terms are intended to include salts and prodrugs of the compound and salts of the prodrugs.

The present invention provides sustained release formulations of a growth hormone secretagogue or a combination of growth hormone secretagogues. The sustained release formulations of the present invention release a GHSEC in vivo at a rate that results in therapeutic plasma levels of the GHSEC for extended periods of the day. Since GHSECs are typically polar molecules, it was not known whether the permeability of the intestinal wall, particularly the colon, would be sufficient to permit absorption over an extended period. The GHSEC formulations of the present invention surprisingly give plasma levels of GHSEC for extended periods of the dosing day, and can be administered just once per day to give adequate therapy. Furthermore, when the sustained release formulations of the present invention are administered daily for three or more weeks, plasma levels of IGF-I are increased with respect to baseline levels, while GH levels are decreased or unchanged with respect to baseline levels. In other words, over time IGF-1 plasma levels are elevated, and GH levels are decreased or unchanged with respect to baseline plasma levels. Thus, the therapeutic benefits of elevated IGF-1 levels may be obtained while minimizing any undesired effects that result from increased GH plasma levels.

Any GHSEC can be used in the present invention. The following patents and applications disclose GHSECs that can be used in the present invention: PCT/US93/11038, WO 98/46569, WO 98/51687, WO 98/58950, WO 99/08697, WO 99/09991, WO 95/13069, U.S. Pat. Nos. 5,492,916, 5,494,919, WO 95/14666, WO 94/19367, WO 94/13696, WO 94/11012, U.S. Pat. No. 5,726,319, WO 95/11029, WO 95/17422, WO 95/17423, WO 95/34311, WO 96/02530, WO 96/22996, WO 96/22997, WO 96/24580, WO 96/24587, U.S. Pat. No. 5,559,128, WO 96/32943, WO 96/33189, WO 96/15148, WO 97/00894, WO 97/07117, WO 97/06803, WO 97/11697, WO 97/15573, WO 97/22367, WO 97/23508, WO 97/22620, WO 97/22004, WO 97/21730, U.S. Pat. No. 5,663,171, WO 97/34604, WO 97/36873, WO 97/40071, WO 97/40023, WO 97/41878, WO 97/41879, WO 97/46252, WO 97/44042, WO 97/38709, WO 98/03473, WO 97/43278, U.S. Pat. Nos. 5,721,251, 5,721,250, WO 98/10653, WO 96/38471, WO 96/35713, U.S. Pat. Nos. 5,919,777, and 5,830,433.

In addition, the following growth hormone secretagogues are contemplated for use in the present invention: MK-0677 (Merck); NM703 (Novo Nordisk); L-162752 and L-163022 (Merck); hexarelin (Pharmacia Corporation); GPA-748, KP102, and GHRP-2 (American Home Products); ipamorelin (Novo Nordisk); LY444711 (Eli Lilly); Geref (Ares/Serono); GHRH (1-44) [BioNebraska]; Somatorelin (GRF 1-44) [Fujisawa/ICN]; and ThGRF (Theratechnologies).

Preferred GHSECs that can be used in the present invention include: 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt or prodrug thereof, or a salt of the prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate; 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a ,4,6,7-hexahydro-pyrazolo[4,3-c]pyridin-5-yl]-ethyl}-2-methyl-propionamide or a pharmaceutically acceptable salt or prodrug thereof, or a salt of the prodrug; or the (L)-(+)-tartaric acid salt of 2-amino-N-{1-(R)-(2,4-difluoro-benzyloxymethyl)-2-oxo-2-[3-oxo-3a-(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide. The procedures for making these compounds are disclosed in WO 97/24369 and WO 98/58947. Particularly preferred GHSECs for use in the present invention include GHSECs that have a plasma half-life in humans of less than about 6 hours, and preferably of less than about 4 hours. It is also noted that the formulations of the present invention can contain more than one GHSEC. For example, two GHSECs can be administered in a sustained release formulation. Similarly, two GHSECs can be administered in a formulation that has an immediate release portion and a sustained release portion. In one embodiment of the formulation that has an immediate release and a sustained release portion, one GHSEC can be used in the immediate release portion and a different GHSEC can be used in the sustained release portion.

Dosing a GHSEC sustained release dosage form (SRDF) for greater than three weeks resulted in elevated plasma IGF-I levels, without significant elevation of plasma GH levels. The GHSEC SRDF that was used to demonstrate this effect in humans resulted in at least two major pharmacokinetic effects: the GHSEC plasma $C_{max}$ was lowered, and the time duration for which the GHSEC plasma level exceeds about 1 or about 2 ng/ml was extended when compared to an immediate release dosage form administering the same amount of GHSEC. The sustained release dosage forms (SRDF) of the present invention meet either or both of the following criteria:

(1) The $C_{max}$ Criterion.

When the GHSEC SRDF is dosed to a mammal, the resulting maximum GHSEC plasma concentration $C_{max}$ is less than 80% of the $C_{max}$ resulting from dosing an immediate release dosage form (IRDF) at the same dose. An IRDF comprises a GHSEC solution, suspension, tablet, or capsule with no incorporated mechanism for delaying or slowing the dissolution of the active compound after administration. It is preferred that the total active compound exposure not be decreased as much as $C_{max}$. That is, the AUC(SRDF)/AUC(IRDF) is greater than the $C_{max}$(SRDF)/$C_{max}$(IRDF), where AUC is the area under the plasma active compound concentration versus time plot.

(2) The ΔT Criterion.

When the GHSEC SRDF is dosed to a mammal, the resulting GHSEC plasma concentration remains above the minimum therapeutic GHSEC plasma concentration for at least 30 minutes longer than would occur after dosing a GHSEC IRDF at the same dose. For humans the minimum therapeutically effective GHSEC plasma concentration is about 1 ng/ml or greater. A preferred effective GHSEC plasma concentration is about 2 ng/ml or greater. Preferred GHSEC SRDFs of this invention meet both the $C_{max}$ and ΔT criteria.

Exemplary sustained release dosage forms of this invention which meet the $C_{max}$ criterion, wherein the GHSEC is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate are those which release the above GHSEC at a rate of:

about 0.007 to about 0.010 mg/hr/kg for about a 4 mg dose;

about 0.007 to about 0.014 mg/hr/kg for about a 6 mg dose;

about 0.006 to about 0.019 mg/hr/kg for about a 8 mg dose;

about 0.010 to about 0.029 mg/hr/kg for about a 12 mg dose;

about 0.013 to about 0.038 mg/hr/kg for about a 16 mg dose;

about 0.019 to about 0.057 mg/hr/kg for about a 24 mg dose; and about 0.038 to about 0.114 mg/hr/kg for about a 48 mg dose, where mg refers to mg GHSEC, and kg refers to the weight of the mammal under treatment. Preferably, the mammal is a human.

Exemplary sustained release dosage forms of this invention which meet the ΔT criterion, wherein the GHSEC is the 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate are those which release the GHSEC at a rate of:

about 0.009 to about 0.021 mg/hr/kg for about a 6 mg dose;

about 0.006 to about 0.029 mg/hr/kg for about a 8 mg dose;

about 0.010 to about 0.043 mg/hr/kg for about a 12 mg dose;

about 0.013 to about 0.057 mg/hr/kg for about a 16 mg dose;

about 0.019 to about 0.086 mg/hr/kg for about a 24 mg dose; and about 0.034 to about 0.343 mg/hr/kg for about a 48 mg dose, where mg refers to mg GHSEC, and kg refers to the weight of the mammal under treatment. Preferably, the mammal is a human.

These release rate ranges were determined by the pharmacokinetic modeling described in the Examples below, and assume a desired therapeutic plasma level of 2 ng/ml. The pharmacokinetic modeling studies utilized data from a study in which the compound was dosed to human subjects. For some therapeutic indications, 1 ng/ml GHSEC in plasma will be effective. Appropriate release rates for lower doses (e.g., less than 4 mg), for intermediate doses (e.g., 5 mg, 7 mg, 10 mg, 16 mg), or lower therapeutic active compound plasma levels (e.g., less than 2 ng/ml) may be determined as illustrated below in the Examples.

The present invention also relates to a combination dosage form that comprises a sustained release portion and an immediate release portion. Such dosage forms release a part of the GHSEC immediately after dosing, and release another part of the GHSEC in a sustained manner. Formulations of this type meet either or both of the $C_{max}$ or $\Delta T$ criteria described above. Preferred formulations meet both criteria. Exemplary combination formulations of the present invention that comprise a sustained release and immediate release portion that meet the $C_{max}$ criterion above for 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate include forms that release:

about 5 to about 50% GHSEC immediately, and the rest of the dose over about 4 to about 6 hr, for about a 4 mg dose;

about 50 to about 75% GHSEC immediately, and the rest over about 8 to about 10 hr, for about a 4 mg dose;

about 75% GHSEC immediately, and the rest over about 12 to about 18 hr, for about a 4 mg dose;

about 40% GHSEC immediately, and the rest over about 4 hr, for about a 6 mg dose;

about 5 to about 40% GHSEC immediately, and the rest over about 6 hr, for about a 6 mg dose;

about 5 to about 75% GHSEC immediately, and the rest over about 8 to about 12 hr, for about a 6 mg dose;

about 40 to about 75% GHSEC immediately, and the rest over about 14 to about 18 hr, for about a 6 mg dose;

about 40% GHSEC immediately, and the rest over about 4 hr, for about a 12 mg dose;

about 5 to about 40% GHSEC immediately, and the rest over about 6 hr, for about a 12 mg dose;

about 5 to about 62.5% GHSEC immediately, and the rest over about 8 hr, for about a 12 mg dose;

about 5 to about 75% GHSEC immediately, and the rest over about 12 to about 18 hr, for about a 12 mg dose; and about 5 to about 75% GHSEC immediately, and the rest over about 16 hr, for about a 48 mg dose.

Exemplary formulations of the present invention that have an immediate release and a sustained release portion that meet the $\Delta T$ criterion and wherein the GHSEC is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, are those which release:

about 5 to about 40% GHSEC immediately, and the rest over about 4 hr, for about a 6 mg dose;

about 5 to about 75% GHSEC immediately, and the rest over about 6 hr, for about a 6 mg dose;

about 5 to about 62.5% GHSEC immediately, and the rest over about 8 hr, for about a 6 mg dose;

about 5 to about 40% GHSEC immediately, and the rest over about 10 hr, for about a 6 mg dose;

about 5 to about 40% GHSEC immediately, and the rest over about 4 hr, for about a 12 mg dose;

about 5 to about 75% GHSEC immediately, and the rest over about 6 to about 16 hr, for about a 12 mg dose;

about 5 to about 40% GHSEC immediately, and the rest over about 18 hr, for about a 12 mg dose; and about 5 to about 75% GHSEC immediately, and the rest over about 16 hr, for about a 48 mg dose.

The ranges of % immediate release component, and duration of release of sustained release component, were determined by the pharmacokinetic modeling described in the Examples below, and assume a desired therapeutic plasma level of 2 ng/ml. For some therapeutic indications, 1 ng/ml GHSEC in plasma will be effective. Appropriate release rates for lower doses (e.g., less than 4 mg), for intermediate doses (e.g. 5 mg, 7 mg, 10 mg, 16 mg), or for lower therapeutic active compound plasma levels (e.g. less than 2 ng/ml) may be determined as illustrated in the Examples.

The sustained-release dosage forms useful in this invention can be widely implemented. For purposes of discussion, not limitation, the many embodiments hereunder can be grouped into classes according to design and principle of operation.

The first class of sustained release dosage forms described below is matrix systems, which include but are not limited to 1) non-eroding matrices, tablets, multiparticulates, and hydrogel-based systems; 2) hydrophilic eroding, dispersible or dissolvable matrix systems, tablets and multiparticulates; and 3) coated matrix systems. The second class comprises reservoir systems where release of the active compound is modulated by a membrane, such as capsules, and coated tablets or multiparticulates. The third class comprises osmotic-based systems such as 1) coated bilayer tablets; 2) coated homogeneous tablet cores; 3) coated multiparticulates; and 4) osmotic capsules. The fourth class comprises swellable systems where active compound is released by swelling and extrusion of the core components out through a passageway in a coating or surrounding shell or outer layer. Each of the different types of sustained release dosage forms can be used to administer a GHSEC in accordance with the present invention to achieve the desired $C_{max}$ and/or $\Delta T$ criteria that provides for, over time, increased IGF-1 plasma levels and decreased or normal GH plasma levels when compared with baseline plasma levels.

A first class includes matrix systems, in which a GHSEC is dissolved, embedded or dispersed in a matrix of another material that serves to retard the release of the GHSEC into an aqueous environment [e.g., the lumenal fluid of the gastrointestinal tract (GI)]. When a GHSEC is dissolved, embedded or dispersed in a matrix of this sort, release of the active compound takes place principally from the surface of the matrix. Thus, the GHSEC is released from the surface of a device which incorporates the matrix after it diffuses through the matrix into the surrounding fluid or when the surface of the device dissolves or erodes, exposing the active compound. In some embodiments, both mechanisms can operate simultaneously. The matrix systems may be large, i.e., tablet sized (about 1 cm), or small (<0.3 cm). The system may be unitary, it may be divided by virtue of being composed of several sub-units (for example, several tablets which constitute a single dose) which are administered substantially simultaneously, it may consist of several small tablets within a capsule, or it may comprise a plurality of particles, referred to herein as a multiparticulate. A multiparticulate can have numerous formulation applications. For example, a multiparticulate may be used as small beads or as powder for filling a capsule shell, it may be compressed into a tablet, or it may be used per se for mixing with food (for example, ice cream) to increase palatability, or as a sachet that may be dispersed in a liquid, such as fruit juice or water.

The multiplicity of variables affecting release of a GHSEC from matrix devices permits abundant flexibility in the design of devices of different materials, sizes, and release times.

Non-eroding matrix tablets that provide sustained release of a GHSEC can be made with a GHSEC and water insoluble materials such as waxes, cellulose, or other water insoluble polymers. Matrix materials useful for the manufacture of these dosage forms include microcrystalline cellulose such as Avicel® (FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as polymers such as cellulose, cellulose esters, cellulose ethers, poly(vinyl chloride), poly(vinyl acetate), copolymers of vinyl acetate and ethylene, polystyrene, and the like. Water soluble binders or release modifying agents which can optionally be formulated into the matrix include water-soluble polymers such as hydroxypropyl cellulose (HPC), hydroxypropyl methyl cellulose (HPMC), methyl cellulose, poly (N-vinyl-2-pyrrolidinone) (PVP), poly (ethylene oxide) (PEO), poly(vinyl alcohol) (PVA), xanthan gum, carrageenan, and other such natural and synthetic materials. In addition, materials that function as release-modifying agents include water-soluble materials such as sugars or salts. Preferred water-soluble materials include lactose, sucrose, glucose, and mannitol, as well as HPC, HPMC, and PVP. In addition, solubilizing acid excipients such as organic acids including but not limited to malic acid, citric acid, erythorbic acid, ascorbic acid, adipic acid, glutamic acid, maleic acid, aconitic acid, fumaric acid, succinic acid, tartaric acid, and aspartic acid and solubilizing excipients such as sodium bitartrate and cyclodextrins, can be incorporated into matrix tablets to increase the release rate of the GHSEC, increase the total quantity of the GHSEC released, and potentially increase absorption and consequently the bioavailability of the GHSEC, particularly from matrix formulations that release the GHSEC over a period of six hours or longer.

In addition to components of the matrix system, the size of the matrix system can affect the rate of GHSEC release; therefore, a large matrix system such as a tablet will, in general, have a different composition from a small one such as a multiparticulate to achieve similar release profiles. The effect of the size of the matrix system on the kinetics of GHSEC release follows scaling behavior well known to those skilled in the art. By way of illustration, the following table shows the diffusion coefficient of a GHSEC through the matrix required to achieve a characteristic time for release of 10 hours for matrix systems of different sizes that release a GHSEC by a diffusive-based mechanism (rather than an eroding or in combination with an eroding mechanism).

| radius (cm) | diffusion coefficient ($cm^2$/sec) |
|---|---|
| 0.0025 (50 μm diameter) | $1.7 \times 10^{-10}$ |
| 0.1 (2 mm diameter) | $3 \times 10^{-7}$ |
| 0.5 (1 cm diameter) | $7 \times 10^{-6}$ |

The above table illustrates that diffusion coefficients necessary to achieve the target characteristic time of release can change by orders of magnitude as the desired size of the device changes. Matrix materials that can be used to provide a GHSEC diffusion coefficient at the low end of the diffusion coefficient scale are polymers such as cellulose acetate. Conversely, materials at the upper end of the scale are materials such as polymers that form hydrogels or a water-swollen mass when hydrated. The rate of diffusion for any particular device can accordingly be tailored by the material or materials selected and the structure of the matrix.

For purposes of further illustration, to obtain a sustained release non-eroding matrix in a particle of about 50 μm in diameter, a matrix material of a polymer such as cellulose acetate or a similar material will likely be required, the slow diffusing matrix material tending to offset the short distances characteristic of small particle size. In contrast, in order to obtain sustained release in a large (e.g., 1 cm) device, a material which is more liquid-like (e.g., a hydrogel or water-soluble polymer) or with greater porosity will likely be required. For devices of an intermediate size, e.g., about 1 mm in diameter, a matrix composition of intermediate characteristics can be employed.

It is also noted that the effective diffusion coefficient of a GHSEC in a matrix may be increased to the desired value by the addition of plasticizers, pores, or pore-inducing additives, as known in the art. Slowly hydrating materials may also be used to effectively reduce the diffusion rates of a GHSEC, particularly at times shortly after administration. In addition to changing the effective diffusion coefficient, the release rate can also be altered by the inclusion of more soluble salt forms of the GHSEC (relative to the free base form) or excipients such as acids that solubilize the GHSEC.

A further sustained release non-eroding matrix system comprises a GHSEC dispersed in a hydrogel matrix. This embodiment differs from the hydrophilic matrix tablet in that the hydrogel of this embodiment is not a compressed tablet of soluble or erodible granular material, but rather is a monolithic polymer network. As is known in the art, a hydrogel is a water-swellable network polymer. Hydrogels can be made in many geometries, such as caplets, tablets, and multiparticulates. As an example, tablets can be prepared by standard techniques containing 10 to 80% of a crosslinkable polymer. Once tablets are formed the polymer can be crosslinked via a chemical crosslinking agent such as gluteraldehyde or via UV irradiation forming a hydrogel matrix. Hydrogels are preferred materials for matrix devices because they can absorb or be made to contain a large volume fraction of water, thereby permitting diffusion of solvated active compound within the matrix. Diffusion coefficients of active compounds in hydrogels are characteristically high, and for highly water-swollen gels, the diffusion coefficient of the active compound in the gel may approach the value in pure water. This high diffusion coefficient permits practical release rates from relatively large devices (i.e., it is not necessary to form microparticles). Although hydrogel devices can be prepared, loaded with a GHSEC, stored, dispensed and dosed in the fully hydrated state, it is preferred that they be stored, dispensed, and dosed in a dry state. In addition to stability and convenience, dry state dosing of hydrogel devices can provide good GHSEC release kinetics due to Case II transport (i.e., combination of swelling of hydrogel and diffusion of active compound out through the swollen hydrogel). Preferred materials for forming hydrogels include hydrophilic vinyl and acrylic polymers, polysaccharides such as calcium alginate, and poly(ethylene oxide). Especially preferred are poly(2-hydroxyethyl methacrylate), poly(acrylic acid), poly (methacrylic acid), poly(N-vinyl-2-pyrolidinone), poly (vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated.

Non-eroding matrix tablets can be made by tabletting methods common in the pharmaceutical industry. Preferred embodiments of non-eroding matrix tablets contain about 1 to about 80% GHSEC, about 5 to about 50% insoluble matrix materials such as cellulose, cellulose acetate, or ethylcellulose, and optionally about 5 to about 85% plasticizers, pore formers or solubilizing excipients, and optionally about 0.25 to about 2% of a tabletting lubricant, such as magnesium stearate, sodium stearyl fumarate, zinc stearate, calcium stearate, stearic acid, polyethyleneglycol-8000, talc, or mixtures of magnesium stearate with sodium lauryl sulfate. These materials can be blended, granulated, and tabletted using a variety of equipment common to the pharmaceutical industry.

A non-eroding matrix multiparticulate comprises a plurality of GHSEC-containing particles, each particle comprising a mixture of GHSEC with one or more excipients selected to form a matrix capable of limiting the dissolution rate of the GHSEC into an aqueous medium. The matrix materials useful for this embodiment are generally water-insoluble materials such as triglycerides, waxes, cellulose, or other water-insoluble polymers. If needed, the matrix materials may optionally be formulated with water-soluble materials that can be used as binders or as permeability-modifying agents. Matrix materials useful for the manufacture of these dosage forms include microcrystalline cellulose such as Avicel® (FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble release modifying agents that can optionally be formulated into the matrix include water-soluble polymers such as HPC, HPMC, methyl cellulose, PVP, PEO, PVA, xanthan gum, carrageenan, and other such natural and synthetic materials. In addition, materials that function as release-modifying agents include water-soluble materials such as sugars or salts. Preferred water-soluble materials include lactose, sucrose, glucose, and mannitol, as well as HPC, HPMC, and PVP. In addition, any of the solubilizing acids or excipients previously mentioned can be incorporated into matrix multiparticulates to increase the release rate of the GHSEC, increase the total quantity of the GHSEC released, and potentially increase absorption and consequently the bioavailability of the GHSEC, particularly from matrix formulations that release the GHSEC over a period of six hours or longer.

A preferred process for manufacturing matrix multiparticulates is the extrusion/spheronization process. For this process, the GHSEC is wet-massed with a binder, extruded through a perforated plate or die, and placed on a rotating disk. The extrudate ideally breaks into pieces, which are rounded into spheres, spheroids, or rounded rods on the rotating plate. A preferred process and composition for this method involves using water to wet-mass a blend comprising about 20 to about 99% of microcrystalline cellulose blended with, correspondingly, about 80 to about 1% GHSEC.

A preferred process for manufacturing matrix multiparticulates is the rotary granulation process. For this process the GHSEC and excipients such as microcrystalline cellulose are placed in a rotor bowl in a fluid-bed processor. The active compound and excipient are fluidized, while spraying a solution that binds the active compound and excipients together in granules or multiparticulates. The solution sprayed into the fluid bed can be water or aqueous solutions or suspensions of binding agents such as polyvinylpyrrolidone or hydroxypropylmethylcellulose. A preferred composition for this method can comprise about 1 to about 80% GHSEC, about 10 to about 60% microcrystalline cellulose, and about 0 to about 25% binding agent.

A further preferred process for manufacturing matrix multiparticulates involves coating the GHSEC, matrix-forming excipients, and if desired, release-modifying or solubilizing excipients onto seed cores such as sugar seed cores known as non-pareils. Such coatings can be applied by many methods known in the pharmaceutical industry, such as spray-coating in a fluid bed coater, spray-drying, and granulation methods such as fluid bed or rotary granulation. Coatings can be applied from aqueous, organic or melt solutions or suspensions.

A further preferred process for manufacturing matrix multiparticulates is the preparation of wax granules via a melt-congeal process. In this process, a desired amount of the GHSEC is stirred with liquid wax to form a homogeneous mixture, cooled and then forced through a screen to form granules. Alternatively, the homogeneous mixture can be fed to a spinning disc where the mixture is broken up into droplets as it is spun off the edges of the disc. These droplets are then cooled, and solidify before landing in a collection chamber. Preferred matrix materials are waxy substances. Especially preferred are hydrogenated castor oil, glyceryl behenate, microcrystalline wax, carnauba wax, and stearyl alcohol.

A further preferred process for manufacturing matrix multiparticulates involves using an organic solvent to aid mixing of the GHSEC with the matrix material. This technique can be used when it is desired to utilize a matrix material with an unsuitably high melting point that, if the material were employed in a molten state, would cause decomposition of the active compound or of the matrix material, or would result in an unacceptable melt viscosity, thereby preventing mixing of the GHSEC with the matrix material. GHSEC and matrix material may be combined with a modest amount of solvent to form a paste, and then forced through a screen to form granules from which the solvent is then removed. Alternatively, the GHSEC and matrix material may be combined with enough solvent to completely dissolve the matrix material and the resulting solution (which may contain solid active compound particles) spray dried to form the particulate dosage form. This technique is preferred when the matrix material is a high molecular weight synthetic polymer such as a cellulose ether or cellulose ester. Solvents typically employed for the process include acetone, ethanol, isopropanol, ethyl acetate, and mixtures of two or more.

A further process for manufacturing matrix multiparticulates involves using an aqueous solution or suspension of the GHSEC and matrix forming materials. The solution or suspension can be spray dried or sprayed or dripped into a quench bath or through a light chamber to initiate crosslinking of matrix materials and solidify the droplets. In this manner matrices can be made from latexes (e.g., dispersed ethyl cellulose with a plasticizer such as oleic acid or with a volatile water miscible solvent such as acetone or ethanol) by spray-drying techniques. Matrices can also be made in this manner by crosslinking a water soluble polymer or gum. For example, sodium alginate can be crosslinked by spraying into a solution containing soluble calcium salts, polyvinyl alcohol can be crosslinked by spraying into a solution containing gluteraldehyde, and di- and tri-acrylates can be crosslinked by UV irradiation.

Once formed, GHSEC matrix multiparticulates may be blended with compressible excipients such as lactose, mannitol, microcrystalline cellulose, dicalcium phosphate, and the like and the blend compressed to form a tablet. Disintegrants such as sodium starch glycolate, sodium croscarmellose, or crosslinked poly(vinyl pyrrolidone) are also usefully employed. Tablets prepared by this method disintegrate when placed in an aqueous medium (such as the GI tract), thereby exposing the multiparticulate matrix, which releases the GHSEC. GHSEC matrix multiparticulates may also be filled into capsules, such as hard gelatin capsules. Multiparticulates can also be directly dosed as a sachet that is mixed with water or other suitable drink, or can be sprinkled directly on food.

A further embodiment of a matrix system has the form of a hydrophilic matrix tablet containing a GHSEC that eventually dissolves or disperses in water and an amount of hydrophilic polymer sufficient to provide a useful degree of control over the release of GHSEC. GHSEC can be released from such matrices by diffusion, erosion or dissolution of the matrix, or a combination of these mechanisms. Hydrophilic polymers useful for forming a hydrophilic matrix include HPMC, HPC, hydroxy ethyl cellulose (HEC), PEO, PVA, polyacrylic acid, xanthan gum, carbomer, carrageenan, and zooglan. A preferred material is HPMC. Other similar hydrophilic polymers may also be employed. In use, the hydrophilic material is swollen by, and eventually dissolves or disperses in, water. The GHSEC release rate from hydrophilic matrix formulations may be controlled by the amount and molecular weight of hydrophilic polymer employed. In general, using a greater amount of the hydrophilic polymer decreases the release rate, as does using a higher molecular weight polymer. Using a lower molecular weight polymer increases the release rate. The release rate may also be controlled by the use of water-soluble additives such as sugars, salts, or soluble polymers. Examples of these additives are sugars such as lactose, sucrose, or mannitol, salts such as NaCl, KCl, $NaHCO_3$, and water soluble polymers such as PVP, low molecular weight HPC or HMPC or methyl cellulose. In general, increasing the fraction of soluble material in the formulation increases the release rate. In addition, any of the solubilizing acid excipients previously mentioned can be incorporated into matrix tablets to increase the release rate of GHSEC, increase the total quantity of GHSEC released, and potentially increase absorption and consequently the bioavailability of GHSEC, particularly from matrix formulations that release GHSEC over a period of six hours or longer. A hydrophilic matrix tablet typically comprises about 1 to about 90% by weight of the GHSEC and about 80 to about 10% by weight of polymer.

A preferred hydrophilic matrix tablet comprises, by weight, about 3% to about 80% GHSEC, about 5% to about 35% HPMC, about 0% to about 55% lactose or mannitol, about 0% to about 15% PVP, about 0% to about 20% microcrystalline cellulose, and about 0.25% to about 2% magnesium stearate.

Mixtures of polymers and/or gums can also be utilized to make hydrophilic matrix systems. For example, homopolysaccharide gums such as galactomannans (e.g., locust bean gum or guar gum) mixed with heteropolysaccharide gums (e.g., xanthan gum or its derivatives) can provide a synergistic effect that in operation provides faster forming and more rigid matrices for the release of active compound (See, for example, U.S. Pat. Nos. 5,455,046 and 5,512,297). Optionally, crosslinking agents such as calcium salts can be added to improve matrix properties.

Hydrophilic matrix formulations that eventually dissolve or disperse can also be made in the form of multiparticulates. Hydrophilic matrix multiparticulates can be manufactured by the techniques described previously for non-eroding matrix multiparticulates. Preferred methods of manufacture are layering GHSEC, a hydrophilic matrix material, and if desired release modifying agents onto seed cores (e.g., non-pareils) via a spray-coating process or forming multiparticulates by granulation, such as by rotary granulation of GHSEC, hydrophilic matrix material, and if desired, release modifying agents.

The matrix systems as a class often exhibit non-constant release of the active compound from the matrix. This result may be a consequence of the diffusive mechanism of active compound release, and modifications to the geometry of the dosage form and/or coating or partially coating the dosage form can be used to advantage to make the release rate of the active compound more constant as detailed below.

In a further embodiment, a GHSEC matrix tablet is coated with an impermeable coating, and an orifice (for example, a circular hole or a rectangular opening) is provided by which the content of the tablet is exposed to the aqueous GI tract. These embodiments are along the lines of those presented in U.S. Pat. No. 4,792,448 to Ranade, and as described by Hansson et al., *J. Pharm. Sci.,* 77 (1988) 322–324. The opening is typically of a size such that the area of the exposed underlying GHSEC constitutes less than about 40% of the surface area of the device, preferably less than about 15%.

In another embodiment, a GHSEC matrix tablet is coated with an impermeable material on part of its surface, e.g., on one or both tablet faces, or on the tablet radial surface.

In another embodiment, a GHSEC matrix tablet is coated with an impermeable material and an opening for active compound transport produced by drilling a hole through the coating. The hole may be through the coating only, or may extend as a passageway into the tablet.

In another embodiment, a GHSEC matrix tablet is coated with an impermeable material and a passageway for active compound transport produced by drilling a passageway through the entire tablet.

In another embodiment, a GHSEC matrix tablet is coated with an impermeable material and one or more passageways for active compound transport are produced by removing one or more strips from the impermeable coating or by cutting one or more slits through the coating, preferably on the radial surface or land of the tablet.

In another embodiment, a GHSEC matrix tablet is shaped in the form of a cone and completely coated with an impermeable material. A passageway for active compound transport is produced by cutting off the tip of the cone.

In another embodiment, a GHSEC matrix tablet is shaped in the form of a hemisphere and completely coated with an impermeable material. A passageway for active compound transport is produced by drilling a hole in the center of the flat face of the hemisphere.

In another embodiment, a GHSEC matrix tablet is shaped in the form of a half-cylinder and completely coated with an impermeable material. A passageway for GHSEC transport is produced by cutting a slit through (or removing a strip from) the impermeable coating along the axis of the half-cylinder along the centerline of the flat face of the half-cylinder. Those skilled in the art will appreciate that the geometric modifications to the embodiments described above can be equivalently produced by more than one method.

By "impermeable material" is meant a material having sufficient thickness and impermeability to GHSEC such that the majority of GHSEC is released through the passageway rather than through the "impermeable material" during the time scale of the intended active compound release. Such a coating can be obtained by selecting a coating material with a sufficiently low diffusion coefficient for GHSEC and applying it sufficiently thickly. Materials for forming the impermeable coating of these embodiments include substantially all materials in which the diffusion coefficient of the GHSEC is less than about $10^{-7}$ $cm^2$/sec. It is noted that the preceding diffusion coefficient can be amply sufficient to allow release of GHSEC from a matrix device, as discussed above. However, for a device of the type now under discussion that has been provided with a macroscopic opening or passageway, a material with this diffusion coefficient is effectively impermeable to GHSEC relative to GHSEC transport through the passageway. Preferred coating materials include film-forming polymers and waxes. Especially preferred are thermoplastic polymers, such as poly(ethylene-co-vinyl acetate), poly(vinyl chloride), ethylcellulose, and cellulose acetate. These materials exhibit the desired low permeation rate of GHSEC when applied as coatings of thickness greater than about 100 $\mu$m.

A second class of GHSEC sustained-release dosage forms of the present invention includes membrane-moderated or reservoir systems such as membrane-coated diffusion-based capsule, tablet, or multiparticulate. Capsules, tablets and multiparticulates can all be reservoir systems, such as membrane-coated diffusion-based. In this class, a reservoir of GHSEC is surrounded by a rate-limiting membrane. The GHSEC traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule containing a plurality of reservoir particles, each individually coated with a membrane. The coating can be non-porous, yet permeable to GHSEC (for example, GHSEC may diffuse directly through the membrane), or it may be porous.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary bed coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores that facilitate release of the active compound. The membrane coating can also be modified by the addition of plasticizers, as known in the art.

A particularly useful variation of the process for applying a membrane coating comprises dissolving the coating polymer in a mixture of solvents chosen such that as the coating dries, a phase inversion takes place in the applied coating solution, resulting in a membrane with a porous structure. Numerous examples of this type of coating system are given in U.S. Pat. No. 5,612,059.

The morphology of the membrane is not of critical importance so long as the permeability characteristics enumerated herein are met. However, specific membrane designs will have membrane morphology constraints in order to achieve the desired permeability. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such membrane designs which are characterized by controlled permeability to GHSEC.

A useful reservoir system embodiment is a capsule having a shell comprising the material of the rate-limiting membrane, including any of the membrane materials previously discussed, and filled with a GHSEC active compound composition. A particular advantage of this configuration is that the capsule may be prepared independently of the active compound composition, thus process conditions that would adversely affect the active compound can be used to prepare the capsule. A preferred embodiment is a capsule having a shell made of a porous or a permeable polymer made by a thermal forming process. An especially preferred embodiment is a capsule shell in the form of an asymmetric membrane; i.e., a membrane that has a thin dense region on one surface and most of whose thickness is constituted of a highly permeable porous material. A preferred process for preparation of asymmetric membrane capsules comprises a solvent exchange phase inversion, wherein a solution of polymer, coated on a capsule-shaped mold, is induced to phase-separate by exchanging the solvent with a miscible non-solvent. Examples of asymmetric membranes useful in this invention are disclosed in U.S. Pat. Nos. 5,698,220 and 5,612,059.

Tablets can also be reservoir systems. Tablet cores containing GHSEC can be made by a variety of techniques standard in the pharmaceutical industry. These cores can be coated with a rate-controlling coating as described above, which allows the GHSEC in the reservoir (tablet core) to diffuse out through the coating at the desired rate.

Another embodiment of reservoir systems comprises a multiparticulate wherein each particle is coated with a polymer designed to yield sustained release of GHSEC. The multiparticulate particles each comprise GHSEC and one or more excipients as needed for fabrication and performance. The size of individual particles, as previously mentioned, is generally between about 50 $\mu$m and about 3 mm, although beads of a size outside this range may also be useful. In general, the beads comprise GHSEC and one or more binders. As it is generally desirable to produce dosage forms that are small and easy to swallow, beads that contain a high fraction of GHSEC relative to excipients are preferred. Binders useful in fabrication of these beads include microcrystalline cellulose (e.g., Avicel®, FMC Corp.), HPC, HPMC, and related materials or combinations thereof. In general, binders that are useful in granulation and tabletting, such as starch, pregelatinized starch, and PVP may also be used to form multiparticulates.

Reservoir system GHSEC multiparticulates may be prepared using techniques known to those skilled in the art, including, but not limited to, the techniques of extrusion and spheronization, wet granulation, fluid bed granulation, melt-congealing, and rotary bed granulation. In addition, the beads may also be prepared by building the GHSEC composition (GHSEC plus excipients) up on a seed core (such as a non-pareil seed) by an active compound-layering technique such as powder coating or by applying the GHSEC composition by spraying a solution or dispersion of GHSEC in an appropriate binder solution onto seed cores in a fluidized bed such as a Wurster coater or a rotary processor. An example of a suitable composition and method is to spray a dispersion of a GHSEC/hydroxypropylcellulose composition in water.

A preferred method for manufacturing the multiparticulate cores of this embodiment is the extrusion/spheronization process, as previously discussed for matrix multiparticulates. A preferred process and composition for this method involves using water to wet-mass a blend of about 5 to about 99% of microcrystalline cellulose with correspondingly about 95 to about 1% GHSEC. Especially preferred is the use of about 95 to about 50% microcrystalline cellulose with correspondingly about 5 to about 50% GHSEC.

A preferred process for making multiparticulate cores of this embodiment is the rotary-granulation process, as previously discussed for matrix multiparticulates.

Another preferred process for making multiparticulate cores of this embodiment is the melt-congeal process, as previously discussed for matrix multiparticulates.

Another preferred process for making multiparticulate cores of this embodiment is the process of coating seed cores with GHSEC and optionally other excipients, as previously discussed for matrix multiparticulates.

A sustained release coating as is known in the art, especially polymer coatings, may be employed to fabricate the membrane, as previously discussed for reservoir systems. Suitable and preferred polymer coating materials, equipment, and coating methods also include those previously discussed.

The rate of GHSEC release from the coated multiparticulates can also be controlled by factors such as the composition and binder content of the active compound-containing core, the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials. A useful series of coatings comprises mixtures of water-insoluble and water-soluble polymers, for example, ethylcellulose and hydroxypropyl methylcellulose, respectively. A particularly useful modification to the coating is the addition of finely-divided water-soluble material, such as sugars or salts. When placed in an aqueous medium, these water soluble membrane additives are leached out of the membrane, leaving pores that facilitate delivery of the active compound. The membrane coating may also be modified by the addition of plasticizers, as is known to those skilled in the art. A particularly useful variation of the membrane coating utilizes a mixture of solvents chosen such that as the coating dries, a phase inversion takes place in the applied coating solution, resulting in a membrane with a porous structure.

A preferred embodiment is a multiparticulate with cores comprising about 1 to about 50% GHSEC and about 10 to about 70% of one or more of the following: microcrystalline cellulose, lactose, mannitol, glyceryl behenate, stearyl alcohol, microcrystalline wax, PVP, HPC and HPMC. The individual cores are coated with either an aqueous dispersion of ethyl cellulose, which dries to form a continuous film, or a film of cellulose acetate containing PEG, sorbitol or glycerol as a release-modifying agent.

A third class of GHSEC sustained-release dosage forms includes the osmotic delivery devices or "osmotic pumps" as they are known in the art. Osmotic pumps comprise a core containing an osmotically effective composition surrounded by a semipermeable membrane. The term "semipermeable" in this context means that water can pass through the membrane, but solutes dissolved in the core permeate through the membrane at a rate significantly slower than water. In use, when placed in an aqueous environment, the device imbibes water due to the osmotic activity of the core composition. Owing to the semipermeable nature of the surrounding membrane, the contents of the device (including the active compound and any excipients) cannot pass through the non-porous regions of the membrane and are driven by osmotic pressure to leave the device through an opening or passageway pre-manufactured into the dosage form or, alternatively, formed in situ in the GI tract as by the bursting of intentionally-incorporated weak points in the coating under the influence of osmotic pressure, or alternatively, formed in situ in the GI tract by dissolution and removal of water-soluble porosigens incorporated in the coating. The osmotically effective composition includes water-soluble species that generate a colloidal osmotic pressure, and water-swellable polymers. The active compound itself (if highly water-soluble) may be an osmotically effective component of the mixture. 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, having solubility in excess of 150 mg/ml, can provide an osmotic pressure of about 4 atmospheres, enough to contribute some osmotic driving force. Because this GHSEC is a base, its solubility is generally higher at acidic pH. Therefore, the osmotic effectiveness of the GHSEC is aided by presence of acidic buffers in the formulation. The active compound composition may be separated from the osmotically effective components by a movable partition or piston.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those that spontaneously form one or more exit passageways, either during manufacturing or when placed in an environment of use. These preferred materials comprise porous polymers, the pores of which are formed by phase inversion during manufacturing, as described below, or by dissolution of a water-soluble component present in the membrane.

A class of materials that have particular utility for forming semipermeable membranes for use in osmotic delivery devices is that of porous hydrophobic polymers or vapor-permeable films, as disclosed by U.S. Pat. No. 5,827,538. These materials are highly permeable to water, but highly impermeable to solutes dissolved in water. These materials owe their high water permeability to the presence of numerous microscopic pores (i.e., pores that are much larger than molecular dimensions). Despite their porosity, these materials are impermeable to molecules in aqueous solution because liquid water does not wet the pores. Water in the vapor phase is easily able to pass across membranes made from these materials. Such membranes are also known as vapor-permeable membranes.

A preferred embodiment of this class of osmotic delivery devices consists of a coated bi-layer tablet. The coating of such a tablet comprises a membrane permeable to water but substantially impermeable to GHSEC and excipients contained within. The coating contains one or more exit passageways in communication with the GHSEC-containing layer for delivering the GHSEC. The tablet core consists of two layers: one layer containing the GHSEC composition (including optional osmotic agents and hydrophilic water-soluble polymers) and another layer consisting of a water-swellable material, with or without additional osmotic agents.

When placed in an aqueous medium, the tablet imbibes water through the membrane, causing the GHSEC composition to form a dispensible aqueous composition, and causing the swellable layer to expand and push against the GHSEC composition, forcing the GHSEC composition out of the exit passageway. The GHSEC composition can swell aiding in forcing the GHSEC out the passageway. GHSEC can be delivered from this type of delivery system either dissolved or dispersed in the composition forced out of the exit passageway.

The rate of GHSEC delivery is controlled by such factors as the permeability and thickness of the coating, the osmotic pressure of the GHSEC-containing layer, the water activity of the swellable layer, and the surface area of the device. Those skilled in the art will appreciate that increasing the thickness of the coating will reduce the release rate, whereas increasing the permeability of the coating or the water activity of the hydrogel layer or the osmotic pressure of the GHSEC-containing layer or the surface area of the device will increase the release rate.

Exemplary materials that are useful to form the GHSEC composition, in addition to the GHSEC itself, include HPMC, PEO, and PVP, and other pharmaceutically-acceptable carriers. In addition, osmotic agents such as sugars or salts, especially sucrose, lactose, mannitol, or sodium bitartrate, may be added. Materials that are useful for forming the swelling layer include sodium carboxymethyl cellulose, poly(ethylene oxide), poly(acrylic acid), sodium (poly-acrylate), hydroxypropylmethylcellulose (HPMC), hydroxypropylcellulose (HPC), and other high molecular-weight hydrophilic materials. In addition, osmagents such as sugars or salts may be added. Particularly useful are poly(ethylene oxide)s having a molecular weight from about 5,000,000 to about 7,500,000.

Materials that are useful for forming the coating are cellulose esters, cellulose ethers, and cellulose ester-ethers. Preferred are cellulose acetate and ethylcellulose and optionally with PEG included as permeability modifying component.

The exit passageway must be located on the side of the tablet containing the GHSEC composition. There may be more than one such exit passageway. The exit passageway may be produced by mechanical means or by laser drilling, or by creating a difficult-to-coat region on the tablet by use of special tooling during tablet compression or by other means. The rate of GHSEC delivery from the device may be optimized so as to provide a method of delivering GHSEC to a mammal for optimum therapeutic effect.

Osmotic systems can also be made with a homogeneous core surrounded by a semipermeable membrane coating. GHSEC can be incorporated into a tablet core that also contains other excipients that provide sufficient osmotic driving force and optionally solubilizing excipients such as acids. A semipermeable membrane coating can be applied via conventional tablet-coating techniques such as using a pan coater. An active compound-delivery passageway can then be formed in this coating by drilling a hole in the coating, either by use of a laser or other mechanical means. Alternatively, the passageway may be formed by rupturing a portion of the coating or by creating a region on the tablet that is difficult to coat, as described above.

The core can consist of one or more pharmaceutically active compounds, water-soluble compounds for inducing osmosis, non-swelling solubilizing agents, non-swelling (water-soluble or water-insoluble) wicking agents, swellable hydrophilic polymers, binders and lubricants.

The osmotically active (water-soluble) agent is typically a sugar alcohol such as mannitol or sorbitol, or sugars in combination with polysaccharides such as dextrose and maltose, or a physiologically tolerable ionic salt that is compatible with the other components such as sodium or potassium chloride. Another osmotic agent is urea. Examples of water-soluble compounds for inducing osmosis are: inorganic salts such as magnesium chloride or magnesium sulfate, lithium, sodium or potassium chloride, lithium, sodium or potassium hydrogen or dihydrogen phosphate, salts of organic acids such as sodium or potassium acetate, magnesium succinate, sodium benzoate, sodium citrate or sodium ascorbate; carbohydrates such as sorbitol or mannitol (hexite), arabinose, dextrose, ribose or xylose (pentosene), glucose, fructose, galactose or mannose (hexosene), sucrose, maltose or lactose (disaccharides) or raffinose (trisaccharides); water-soluble amino acids such as glycine, leucine, alanine or methionine, urea and the like, and mixtures thereof. These water-soluble excipients may be present in the core in amounts by weight of about 0.01 to about 45%, based on the total weight of the therapeutic system.

Non-swelling solubilizing agents include (a) agents that inhibit crystal formation of the active agent or otherwise act by complexation therewith; (b) high HLB (hydrophilic-lipophilic balance) micelle-forming surfactants, particularly non-ionic and/or anionic surfactants: (c) citrate esters; and combinations thereof, particularly combinations of complexing agents and anionic surfactants. Examples of agents that inhibit crystal formation of the active agent or otherwise acts by complexation therewith include polyvinylpyrrolidone, polyethyleneglycol (particularly PEG 8000), cyclodextrins and modified cyclodextrins. Examples of high HLB, micelle forming surfactants include Tween 20, Tween 60, Tween 80, polyoxyethylene or polyethylene-containing surfactants, or other long chain anionic surfactants, particularly sodium lauryl sulfate. Examples of citrate ester derivatives that are preferred are the alkyl esters, particularly triethyl citrate. Combinations of these that are particularly preferred are polyvinylpyrrolidone with sodium lauryl sulfate and polyethyleneglycol with sodium lauryl sulfate.

Non-swelling wicking (wetting) agents are used to create channels or pores in the core of the tablet. This facilitates channeling of water through the core by physisorption. Preferred wicking agents do not swell to any appreciable degree. These materials can be water soluble or water insoluble materials. Water-soluble materials suitable for acting as wicking (wetting) agents include surface-active compounds, i.e., surfactants, e.g., anionic surfactants of the alkylsulfate type such as sodium, potassium or magnesium lauryl sulfate, n-tetradecylsulfate, n-hexadecyl sulfate or n-octadecylsulfate; of the alkyl ether sulfate type, e.g., sodium, potassium or magnesium n-dodecyloxyethyl sulfate, n-tetradecyloxyethyl sulfate, n-hexadecyloxethyl sulfate or n-octadecyloxyethyl sulfate; or of the alkylsulfonate type, e.g. sodium potassium or magnesium n-dodecanesulfonate, n-tetradecanesulfonate, n-hexadecanesulfonate or n-octadecanesulfonate. Further suitable surfactants are nonionic surfactants of the fatty acid polyhydoxy alcohol ester type such as sorbitan monolaurate, sorbitan tristerate or triolate, polyethylene glycol fatty acid ester such as polyoxyethyl stearate, polyethylene glycol 400 stearate, polyethylene glycol 2000 stearate, preferably polyethylene oxide/propylene oxide block copolymers of the Pluronic® (BASF, Parsippany, N.J.) or Synperonic® (ICI Surfactants, Everberg, Belgium) type, polyglycerol-fatty acid esters or glyceryl-fatty acid esters. Especially suitable is sodium lauryl sulfate. When present, these surfactants should be preferable present from about 0.2 to about 2% based on the total core weight. Other soluble wicking (wetting) agents include low molecular weight polyvinyl pyrrolidone and m-pyrol.

Insoluble materials suitable for acting as wicking (wetting) agents include, but are not limited to, colloidal silicon dioxide, kaolin, titanium dioxide, fumed silicon dioxide, alumina, niacinamide, bentonite, magnesium aluminum silicate, polyester, polyethylene. Particularly suitable insoluble wicking agents include colloidal silicon dioxide.

Suitable wall materials for forming the semi-permeable wall include microporous materials described in U.S. Pat. Nos. 3,916,899 and 3,977,404. It is possible to use acylated cellulose derivatives (cellulose esters) which are substituted by one to three acetyl groups or by one or two acetyl groups and a further acyl other than acetyl, e.g., cellulose acetate, cellulose triacetate, agar acetate, amylose acetate, beta glucan acetate, beta glucan triacetate, ethyl cellulose, cellulose acetate ethyl carbamate, cellulose acetate phthalate, cellulose acetate methyl carbamate, cellulose acetate succinate, cellulose acetate dimethylaminoaceate, cellulose acetate ethyl carbonate, cellulose acetate chloroacetate, cellulose acetate ethyl oxalate, cellulose acetate methylsulfonate, cellulose acetate butyl sulfonate, cellulose acetate propionate, cellulose acetate octate, cellulose acetate laurate, cellulose acetate p-toluenesulfonate, cellulose acetate butyrate, and other cellulose acetate derivatives. Suitable semi-permeable membrane materials are also triacetate of locust bean gum, methyl cellulose, hydroxypropyl methylcellulose and polymeric epoxides, copolymers of alkylene oxides, poly(vinyl methyl) ether polymers and alkyl glycidyl ethers, polyglycols or polylactic acid derivatives and further derivatives thereof. It is also possible to use mixtures of insoluble polymers, which when coated form a semi-permeable film, e.g. water insoluble acrylates, e.g., the copolymer of ethyl acrylate and methyl methacrylate.

A second, water-soluble component can be added to increase the permeability of the coating. Preferred water-soluble components are $C_2$–$C_4$ alkylene glycol, preferably polyethylene glycol.

An embodiment of GHSEC sustained release osmotic dosage forms of this invention comprises an osmotic GHSEC-containing tablet, which is surrounded by an asymmetric membrane, where said asymmetric membrane possesses one or more thin dense regions in addition to less dense porous regions. This type of membrane, similar to those used in the reverse-osmosis industry, generally allows higher osmotic fluxes of water than can be obtained with a dense membrane. When applied to a active compound formulation, e.g., a tablet, an asymmetric membrane allows high active compound fluxes and well-controlled sustained active compound release. This asymmetric membrane comprises a semipermeable polymeric material, that is, a material which is permeable to water, and substantially impermeable to salts and organic solutes such as a GHSEC.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those which spontaneously form one or more exit passageways, either during manufacturing or when placed in an environment of use. These preferred materials comprise porous polymers, the pores of which are formed by phase inversion during manufacturing, as described above, or by dissolution of a water-soluble component present in the membrane.

The asymmetric membrane is formed by a phase-inversion process. The coating polymer, e.g., ethylcellulose or cellulose acetate, is dissolved in a mixed solvent system comprising a mixture of solvents (e.g., acetone) and non-solvents (e.g., water) for the ethylcellulose or cellulose acetate. The components of the mixed solvent are chosen such that the solvent (e.g., acetone) is more volatile than the non-solvent (e.g., water). When a tablet is dipped into such a solution, removed and dried, the solvent component of the solvent mixture evaporates more quickly than the non-solvent. This change in solvent composition during drying causes a phase-inversion, resulting in precipitation of the polymer on the tablet as a porous solid with a thin dense outer region. This outer region possesses multiple pores through which active compound delivery can occur.

In a preferred embodiment of an asymmetric membrane-coated tablet, the polymer/solvent/non-solvent mixture is sprayed onto a bed of tablets in a tablet-coating apparatus such as a HCT-30 tablet coater (Vector Corporation, Marion, Iowa).

In the environment of use, e.g., the GI tract, water is imbibed through the semipermeable asymmetric membrane into the tablet core. As soluble material in the tablet core dissolves, an osmotic pressure gradient across the membrane builds. When the hydrostatic pressure within the membrane enclosed core exceeds the pressure of the environment of use (e.g., the GI lumen), the GHSEC-containing solution is "pumped" out of the dosage form through preformed pores in the semipermeable membrane. The constant osmotic pressure difference across the membrane results in a constant well-controlled delivery of GHSEC to the use environment. A portion of the GHSEC dissolved in the tablet also exits via diffusion.

In this asymmetric-membrane-coated GHSEC tablet embodiment, high solubility salts of GHSEC are preferred. Also preferred are the inclusion of one or more solubilizing excipients, ascorbic acid, erythorbic acid, citric acid, fumaric acid, succinic acid, tartaric acid, sodium bitartrate, glutamic acid, aspartic acid, partial glycerides, glycerides, glyceride derivatives, polyethylene glycol esters, polypropylene glycol esters, polyhydric alcohol esters, polyoxyethylene ethers, sorbitan esters, polyoxyethylene sorbitan esters, saccharide esters, phospholipids, polyethylene oxide-polypropylene oxide block co-polymers, and polyethylene glycols. Most preferred are solubilizing excipients fumaric acid, ascorbic acid, succinic acid, and aspartic acid.

Osmotic tablets can also be made with a core tablet containing osmogents and/or solubilizing excipients surrounded first by a active compound containing layer and then second a semipermeable coating. The core tablet containing osmotic agents and/or solubilizing excipients can be made by standard tabletting methods known in the pharmaceutical industry. The semipermeable coating can then be applied to the layered core by many processes known in the art such as spray-coating or dip-coating methods described previously in these specifications. The active compound containing layer may be applied around the core by spray-coating methods where a solution or slurry of active compound and excipients is coated onto the tablet core. The active compound and excipients may also be layered around the tablet core by making a "layered" type of configuration using a tablet press to form a second active compound-containing layer around the tablet core. This type of compression coating method can be used to apply a powder coating (without solvents) around a tablet core.

Another embodiment of sustained release GHSEC osmotic dosage forms of this invention consists of GHSEC multiparticulates coated with an asymmetric membrane. GHSEC-containing multiparticulates are prepared by, for example, extrusion/spheronization or fluid bed granulation, or by coating non-pareil seeds with a mixture of GHSEC and a water-soluble polymer, as described above. GHSEC-containing multiparticulates are then spray-coated with a solution of a polymer in a mixture of a solvent and a non-solvent, as described above, to form asymmetric-membrane-coated multiparticulates. This spray-coating operation is preferably carried out in a fluid bed coating apparatus, e.g., a Glatt GPCG-5 fluid bed coater (Glatt Air Techniques, Inc., Ramsey, N.J.). The polymer used for forming the semipermeable asymmetric membrane is chosen as described above for asymmetric-membrane coated tablets. Likewise, excipients for the multiparticulate cores can be chosen as described above for asymmetric-membrane coated tablets.

Osmotic capsules can be made using the same or similar components to those described above for osmotic tablets and multiparticulates. The capsule shell or portion of the capsule shell can be semipermeable and made of materials described above. The capsule can then be filled either by a powder or liquid comprising GHSEC, excipients that provide osmotic potential, and optionally solubilizing excipients. The capsule core can also be made such that it has a bilayer or multilayer composition analogous to the bilayer tablet described above.

A fourth class of GHSEC sustained release dosage forms of this invention comprises coated swellable tablets and multiparticulates, as described in co-pending commonly assigned U.S. application Ser. No. 07/296,464, filed Jan. 12, 1989 (published as EP 378404 A2; Jul. 7, 1990). Coated swellable tablets comprise a tablet core comprising GHSEC and a swelling material, preferably a hydrophilic polymer, coated with a membrane that contains holes or pores through which, in the aqueous use environment, the hydrophilic polymer can extrude and carry out the GHSEC. Alternatively, the membrane may contain polymeric or low molecular weight water soluble porosigens which dissolve in the aqueous use environment, providing pores through which the hydrophilic polymer and GHSEC may extrude. Examples of porosigens are water-soluble polymers such as hydroxypropylmethylcellulose, and low molecular weight compounds like glycerol, sucrose, glucose, and sodium chloride. In addition, pores may be formed in the coating by drilling holes in the coating using a laser or other mechanical means. In this fourth class of GHSEC sustained release dosage forms, the membrane material may comprise any film-forming polymer, including polymers which are water permeable or impermeable, provided that the membrane deposited on the tablet core is porous or contains water-soluble porosigens or possesses a macroscopic hole for water ingress and GHSEC release. Multiparticulates (or beads) may be similarly prepared, with a GHSEC/swellable material core, coated by a porous or porosigen-containing membrane. Embodiments of this fourth class of GHSEC sustained release dosage forms may also be multilayered, as described in EP 378 404 A2.

Sustained release formulations may also be prepared with a portion of the dose released initially rapidly, followed by sustained release of the remaining portion of the dose.

Formulations that release a portion of the dose as a bolus shortly after administration and then release the remaining portion of the dose at a sustained release rate over time, such as over 2 hours to 18 hours or longer, can be made by a variety of methods. For example, a bilayer tablet can be formed with one layer having a sustained release matrix and the other layer an immediate release composition. Upon ingestion, the immediate release layer disintegrates leaving only the matrix tablet to provide sustained release. In another example, a drug coating can be applied over a matrix or osmotic tablet or over sustained release multiparticulates. The coating can be applied using typical coating equipment standard to the pharmaceutical industry. The active compound can either be a solution or in suspension and is typically mixed with a water soluble polymer in the coating solution. In addition, a combination dosage form can be made by mixing sustained release multiparticulates and immediate release multiparticulates in one dosage form. A preferred method of making a formulation that has an immediate release component and a controlled-release component is to apply a compression coating around an osmotic tablet.

Osmotic tablets comprise a tablet core that contains active compound and may contain excipients that have an osmotic potential greater than the fluid in the environment of use or contain water swellable materials. The tablet cores are surrounded by a semipermeable coating that allows water to be imbibed into the tablet core. In operation it is important that this semipermeable coating remain intact, if the coating is cracked or disrupted dose dumping could occur or the release rate could significantly increase. A compression coating is made by compressing a powder granulation around a tablet core to form a outer layer or coating. This is done in specialized tablet presses where the inner core is place in the powder/granulation during the compression step. Applying an immediate release active compound layer around an osmotic tablet core can be done without cracking or disrupting the semipermeable coating and thus, without affecting the release rate from the osmotic tablet within the compression coating.

Compression coatings can be successfully applied with the following parameters, the weight ratio of powder/granulation in the compression layer to the osmotic tablet ranging from about 1 to about 2; a tablet compression force ranging from about 5 to about 30 kP; a semipermeable osmotic coating at least 8 wt % on the osmotic tablet cores; and active compound loading in the compression layer ranging from about 0.1 wt % to about 40 wt %. Compression coatings can be applied to coated osmotic tablets using a conventional compression coating tablet press such as a Kilian RUD Press manufactured by Kilian and Company, Inc., Horsham, Pa. Preferred excipients for application of compression coating are about 25 to about 98.5 wt % microcrystalline cellulose, about 0 to about 75 wt % lactose, about 0 to about 25 wt % hydroxypropyl methyl cellulose or polyvinyl pyrrolidone, and less than about 2% of a lubricant such as magnesium stearate. A preferred range of weight ratio of powder/granulation in the compression layer to the coated osmotic tablet is about 5/4 to about 7/4. A preferred range of tablet compression force is about 10 to about 25 kP. It is preferred that the semipermeable coating be at least 10 wt % of the uncoated osmotic tablet core weight.

Combination immediate release and sustained release formulations comprising a compression coating surrounding a coated osmotic tablet can be tested to show that the compression coating has been successfully applied to the tablet without affecting release rates from the coated osmotic tablet. The compression-coated formulations can be tested in standard dissolution tests. The release rate from the coated osmotic tablet would be considered not changed after compression coating if the release rates before and after compression coating are within 80% and 125% of each other (i.e., the release rate of compression coated osmotic tablet is within 80% to 125% of the release rate of the osmotic tablet prior to compression coating). For example, for the same amount of time that 50% of the active compound from the osmotic tablet is released, active compound release from the compression coated tablets should be within 40% and 62.5%.

A growth hormone secretagogue can be administered to a patient as a pharmaceutically acceptable salt or as a prodrug. The terms pharmaceutically acceptable salt or prodrug mean the salts or prodrugs of a growth hormone secretagogue that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of a growth hormone secretagogue. Such salts can be prepared in situ during the final isolation and purification of a compound, or by separately reacting a purified compound with a suitable organic or inorganic acid or base, as required, and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977).

The term "prodrug" means a compound that is transformed in vivo to yield a growth hormone secretagogue. The transformation may occur by various mechanisms, such as through hydrolysis in blood. A discussion of the use of prodrugs is provided by T. Higuchi and W. Stella, "Proactive compounds as Novel Delivery Systems," Vol. 14 of the A.C.S. *Symposium Series*, and in *Bioreversible Carriers in Active compound Design*, ed. Edward B. Roche, American Pharmaceutical Association and Pergamon Press, 1987.

For example, if a growth hormone secretagogue contains a carboxylic acid functional group, a prodrug can comprise an ester formed by the replacement of the hydrogen atom of the acid group with a group such as $(C_1-C_8)$alkyl, $(C_2-C_{12})$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonloxy)ethyl having from 5 to 8 carbon atoms, N-(alkoxycarbonyl)aminomethyl having from 3 to 9 carbon atoms, 1-(N-alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a growth hormone secretagogue comprises an alcohol functional group, a prodrug can be formed by the replacement of the hydrogen atom of the alcohol group with a group such as $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a growth hormone secretagogue comprises an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$ cycloalkyl, or benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is (($C_1-C_6$)alkyl, carboxy $(C_1-C_6)$alkyl, amino$(C_1-C_4)$alkyl or mono-N- or di-N,N—$(C_1-C_6)$alkylaminoalkyl, —C(Y$_2$) Y$_3$ wherein Y$_2$ is H or methyl and Y$_3$ is mono-N- or di-N,N—$(C_1-C_6)$alkylamino, morpholino, piperidin-1-yl or pyrrolidin-1-yl.

A growth hormone secretagogue may contain asymmetric or chiral centers, and therefore, exist in different stereoisomeric forms. It is contemplated that all stereoisomeric forms of a growth hormone secretagogue as well as mixtures thereof, including racemic mixtures, form part of the present invention. In addition, the present invention contemplates all geometric and positional isomers. For example, if a growth hormone secretagogue contains a double bond, both the cis and trans forms, as well as mixtures, are contemplated.

Mixtures of isomers, including stereoisomers can be separated into their individual components on the basis of their physical chemical differences by methods well know to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

A growth hormone secretagogue may exist in unsolvated as well as solvated forms with pharmaceutically acceptable solvents such as water, ethanol, and the like. The present invention contemplates and encompasses both the solvated and unsolvated forms.

It is also possible that a growth hormone secretagogue may exist in different tautomeric forms. All tautomers of a growth hormone secretagogue are contemplated. For example, all of the tautomeric forms of the imidazole moiety are included in this invention. Also, for example, all keto-enol and/or imine-enamine forms of a growth hormone secretagogue are included in this invention. Those skilled in the art will recognize that any compound names contained herein may be based on a particular tautomer of a compound. While the name for only a particular tautomer may be used, it is intended that all tautomers are encompassed by the name of the particular tautomer and all tautomers are considered part of the present invention.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Growth hormone secretagogues that contain the aforementioned isotopes and/or other isotopes of other atoms are within the scope of this invention. Certain isotopically-labelled growth hormone secretagogues, for example those into which radioactive isotopes such as $^3H$ and $^{14}C$ are incorporated, are useful in active compound and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

The documents cited herein, including patents and patent applications, are all hereby incorporated by reference.

The examples presented below are intended to illustrate particulate embodiments of the invention and are not intended to limit the specification, including the claims, in any manner.

EXAMPLES

Example 1

Clinical Study

Study Population

This clinical study was performed in male and female subjects between the ages of 65 and 84 years inclusive, and whose baseline IGF-1 levels were <150 ng/ml.

Dosing Regimen

The study was a double blind, parallel group, placebo-controlled study.

In the first leg of the study, the safety and efficacy of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate was studied in 4 groups of approximately 24 subjects at doses of 0 mg (placebo), 1 mg tid, 3 mg tid and 3 mg am and 6 mg pm. (All dosage forms in this part of the study were immediate release dosage forms.)

In addition, an extension study was conducted to evaluate the relationship between peak GH concentrations or IGF-I versus surrogate responses such as lipid concentrations and body composition. A sustained release (SR) formulation was also evaluated, either alone or combined with an immediate release (IR) formulation (24–30 patients per group). [16 mg (10 SR, 6 IR) h.s. (h.s. means at bedtime); 16 mg (10 SR, 6 IR) h.s. every third day; 16 mg SR h.s.; and placebo.] The formulations are set forth below.

Study Active Compound Administration

In the extension study, 2-amino-N-[2-(3a-(R)-benzyl-2-methyl-3-oxo-2,3,3a ,4,6,7-hexahydro-pyrazolo[4,3-c]pyridin-5-yl)-1-(R)-benzyloxymethyl-2-oxo-ethyl]-isobutyramide L-tartrate was supplied as 10 mg or 3 mg sustained release tablets and 3 mg immediate release tablets, with matching placebo tablets. Study active compound was supplied in blisterpaks, with five tablets to be taken at time of each dosing. Subjects were instructed to take the tablets with one glass of water at bedtime.

Plan and Design

Return visits were scheduled at 1, 2, and 4 weeks after baseline. A blood sample for 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and IGF-1 levels was obtained at each visit. The baseline and all subsequent follow-up visits were performed at the same time of day (between approximately 8–11 am).

In addition to this schedule, subjects at selected sites in the extension study were studied during two overnight admissions on the first night of dosing and again on day 28 of dosing. Growth hormone secretion and pharmacokinetic sampling was carried out.

Follow-up Period and End of Study

A follow-up evaluation was made at 1, 2, and 4 weeks. Vital signs were obtained and the skin of the face, trunk and upper extremities was inspected. A blood sample was obtained for measurement of GH and IGF-1, and for measurement of plasma concentrations of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate.

In addition, subjects at selected study centers were admitted to an overnight unit on day 28 of dosing. Growth hormone secretion profile, pharmacokinetics, and vital sign determination were carried out.

Efficacy Endpoints

The primary efficacy endpoint was the percentage change from baseline in IGF-1. Secondary outcomes included insulin-like growth factor binding protein 3 (IGFBP-3), cholesterol subfractions, and percent changes in total adipose and total lean tissue. Changes in each of the secondary efficacy measures over time were examined systematically either graphically or in tabular form and summarized using appropriate descriptive statistics as is well known in the art.

Results

In the first leg of the study, there was a dose related increase in IGF-I, with both groups administered 9 mg daily having similar increases of approximately 35%. IGFBP3 also increased. There were small changes in body composition consistent with increased GH secretion, i.e., decreased adipose tissue and increased apparent whole body lean mass.

In the extension study, there were increases in IGF-I in each of the 2 groups in which 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate was dosed daily. The group randomized to receive 2-amino-N-[2-(3aR-benzyl-2-methyl-3-oxo-2,3,3a,4,6,7-hexahydro-pyrazolo[4,3-c]pyridin-5-yl)-1R-benzyloxymethyl-2-oxo-ethyl]-isobutyramide L-tartrate every third day had a minimal average rise of IGF-I of approximately 10%. The group receiving SR alone had modest and sporadic GH peaks averaging less than 4 ng/ml at baseline and 2 ng/ml after 4 weeks. The groups receiving 6 mg IR (with 10 mg SR) had GH peaks at baseline averaging 15 ng/ml or more, which by 4 weeks had attenuated to 4–6 ng/ml. By a variety of analyses, there was less attenuation in the group receiving Q 3 day 2-amino-N-[2-(3a-(R)-benzyl-2-methyl-3-oxo-2,3,3a, 4,6,7-hexahydro-pyrazolo[4,3-c]pyridin-5-yl)-1R- benzyloxymethyl-2-oxo-ethyl]-isobutyramide L-tartrate. The Q 3 day group had peak heights on average 1.52 ng/ml greater than the QD group. Changes in body composition were again observed and were similar in the two groups receiving IR formulation despite large differences in the increase of IGF-I. Increases in lean tissue approximated 0.5–0.6% with corresponding reductions in adipose tissue.

The specific dosage forms used in the clinical study are set forth below wherein the active compound is 2-amino-N-[2-(3a-(R)-benzyl-2-methyl-3-oxo-2,3,3a,4,6,7-hexahydro-pyrazolo[4,3-c]pyridin-5-yl)-1R-benzyloxymethyl-2-oxo-ethyl]-isobutyramide L-tartrate.

| Component | Grade of Component | Weight (mg/tablet) |
|---|---|---|
| 1 mg immediate release tablet | | |
| Active compound | Pharmaceutical | 1.30[a] |
| Calcium phosphate dibasic, anhydrous | USP | 35.08 |
| Microcrystalline cellulose (Avicel ® PH102; FMC Corporation, Philadelphia, PA) | NF | 56.12 |
| Sodium starch glycolate (Explotab; Penwalt, Patterson, NJ) | NF | 5.00 |
| Magnesium stearate | NF | 1.50 |
| 3 mg immediate release tablet | | |
| Active compound | Pharmaceutical | 3.89[a] |
| Calcium phosphate dibasic, anhydrous | USP | 34.79 |
| Microcrystalline cellulose (Avicel ® PH 102) | NF | 54.82 |
| Sodium starch glycolate (Explotab) | NF | 5.00 |
| Magnesium stearate | NF | 1.50 |
| 3 mg sustained release tablet | | |
| Active compound | Pharmaceutical | 3.89[a] |
| Mannitol 2080, granular form | USP | 34.00 |
| Fumaric acid | NF | 12.00 |
| Microcrystalline cellulose | NF | 48.61 |
| Magnesium stearate (1st addition) | NF | 0.50 |
| Magnesium stearate (2nd addition) | NF | 1.00 |
| Cellulose acetate (CA-398-10) Eastman Chemical, Kingsport, TN | NF | 11.90 |
| Polyethylene glycol (Carbowax PEG 3350; Union Carbide, Charleston, WV) | NF | 5.10 |
| Purified water[b] | USP | (35.70) |
| Acetone[b] | NF | (117.30) |
| 10 mg sustained release tablet | | |
| Active compound | Pharmaceutical | 12.97[a] |
| Mannitol 2080, granular form | USP | 113.32 |
| Fumaric acid | NF | 40.00 |
| Microcrystalline cellulose (Avicel PH102) | NF | 162.01 |
| Magnesium stearate (1st addition) | NF | 1.67 |
| Magnesium stearate (2nd addition) | NF | 3.33 |
| Cellulose acetate (CA-398-10) Eastman Chemical, Kingsport, TN | NF | 33.00 |

-continued

| Component | Grade of Component | Weight (mg/tablet) |
|---|---|---|
| Polyethylene glycol (Carbowax PEG 3350) Union Carbide, Charleston, WV | NF | 22.00 |
| Purified water[b] | USP | (126.50) |
| Acetone[b] | NF | (368.50) |

[a]Based on a theoretical active compound substance potency of 77.1%.
[b]The purified water and acetone are volatile and are not present in the final dosage form.

In the 3 mg and 10 mg sustained release dosage forms, the active compound, mannitol, fumaric acid, microcrystalline cellulose, and magnesium stearate are tablet core components.
NF is National Formulary.
USP is United States Pharmacopoeia.
Preparation of 10 mg and 3 mg Sustained Release Dosage Forms This example illustrates a method for making formulations of 3 mg and 10 mg osmotic tablets comprising a tablet core containing active compound surrounded by a semi-permeable asymmetric membrane coating. The processing of the core tablet comprised (1) blending of core components, except for magnesium stearate; (2) milling and reblending the same components; (3) adding and blending a portion of the magnesium stearate; (4) dry granulating; (5) milling/screening and reblending; (6) adding and blending the remaining portion of magnesium stearate; (7) compressing core tablets; (8) spraying an asymmetric membrane coating on the core tablets; and (9) drying.

In batch sizes of 6–14 kilograms, 2-amino-N-[2-(3aR-benzyl-2-methyl-3-oxo-2,3,3a,4,6,7-hexahydro-pyrazolo[4,3-c]pyridin-5-yl)-1R-benzyloxymethyl-2-oxo-ethyl]-isobutyramide L-tartrate was blended with all other components except magnesium stearate for 30 minutes in a suitable sized stainless steel twin-shelled blender (16 quart to 2 cubic feet). Next, the blend was passed through a mill (Fitz model JT or D mill fitted with #1A plate, medium speed, knives forward, The Fitzpatrick Company, Elmhurst, Ill.) and blended again for 30 minutes. Then, magnesium stearate (1st addition) was added and blended for 5 minutes. The partially lubricated blend was dry granulated using a roller compactor (Freund TF-156 roller compacter, Freund Industrial Co., Tokyo, Japan) with auger screw feed of 10–12 rpm, pressure 25 kg/cm$^2$, and roller speed of 12 rpm. The roller compactor was fitted with an oscillating roller granulator screen size of 20 mesh to mill the compacted ribbons. Next, the granulation was blended for 30 minutes before the last portion of magnesium stearate (2nd addition) was added and reblended for 5 minutes. Using a conventional tablet press (Kilian LX21, Kilian and Co., Inc, Horsham, Pa.), the final blend was compressed into tablets.

A semi-permeable membrane coating (as described in U.S. Pat. No. 5,612,059 entitled Use of Asymmetric Membranes in Delivery Devices) was applied to these tablets using a HCT-30 explosion-proof pan coater (Vector Corporation, Marion, Iowa) operated at a spray rate of 20 grams per minute, an inlet temperature of 40–45° C. and air flow rate of 30 cfm (14158.43 cm$^3$/sec). The asymmetric membrane coating formulations applied to the 3 mg and 10 mg core tablet released 80% of the dose in 10–12 hours in simulated gastric fluid (sgn) at pH about 1.2, which procedure is well known and disclosed in USPXXIII. The coating for the 3 mg tablets consisted of cellulose acetate/ polyethylene glycol/water/acetone ratios of 7/13/21/69 (w/w) coated to an increase in the initial weight of 17 weight %. Likewise, for the 10 mg tablet, the coating was composed of 6/4/23/67 formulation applied to 15.5 weight %. The coated tablets were dried in the coater for 15 minutes at an inlet temperature set point of 60° C. and dried in an oven (Gruenberg solvent tray oven, Gruenberg Oven Company, Williamsport, Pa.) for 16 hours at 50° C. before testing for dissolution performance. After drying, the weight of the applied coating material was determined based on a percentage of the initial core tablet weight.

Preparation of 1 mg and 3 mg Immediate Release Dosage Forms

1. Blend calcium phosphate dibasic anhydrous, microcystalline cellulose, and sodium starch glycolate for 5 minutes in an amber glass bottle using a Turbula mixer (WAB, Basel, Switzerland) (20 rpm setting).
2. Screen the excipient mixture from step 1 through a 40 mesh screen and blend for 15 minutes in an amber glass bottle using a Turbula mixer (20 rpm setting).
3. Add growth hormone secretagogue to the excipient mixture from step 2 using geometric dilution. After each dilution, blend for 10 minutes in an amber glass bottle using a Turbula mixer (20 rpm setting).
4. Screen this active blend from step 3 through a 40 mesh screen and blend for 10, 20 and 30 minutes in an amber glass bottle using a Turbula mixer (20 rpm setting). Remove top, middle and bottom samples at each time point.
5. Add 1.0% (before granulation) magnesium stearate and blend for 5 minutes in an amber glass bottle using a Turbula mixer (20 rpm setting).
6. Roller compact the blend using the TF Freund mini roller compactor,
   roll pressure: 40 kg/cm$^2$
   roll speed: 3 rpm
   feed speed: 10 rpm
7. Mill the compacts using the rotating granulator fitted with a 30 mesh screen.
8. Add 0.5% (after granulation) magnesium stearate to the active granulation and blend for 5 minutes in an amber glass bottle using a Turbula mixer (20 rpm setting).
9. Tablet using a single station press (F-Press, Manesty Machines, Liverpool, England).

Alternative Preparation of 1 mg and 3 mg Immediate Release Dosage Forms

1. Blend calcium phosphate dibasic anhydrous, microcystalline cellulose, and sodium starch glycolate in a 4-quart V-blender for 15 minutes.
2. Discharge blender.
3. Add growth hormone secretagogue and an approximately equal volume of excipient blend from step 2 to an amber glass bottle and blend for 15 minutes using a Turbula mixer (20 rpm setting).
4. Place approximately ½ of the excipient blend from step 2 into the V-blender.
5. Pass active compound/excipient blend from step 3 through a 40 mesh screen and place in V-blender. Use a mortar and pestle to reduce the size of any agglomerates that do not pass through the screen.
6. Place the remaining excipient blend from step 2 into the V-blender.
7. Blend in the V-blender for 15 minutes.
8. Pass the blend from step 7 through a Fitzpatrick JT mill fitted with a #1 plate with knives forward and at medium speed (The Fitzpatrick Company, Elmhurst, Ill.).
9. Place the blend from step 8 in the 4-quart V-blender and blend for 15 minutes.
10. Add magnesium stearate (1.0% before granulation) and blend for 5 minutes.
11. Roller compact the blend using a Freund TF-Mini Roller compactor,
    roll pressure: 40 kg/cm$^2$
    feed speed: 12 rpm
    roll speed: 3 rpm
12. Mill the compacts from step 11 using the rotating granulator fitted with a 30 mesh screen.
13. Place the active granulation from step 12 in the 4-quart V-blender and blend for 10 minutes.
14. Add 0.5% (after granulation) magnesium stearate and blend for 15 minutes.
15. Tablet the blend using the Kilian T100 rotary press (Kilian and Company, Inc., Horsham, Pa.).

Example 2

Simulated Sustained Release

The ability of a simulated sustained release formulation of a growth hormone secretagogue such as 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to induce pulsatile release of growth hormone and increase IGF-I responses at 24 hrs was demonstrated in young, healthy male volunteers. This dosing regimen simulates active compound delivery by a sustained release dosage form. The clinical study was designed as a randomized, crossover study administering oral solutions of either a single 10 mg dose of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate as a bolus or a single 3 mg loading dose followed by seven (7) 1 mg maintenance doses every 2 hours for a total dose of 10 mg. Serum concentrations of growth hormone were monitored just prior to administration of the first dose and every 20 minutes thereafter for 24 hours. Serum insulin-dependent growth factor-I (IGF-I) concentrations were measured at 0, 12, and 24 hours post-first dose.

Results indicated that simulated sustained release of 10 mg of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate generally lowered the growth hormone $AUC_{0-24}$ and $C_{max}$, while the frequency and amplitude of secondary GH peaks increased. The IGF-I serum concentration change from baseline at 24 hours was increased following the simulated sustained release dosing compared to the bolus.

Methods

This investigation was conducted as a randomized, crossover study of the safety, toleration, pharmacokinetics and pharmacodynamics of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate in four fasted young, healthy, male volunteers. Each participant received, in a randomized fashion, 2-amino-N-[2-(3a-(R)-benzyl-2-methyl-3-oxo-2,3,3a,4,6,7-hexahydro-pyrazolo[4,3-c]pyridin-5-yl)-1-(R)benzyloxymethyl-2-oxo-ethyl]-isobutyramide L-tartrate as either a single 10 mg oral dose in solution or as a single 3 mg loading dose followed by seven (7) 1 mg maintenance doses administered every two hours. The order of treatment was defined by a randomization schedule. Following initial administration, subjects were readmitted to the clinical research facility approximately 14 days later. During the second evaluation, the subject received the treatment not used during the previous session.

Growth hormone serum concentrations were determined following administration of the bolus or divided doses. Blood samples, adequate to provide 0.5 ml of serum, were collected just prior to administration of the first dose, and every 20 minutes thereafter for 24 hours for determination of growth hormone. Specimens were collected in tubes containing no additives, and were maintained at room temperature until clotted. The serum was separated from the whole blood and frozen at −20° C. within one hour of collection.

Growth hormone quantitation of the human serum samples was conducted using luminescence measurements by means of an Immulite® system (Diagnostic Products Corporation, Los Angeles, Calif.). All analyses were performed using a hGH Immulite® kit containing hGH test units (LGH 1), hGH reagent wedge (LGH 2) and hGH adjustors (LGHL and LGHH). These kits were obtained from DPC (Diagnostic Products Corporation, Los Angeles, Calif.). In addition, hGH sample diluent (LGHZ), chemiluminescent substrate module (LSUBX), probe wash module (LPWSZ) and the necessary Immulite® accessories were obtained from DPC. For each new kit, the Immulite® system was calibrated by running two adjuster samples (LGHL and LGHH) obtained from the manufacturer, containing a high and a low concentration of hGH in equine serum, respectively. Subsequently, the signals were plotted against the Master Curve to derive a slope and an intercept. On the basis of these values, the Immulite® system automatically decides whether the kit can be used for sample analysis. Samples were taken from the −20° C. freezer and thawed in a water bath at 30° C. for ten minutes. Subsequently, the samples were homogenized. An aliquot of 50 $\mu$L of the serum sample and an aliquot of a solution containing alkaline phosphatase conjugated anti-hGH (human growth hormone) antibody were automatically transferred into a sample cup containing an antibody coated polypropylene bead specific for hGH. After incubation at 37° C. for 30 minutes, the unbound enzyme conjugate was removed by a centrifugal wash, after which 200 $\mu$L of a substrate solution was added and incubated at 37° C. for a further ten minutes. The resulting luminescence was determined by means of an Immulite® system.

IGF-I serum concentrations were determined following administration of the bolus or divided doses. Blood samples, adequate to provide 1.5 ml serum, were collected just prior to administration of the first dose, and at 12 and 24 hours after administration of the first dose, for determination of IGF-I concentrations. Specimens were collected in tubes containing no additives, and were maintained at room temperature until clotted. The serum was separated from the whole blood and frozen at −20° C. within one hour of collection.

IGF-I quantitation of the human serum samples was conducted using the "DSL-5600A Active™ IGF-I Coated-Tube IRMA (immunoradiometric assay) by Extraction" Kit (Diagnostic Systems Laboratories Inc., Webster, Tex.). All analyses were performed using the extraction kit containing anti-IGF-I coated tubes (plastic tubes on which the first antibody, i.e., anti-IGF-I immunoglobulin is immobilized on the wall of the tube), [$^{125}$I]Anti-IGF-I ([$^{125}$I]labelled anti-IGF-I antibodies, which are provided in a buffer containing sodium azide and a protein stabilizer), extraction solution, neutralizing solution, IGF-I control and IGF-I standard samples. The lyophilized IGF-I control and standard samples were used for the preparation of calibration and validation samples as described. The extraction solution consisted of a mixture of 2.0 N HCl/ethanol (12.5:87.5, in volume %) and the neutralizing solution contained a neutralizing buffer and sodium azide. Lyophilized calibration and validation samples were prepared by the addition of 1 mL of water to the ready-to-use samples. The calibration samples were prepared at seven levels, i.e., 4.50, 16.0, 65.0, 122, 180, 410 and 640 $\mu$g.L$^{-1}$. The validation samples were prepared at levels of 4.50, 65.0, 180 and 640 $\mu$g.L $^{-1}$. Samples were taken from the −20°0 C. freezer and thawed in a water bath at 30° C. for ten minutes. Subsequently, the samples were homogenized and centrifuged at 3200×g. An aliquot of 100 $\mu$L of the human serum sample was transferred into a 5 mL polypropylene tube and incubated with 400 $\mu$L of extraction solution for 30 minutes at room temperature. After centrifugation at 5,000 r.p.m, 100 $\mu$L of the supernatant was transferred into another polypropylene tube. Next, 500 $\mu$L of neutralization solution was added. This neutralized human serum extract was ready for use in the actual IRMA after having vortexed it briefly. An aliquot of 50 $\mu$L of the extracted serum sample, validation or calibration sample was transferred into an anti-IGF-I antibody coated tube, and immediately afterwards 200 $\mu$L of [$^{125}$I]anti-IGF-I antibody solution was added. The samples were incubated for three hours at room temperature on a multimixer at 180 r.p.m. After three hours, all tubes were decanted and drained on adsorbent paper. Residual droplets on the rims of the tube were removed by blotting. Next, the tubes were washed three times with Milli-Q water (Winokur Water Systems Corporation, Bethel, Conn.), applying the above-described drying procedure between the washing steps. The remaining [$^{125}$I]radioactivity of all tubes was determined by counting for five minutes using a Canberra-Packard Cobra II™ 5002 ã-counter (Canberra-Packard, Schwadorf, Austria).

Results

The results demonstrated divided dosing of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate lowered the initial growth hormone peak at 1–2 hours after the first dose compared to bolus. These findings also demonstrated an increase in frequency and amplitude of growth hormone serum concentrations over 8–20 hours following simulated sustained release compared to bolus dosage administration. In addition, the pulsatility of GH concentrations increased at times typical of biological times not as an acute response after each maintenance dose. The IGF-I serum concentration change from baseline at 24 hours post first dose was increased following simulated sustained release dosing compared to bolus (Table 2-1).

TABLE 2-1

Individual Serum Growth Hormone (GH) and IGF-1 Concentrations in Young, Healthy Male Volunteers Following Oral Administration of 10 mg of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate As A Bolus or Simulated Sustained Release (Divided)

| Subject | Dosing Regimen | GH $AUC_{0-24}$ | GH $C_{max}$ | GH $T_{max}$ | IGF-I Change from Baseline at 24 hrs post dose ($\mu$g/ml) |
|---|---|---|---|---|---|
| 1 | bolus | 297 | 133 | 1 | 102 |
| 1 | divided | 313 | 107 | 1 | 130 |

TABLE 2-1-continued

Individual Serum Growth Hormone (GH) and
IGF-1 Concentrations in Young, Healthy
Male Volunteers Following Oral Administration
of 10 mg of 2-amino-N-[2-(3a-(R)-
benzyl-2-methyl-3-oxo-2,3,3a,4,6,7-hexahydro-
pyrazolo[4,3-c]pyridin-5-yl)-1-(R)-
benzyloxymethyl-2-oxo-ethyl]-isobutyramide
L-tartrate As A Bolus or Simulated
Sustained Release (Divided)

| Subject | Dosing Regimen | GH $AUC_{0-24}$ | GH $C_{max}$ | GH $T_{max}$ | IGF-I Change from Baseline at 24 hrs post dose ($\mu$g/ml) |
|---|---|---|---|---|---|
| 2 | bolus | 256 | 125 | 1 | 98 |
| 2 | divided | 152 | 77 | 1 | 105 |
| 3 | bolus | 220 | 121 | 1 | 110 |
| 3 | divided | 242 | 82 | 1 | 123 |
| 4 | bolus | 292 | 131 | 0.67 | 98 |
| 4 | divided | 251 | 80 | 1 | 107 |

Example 3

Pituitary Cell Desensitization—Growth Hormone Release Assay

The ability of a growth hormone secretagogue such as GHRP-6 or 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to induce homologous desensitization of the growth hormone secretion response was demonstrated in cultures of dispersed rat pituitary cells. The experiment was designed so that cultures were exposed to a growth hormone secretagogue for 60 min, then growth hormone release was measured during a subsequent 15 min exposure to the same or different growth hormone secretagogue. Results indicate that continuous exposure to growth hormone secretagogue rapidly desensitizes rat pituitary cells. Thus, based on these results, it appears unlikely that sustained release growth hormone secretagogue formulations would elicit the desired response (i.e., stimulate the release of growth hormone).

Methods

Anterior pituitary glands from male Wistar rats (150–175 g, Charles River, Laboratories, Wilmington, Mass.) were collected in Hank's Balanced Salt Solution (#14170, Life Technologies, Gaithersburg, Md.). Glands were minced with a scalpel, then incubated with bacterial protease (Type IX, EC3.4.24.4, #P-6141, Sigma Chemicals, Milwaukee, Wis.) at 10 U/ml to release individual cells. Cells were pelleted by centrifugation at 200×g for 15 min, then suspended in culture medium and plated at a density of $6.0-6.5 \times 10^4$ cells per 0.5 ml per well in 48-well tissue culture plates (#3848, Costar Corporation, Cambridge, Mass.). Culture medium consisted of D-MEM (Dulbecco's Modified Eagle Medium) with high glucose and sodium bicarbonate (#11965) supplemented with 10% heat-inactivated horse serum (#26050, Life Technologies, Gaithersburg, Md.), 2.5% fetal bovine serum (#16140, Life Technologies, Gaithersburg, Md.), 0.1 mM MEM non-essential amino acids (#11140, Life Technologies, Gaithersburg, Md.), 100 U/ml nystatin (#15340, Life Technologies, Gaithersburg, Md.) and 50 ug/ml gentamicin sulfate (#15750, Life Technologies, Gaithersburg, Md.). Cultures were maintained for 3–4 days in a humidified, 5% $CO_2$/95% air incubator at 37° C. prior to performing assays for growth hormone release.

For growth hormone release assays, cultures were pre-equilibrated at 37° C. in pre-warmed release medium for 1 h in the presence of a growth hormone secretagogue or excipient (Pretreatment). Release medium consisted of Phenol Red-free D-MEM without bicarbonate (#23800, Life Technologies, Gaithersburg, Md.) supplemented with 25 mM N-[2-hydroxyethyl]piperazine-N'-[2-ethanesulfonic acid] (HEPES), 4.5 g/L glucose, 0.11 g/L sodium pyruvate, 0.584 g/L L-glutamic acid and 0.5% bovine serum albumin (#A-7888, Sigma Chemicals, Milwaukee, Wis.), adjusted to pH 7.4. After pretreatment, the medium was removed and replaced with fresh pre-warmed release medium containing a growth hormone secretagogue or excipient at 0.5 ml/well for 15 min (Treatment). Medium from the Treatment was collected, centrifuged to remove any cells, then assayed for growth hormone content by a conventional double-antibody radioimmunoassay using monkey anti-growth hormone antisera (NIDDK anti-rGH-S-5) and reference rat growth hormone standard (NIDDK-rGH-RP) from Dr. A. F. Parlow, Harbor-UCLA Medical Center, Torrance, Calif. Immune complexes were precipitated using goat anti-monkey immunoglobulin G (#55418, Cappel, Durham, N.C.).

Growth hormone secretagogue solutions were prepared at 1000 times the desired concentration and diluted into pre-warmed release medium immediately before use. Peptides such as His-D-Trp-Ala-Trp-Ala-Trp-D-Phe-Lys-NH2 (GHRP-6, #8061, Peninsula Laboratories, Belmont, Calif.) and rat growth hormone releasing factor (GHRH, #8068, Peninsula Laboratories, Belmont, Calif.) were dissolved at 100 $\mu$M in 4 mM acetic acid, 10% ethanol, 0.1% bovine serum albumin; other growth hormone secretagogues were dissolved at 5 mM in dimethyl sulfoxide.

Results

The data in Table 3-1 demonstrate apparent homologous desensitization of cellular responses to 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and GHRP-6 and cross-desensitization between these two growth hormone secretagogues. As shown in Table 3-1, rat pituitary cells showed stimulation of growth hormone release in response to 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate (Compound A) after pretreatment with GHRH but not with GHRP-6.

TABLE 3-1

Growth Hormone Release by Rat Pituitary Cells after Pretreatment with a Growth Hormone Secretagogue (Mean ± standard deviation, n = 4)

| Group | Pretreatment 60 min | Treatment 15 min | GH release ng/mL/15 min |
|---|---|---|---|
| 1 | none | none | 9.28 ± 1.33 |
| 2 | none | 100 nM GHRP-6 | 31.01 ± 8.46 * |
| 3 | none | 10 nM Compound A | 25.17 ± 4.32 * |
| 4 | 100 nM GHRP-6 | none | 9.06 ± 1.87 |
| 5 | 100 nM GHRP-6 | 100 nM GHRP-6 | 7.83 ± 0.98 |
| 6 | 100 nM GHRP-6 | 10 nM Compound A | 7.64 ± 1.92 |
| 7 | 100 nM GHRH | none | 12.67 ± 3.31 |
| 8 | 100 nM GHRH | 10 nM Compound A | 36.99 ± 2.43 * |

* Different from Group 1 by Student's t-test, P < 0.05

Example 4

Pituitary Cell Desensitization—Intracellular Calcium Assay

The inability of somatotrophs to respond to repeated administration of a growth hormone secretagogue by transiently increasing their intracellular calcium concentration was demonstrated in perfused cultures of dispersed rat pituitary cells. Thus, it appears that sustained release formulations would not provide the desired in vivo response. The experiment was designed so that changes in intracellular calcium concentration could be continuously monitored during successive exposures of the same cells to the indicated test substances.

Methods

Rat pituitary cells were isolated as described in Example 3 and plated onto poly-D-lysine-coated glass coverslips, one coverslip per well in 12-well plates, at a density of 3–4×10$^5$ cells per well. Assays were performed 3–4 days after plating. Cells were loaded with 5 μM fura-2 AM (Molecular Probes, Eugene, Oreg.), a calcium-sensitive fluorescent dye, by incubation for 30 min at room temperature. Fura-2 was dissolved in dimethylsulfoxide at 5 mM, then diluted into KRH buffer (115 mM NaCl, 5.4 mM KCl, 1.8 mM CaCl$_2$, 1 mM MgCl$_2$, 0.96 mM NaH$_2$PO$_4$, 25 mM HEPES, 6 mM glucose and 0.05% bovine serum albumin, adjusted to pH 7.3)

To assay changes in intracellular calcium concentration, a coverslip with attached cells was mounted in a perfusion chamber on the stage of an inverted microscope (Zeiss Axiovert 135 with epifluorescence, Geschaftsbereich Mikroscopie, Oberkochen, Germany) and continuously superfused at room temperature. After superfusion with KRH for 1–2 min, baseline fluorescence was recorded. Each test substance was applied for 2 min, followed by washout with KRH prior to stimulation with the next test substance. Up to 20 individual cells per field were selected for recording and were excited alternately at wavelengths of 380 nm or 340 nm (slit width 15 nm). Fluorescence emission at 510 nm was collected at 5 sec intervals by a low light CCD camera (Hamamatsu Photonics, Hamamatsu City, Japan), and digitized images for the two excitation wavelengths were analyzed using Videoprobe software (ETM Systems, Irvine, Calif.) to determine the 340 nm/380 nm fluorescence ratio for individual cells during each time interval. The 340 nm/380 nm fluorescence ratio is proportional to the concentration of intracellular calcium.

Results

The data demonstrate apparent homologous desensitization of cellular responses to 2-amino-N-[2-(3a-(R)-benzyl-2-methyl-3-oxo-2,3,3a,4,6,7-hexahydro-pyrazolo[4,3-c] pyridin-5-yl)-1-(R)-benzyloxymethyl-2-oxo-ethyl]-isobutyramide L-tartrate and GHRP-6 and cross-desensitization between these two growth hormone secretagogues (but no desensitization between GHRH and 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate). In the experiment, cells that initially responded to 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate or GHRP-6 with a calcium flux are refractory when re-exposed to 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate after washout with buffer, yet the same cells remained responsive to KCl. Based on these data, it is not evident that continuous exposure to a growth hormone secretagogue would elicit multiple cycles of growth hormone release from pituitary cells since the cells rapidly become refractory to this stimulus.

Example 5

Excipient Selection Based on Active Compound Solubility Screening

The ability of selected excipients to maintain the solubility of 2-amino-N-[2-(3a-(R)-benzyl-2-methyl-3-oxo-2,3,3a, 4,6,7-hexahydro-pyrazolo[4,3-c]pyridin-5-yl)-1-(R)-benzyloxymethyl-2-oxo-ethyl]-isobutyramide L-tartrate above 150 mg/ml was demonstrated in solutions of the candidate excipient. Such excipients are useful in making osmotic sustained release tablets. The active compound solubility screening experiment was designed so that filtrate from saturated excipient solutions were visually monitored for precipitation over 5 minute intervals following addition of 50 mg/ml of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate solution. The active compound solubility measured in this manner exceeded 150 mgA/ml (mgA is the milligrams of active compound). Preferred excipients were selected based on their ability to maintain 2-amino-N-[2-(3a-(R)-benzyl-2-methyl-3-oxo-2,3,3a,4,6,7-hexahydro-pyrazolo[4,3-c] pyridin-5-yl)-1-(R)-benzyloxymethyl-2-oxo-ethyl]-isobutyramide L-tartrate solubility above 150 mg/ml.

Methods

This example illustrates a method to select excipients, including organic acids, bases, buffers, binders, lubricants, surfactants and solubilizing agents, that have the ability to maintain the solubility of 2-amino-N-[2-(3a-(R)-benzyl-2-methyl-3-oxo-2,3,3a,4,6,7-hexahydro-pyrazolo[4,3-c] pyridin-5-yl)-1-(R)-benzyloxymethyl-2-oxo-ethyl]-isobutyramide L-tartrate above 150 mg/ml. The excipients were screened by preparing a saturated solution (unless otherwise noted) of the candidate excipient in water at 37° C. for 2 hrs, and filtering the undissolved portion. Then, three incremental amounts of 2-amino-N-[2-(3a-(R)-benzyl-2-methyl-3-oxo-2,3,3a,4,6,7-hexahydro-pyrazolo[4,3-c] pyridin-5-yl)-1-(R)-benzyloxymethyl-2-oxo-ethyl]-isobutyramide L-tartrate at 50 mg/ml were added to a 3 ml filtrate solution of the excipient to achieve a maximum solubility of 150 mgA/ml. The solution was maintained at 37° C. for 5 minutes prior to making the visual observation for any undissolved particulates. The active compound solubility was then determined by visual observation over the range of 0–50, 50–100, 100–150, or >150 mgA/ml (Table 5-1).

Results

The results of this solubility test are listed in Table 5-1. All of the acids evaluated successfully maintained the solubility of 2-amino-N-[2-(3a-(R)-benzyl-2-methyl-3-oxo-2,3,3a,4,6, 7-hexahydro-pyrazolo[4,3-c]pyridin-5-yl)-1-(R)-benzyloxymethyl-2-oxo-ethyl]-isobutyramide L-tartrate above 150 mg/ml. The basic compounds of L-lysine and L-arginine reduced the solubility below 50 mg/ml. The saturated solutions of phosphate, citrate, sulfate, or chloride salts suppressed the solubility from greater than 150 mg/ml to less than 50 mg/ml and formed a cloudy gel. However, the sodium bitartrate buffer successfully maintained the solubility of the active compound above 150 mgA/ml. The active compound substance solubility was reduced by the solubilizing agent, sulfobutylether cyclodextrin, to 100–150 mgA/ml. Sodium lauryl sulfate as a surfactant caused 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to form a clear gel during the second incremental addition of active compound solution. All of the binders (microcrystalline cellulose, silicified microcrystalline cellulose, and polyethylene glycol) and lubricants (calcium and magnesium stearate) evaluated according to the excipient screening test maintained the solubility of active compound substance above 150 mgA/ml.

TABLE 5-1

2-Amino-N-[2-(3a-(R)-benzyl-2-methyl-3-oxo-2,3,3a,4,6,7-hexahydro-pyrazolo[4, 3-c]pyridin-5-yl)-1-(R)-benzyloxymethyl-2-oxo-ethyl]-isobutyramide L-tartrate (Compound A) solubility in saturated excipient solutions maintained at 37° C. upon three incremental additions of 50 mgA/ml

| Excipient | Approximate Excipient Concentration (mg/ml) | COMPOUND A Solubility (mg/ml) |
|---|---|---|
| ACIDS/BASES: | | |
| Ascorbic acid | 400 | >150 |
| L-aspartic acid | 7 | >150 |
| Citric acid | 600 | >150 |
| Fumaric acid | 10 | >150 |
| Succinic acid | 80 | >150 |
| Tartaric acid | 50 (a) | >150 |
| L-arginine | 150 | < 50 |
| L-lysine | 50 (a) | <50, cloudy gel |
| BUFFERS: | | |
| Potassium phosphate monobasic | 400 | <50 |
| Potassium chloride | 360 | <50, cloudy gel |
| Sodium bitartrate | 110 | >150 |
| Sodium citrate | 520 | <50, cloudy gel |
| Sodium chloride | 360 | <50, cloudy gel |
| Sodium phosphate monobasic | 1000 | <50, cloudy gel |
| Sodium phosphate tribasic | 290 | <50, cloudy gel |
| BINDERS: | | |
| Microcrystalline cellulose | <1 (b) | >150 |
| Microcrystalline cellulose, silicified | <1 (c) | >150 |
| Polyethylene glycol | 50 (d) | > 150 |
| LUBRICANTS: | | |
| Calcium stearate | < 1 (e) | >150 |
| Magnesium stearate | <1 | >150 |
| SOLUBILIZER/SURFACTANTS: | | |
| Cyclodextrin, sulfobutylether | 1000 | 100–150 |
| Sodium lauryl sulfate | 50 | 50–100, clear gel |

(a) excipient solution prepared below saturation, at 50 mg/ml
(b) Avicel PH102, FMC Corporation, Philadelphia, PA; excipient solution prepared at 80 mg/ml
(c) Prosolv SMCC50, Mendell, Cedar Rapids, IA; excipient solution prepared at 80 mg/ml
(d) Carbowax 3350, Union Carbide Corporation, Charleston, WV.
(e) excipient solution prepared at 2 mg/mL Preferred excipients, based on this screening test, are organic acids. Exemplary organic acids are tartaric, citric, ascorbic, fumaric, succinic, and L-aspartic acids. Sodium bitartrate buffer solutions also maintained active compound substance solubility. Some sustained release dosage forms with such acids or buffers in the formulation can perform better than those without such acids or buffers. This is particularly true for osmotic-based formulations that deliver a solution of active compound.

Preferred tablet binders for 2-amino-N-[2-(3a-(R)-benzyl-2-methyl-3-oxo-2,3,3a,4,6,7-hexahydro-pyrazolo[4, 3-c]pyridin-5-yl)-1-(R)-benzyloxymethyl-2-oxo-ethyl]-isobutyramide L-tartrate are microcrystalline cellulose, silicified; microcrystalline cellulose; and polyethylene glycol based on the screening test. Preferred lubricants for the dosage form are calcium stearate and magnesium stearate.

None of these excipients adversely affected active compound solubility.

Example 6

Osmotic Agent Selection Based on Active Compound Solubility Screening

The ability of selected osmotic agents (osmogens), to maintain the solubility of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate above 150 mg/ml was demonstrated in solutions of the candidate osmogen. The active compound solubility screening experiment was designed so that filtrates from saturated osmogen solutions were visually monitored for precipitation over 5 minute intervals following each of three incremental additions of 50 mg/ml of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate solution. The active compound solubility measured in this manner exceeded 150 mg/ml. Preferred excipients were selected based on their ability to maintain 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate solubility above 150 mg/ml.

Methods

This example illustrates a method to select the osmotic agent for osmotic dosage forms that have the ability to maintain the solubility of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate above 150 mg/ml while minimizing the potential degradation of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate by the reducing sugar class of osmogens. The osmogens were screened by preparing a saturated solution (unless otherwise noted) of the candidate osmogen in water at 37° C. for 2 hours, and filtering the undissolved portion as described in Example 5. The active compound substance solubility was then determined by visual observation over the range of 0–50, 50–100, 100–150, or >150 mgA/ml (Table 6-1).

Results

The results of the solubility test are listed in Table 6-1. Most of the osmogens evaluated successfully maintained the solubility of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate above 150 mg/ml with the exception of fructose and xylitol.

TABLE 6-1

2-Amino-N-[2-(3a-(R)-benzyl-2-methyl-3-oxo-2,3,3a,4,6,7-hexahydro-pyrazol[4,3-c]pyridin-5-yl)-1-(R)-benzyloxymethyl-2-oxo-ethyl]-isobutyramide L-tartrate (Compound A) solubility in saturated osmogen solutions maintained at 37° C. upon three incremental additions of 50 mgA/ml

| Osmogen | Approximate Osmogen Concentration (mg/ml) | COMPOUND A Solubility (mg/ml) |
|---|---|---|
| Fructose | 250 (a) | <50 |
| Lactose | 200 | >150 |
| Mannitol | 180 | >150 |
| Sodium bitartrate | 110 | >150 |

TABLE 6-1-continued

2-Amino-N-[2-(3a-(R)-benzyl-2-methyl-3-oxo-2,3,3a,4,6,7-hexahydro-pyrazol[4,3-c]pyridin-5-yl)-1-(R)-benzyloxymethyl-2-oxo-ethyl]-isobutyramide L-tartrate (Compound A) solubility in saturated osmogen solutions maintained at 37° C. upon three incremental additions of 50 mgA/ml

| Osmogen | Approximate Osmogen Concentration (mg/ml) | COMPOUND A Solubility (mg/ml) |
|---|---|---|
| Sorbitol | 250 (a) | >150 |
| Xylitol | 250 (a) | <50 |

(a) excipient solution prepared below saturation, at 250 mg/ml

Preferred osmogens, based on the solubility screening test, are lactose, mannitol, sodium bitartrate and sorbitol. Further preferred osmogens, based on the ability of (cyclic) reducing sugars to degrade active compound substances with amines, are mannitol, sodium bitartrate, and sorbitol. Some sustained-release dosage forms with such osmogens in the tablet formulation can perform better than those without such osmogens. This is particularly true for osmotic-based formulations.

Example 7

Sustained Release Tablets

This example illustrates a process for making osmotic tablets comprising a tablet core containing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate surrounded by a semi-permeable asymmetric membrane coating. The processing of the core tablet comprised (1) blending of core components as designated in Table 7-1, except for magnesium stearate; (2) screening and reblending the same components; (3) adding and blending magnesium stearate; (4) compressing core tablets; (5) spraying an asymmetric membrane coating to the core tablets; and (6) drying.

In batch sizes of 15–90 grams, 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate was blended in a suitable jar with all other components except magnesium stearate for 10 minutes using a Turbula shaker system (Willy A. Bachofen, Basel, Switzerland). Next, the blend was passed through a 30–35 mesh screen and blended again for 10 minutes. Then, magnesium stearate was added and blended for 3 minutes. Using a conventional tablet press (Manesty F-Press, Manesty Machines, Liverpool, England), the final blend was compressed into tablets using 5/16 inch or 3/8 inch standard round concave (SRC) punches for the 200 or 333.3 mg tablet weights, respectively. A summary of the compositions manufactured by direct compression of the formulation blend at 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate per tablet is shown in Examples 7A–7K, as detailed in Table 7-1. Significant core compositional changes included the type and amount of acid or osmogen. The amount of binder and lubricant were varied accordingly to obtain good tableting properties.

A semi-permeable membrane coating (as described in U.S. Pat. No. 5,612,059) was applied to these tablets using a HCT-30 explosion-proof pan coater (Vector Corporation, Marion, Iowa) operated at a spray rate of 20 grams per minute, an inlet temperature of 40–45° C. and air flow rate of 30 cfm (14158.43 $cm^3$/sec). The coating formulation applied to Examples 7A–7H consisted by weight of 10% cellulose acetate (Eastman Chemical, CA-398-10, Kingsport, Tenn.), 2.5% polyethylene glycol (PEG3350, Union Carbide Corporation, Charleston, W. Va.), 15% water, and 72.5% acetone. For Examples 7I, 7J, and 7K, the coating formulation applied to the tablets consisted of 9/3/19/69, 6/4/23/67, and 6/4/23/67 percent by weight of cellulose acetate, polyethylene glycol, water, and acetone, respectively (Table 7-1). The coated tablets were dried in the coater for 10–15 minutes at an inlet temperature set point of 60° C. and/or dried in an oven for 16 hours at 50° C. before testing for dissolution performance. After drying, the weight of the applied coating material was determined based on a percentage of the initial core tablet weight. These tablets contained a 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose of 10 mg/tablet, and are examples of sustained release formulations.

TABLE 7-1

| | | | Core Composition | | | | | | Asymmetric |
|---|---|---|---|---|---|---|---|---|---|
| | Core | | Acid/ Solubilizer | | Osmogen | | | | Membrane Coating |
| Ex No. | Wt (mg) | Dose mgA | Type | Wt % | Type | Wt % | Avicel Wt % | MgSt Wt % | Wt % (dry wt %) |
| 7A | 200 | 10 | none | — | lactose | 63 | 30 | 0.5 | 11.5 |
| 7B | 200 | 10 | none | — | mannitol | 63 | 30 | 0.5 | 12.0 |
| 7C | 200 | 10 | tartaric | 50 | mannitol | 20 | 23 | 0.5 | 12.1 |
| 7D | 200 | 10 | fumaric | 20 | sorbitol | 50 | 22.5 | 1.0 | 13.8 |
| 7E | 200 | 10 | fumaric | 20 | mannitol | 50 | 23 | 0.5 | 11.4 |
| 7F | 200 | 10 | fumaric | 20 | mannitol | 50 | 23 | 0.5 | 22.6 |
| 7G | 200 | 10 | succinic | 20 | sorbitol | 50 | 22.5 | 1.0 | 11.5 |
| 7H | 200 | 10 | none | — | NaBT | 62.5 | 30 | 1.0 | 17.1 |
| 7I | 200 | 10 | fumaric | 20 | mannitol | 50 | 22 | 1.5 | 11.2 |
| 7J | 333.3 | 10 | fumaric | 12 | mannitol | 34 | 48.6 | 1.5 | 14.7 |
| 7K | 333.3 | 10 | fumaric | 16 | mannitol | 44 | 34.6 | 1.5 | 12.7 |

MgSt means magnesium stearate
NaBT means sodium bitartrate

Example 8

In Vitro Performance of Sustained Release Tablets

All sustained release asymmetric membrane tablets from Example 7 were tested for active compound release performance using dissolution procedures with analysis by reverse-phase high performance liquid chromatography (RP HPLC). The sustained release dosage forms were tested in a standard USP rotating paddle apparatus as disclosed in United States Pharmacopeia XXIII (USP) Dissolution Test Chapter 711, Apparatus 2. Paddles were rotated at 50 rpm (unless noted as 100 or 150 rpm) and the dissolution was conducted in, as test medium, 900 ml of either simulated gastric fluid without enzyme pH 1.2 (sgn) or simulated intestinal fluid without enzyme pH 7.5 (sin) at 37° C. The dissolution, or in vitro, test medium was prepared as disclosed in USP XXIII Test Solutions on page 2053, 1995. Simulated gastric fluid without enzyme (sgn) was prepared by dissolving 2.0 grams of sodium chloride in 7.0 ml of hydrochloric acid, and subsequently diluted to 1000 ml with water to form a pH 1.2 solution. The simulated intestinal fluid without enzyme (sin) was prepared by dissolving 6.8 grams of monobasic potassium phosphate in 250 ml of water, mixing, and adding 190 ml of 0.2N sodium hydroxide and 400 ml of water that was adjusted with 0.2N sodium hydroxide to a pH of 7.5 and diluted to 1000 ml with water. The sin and sgn test protocols are well know to those skilled in the art and are set forth in the United States Pharmacopoeia (USP).

At indicated times following test initiation (i.e., insertion of the dosage form into the apparatus), filtered aliquots (typically 2 or 10 mL) from the test medium were withdrawn and analyzed for 2-amino-N-[2-(3a-(R)-benzyl-2-methyl-3-oxo-2,3,3a,4,6,7-hexahydro-pyrazolo]pyridin-5-yl)-1-(R)-benzyloxymethyl-2-oxo-ethyl]-isobutyramide L-tartrate by RP HPLC as disclosed below. Dissolution results are reported as mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dissolved versus time or percent of 2-amino-N-[2-(3a-(R)-benzyl-2-methyl-3-oxo-2,3,3a ,4,6,7-hexahydro-pyrazolo[4,3-c]pyridin-5-yl)-1-(R)-benzyloxymethyl-2-oxo-ethyl]-isobutyramide L-tartrate dissolved versus time.

2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate quantification of the in vitro dissolution test samples described above was conducted by RP HPLC as follows. An aliquot of test solution was filtered to remove particulates. A fixed volume of 25 µl was injected onto the analytical column (15 cm length×3.9 mm diameter Waters Symmetry C8 column, Waters Company, Milford, Mass.) containing a 5 micron stationary phase. The mobile phase was composed of perchloric acid, water, and acetonitrile in volume percentages of 0.37/74.63/25.0. The mobile phase was prepared by adding 5 ml of perchloric acid to 1000 ml distilled water with stirring. Then, 750 ml of this aqueous perchloric acid solution was volumetrically measured and added to 250 ml acetonitrile while stirring. After mixing well, the mobile phase was degassed under reduced pressure with continuous stirring or ultrasonic agitation for 5 minutes. The mobile phase flow rate through the HPLC column was 2.0 ml/min with detection at 210 nm.

The results of the active compound release rate tests performed using the procedures described above are listed in Table 8-1. Dosage forms containing an osmogen but no acid (Examples 7A is lactose, 7B is mannitol, and 7H is sodium bitartrate) released 85% of the dose in 16, 12 and 24 hrs, respectively. The sustained release in vitro boundaries corresponding to the $C_{max}$ criteria are about 5.56 to about 16.67%/hr and corresponding to $\Delta T$ criteria are about 5.56 to about 25%/hr for about a 10 mg dose. The lack of an acid in the core formulation with low osmotic pressure producing agents (lactose and sodium bitartrate of Example 7A and 7H, respectively) resulted in a failure to meet the in vitro criteria, and therefore such formulations are not embodiments of this invention. The addition of an acid or solubilizer to the core tablet formulation was found to enhance the initial active compound release rate up through 8 hours increasing in order of the acid solubility from fumaric to succinic to tartaric acid. The increase in acid and osmogen content in the core tablet from about 12 to about 16% fumaric acid and about 34 to about 44% mannitol in Examples 7J and 7K significantly increased active compound release rates during 8–16 hours. Increasing the weight percent of coating applied to the tablet (from about 11.4 to about 22.6% in Example 7E and 7F, respectively) resulted in the greatest reduction in active compound release for every in vitro time point. For the core formulation of 7E and 7F, dosage forms coated in excess of 20 wt % did not meet the in vitro criteria stated above, and therefore Example 7F is not an embodiment of this invention. The active compound release rate was not dependent on the test medium (either SGN or SIN), or agitation rate (50, 100, and 150 rpm) typical of osmotic-based formulations.

TABLE 8-1

| Asymmetric Membrane (AM) Coated Tablet | | Fraction of Active Compound Release (%) At Specified Time (hr) | | | | | | | Calc'd Release Rate | Pass In Vitro Criteria |
|---|---|---|---|---|---|---|---|---|---|---|
| Tablet Ex. No. | In Vitro Media | 0 | 2 | 4 | 8 | 12 | 16 | 24 | (%/hr) | ($C_{max}$, $\Delta T$) |
| 7A | sgn | 0 | 5.6* | 28.5 | 55.0 | 72.9 | 83.0 | 92.4 | 5.2 | no, no |
| 7B | sgn | 0 | 8.9* | 39.1 | 68.5 | 85.5 | 91.5 | 97.3 | 7.1 | yes, yes |
| 7C | sgn | 0 | 33.6 | 56.6 | 75.5 | 80.1 | 81.8 | 85.4 | 6.7 | yes, yes |
| 7D | sgn | 0 | 38.4 | 60.9 | 81.2 | 88.1 | 91.8 | 95.2 | 10.2 | yes,yes |
| 7E | sgn | 0 | 17.0 | 35.0 | 62.3 | 79.4 | 86.3 | 93.1 | 6.6 | yes, yes |
| 7F | sgn | 0 | 3.5 | 13.5 | 34.5 | 52.0 | 66.8 | 77.9# | 3.9 | no, no |
| 7G | sgn | 0 | 41.2 | 68.5 | 85.7 | 92.8 | 94.5 | 99.4 | 10.7 | yes, yes |
| 7H | sgn | 0 | 7.0 | 16.3 | 35.8 | 52.8 | 64.9 | 84.7 | 3.5 | no, no |
| 7I | sgn | 0 | 18.4 | 34.3 | 62.1 | 82.0 | 94.5 | 96.2 | 6.8 | yes, yes |

TABLE 8-1-continued

| Asymmetric Membrane (AM) Coated Tablet | | | | | | | | | Calc'd | Pass In |
|---|---|---|---|---|---|---|---|---|---|---|
| Tablet Ex. No. | In Vitro Media | \multicolumn{7}{c}{Fraction of Active Compound Release (%) At Specified Time (hr)} | | Release Rate (%/hr) | Vitro Criteria ($C_{max}$, $\Delta T$) |
| | | 0 | 2 | 4 | 8 | 12 | 16 | 24 | | |
| 7I | sin | 0 | 13.4 | 29.6 | 55.9 | 76.3 | 88.8 | 100 | 5.9 | yes, yes |
| 7I | sin; 100 rpm | 0 | 12.3 | 28.4 | 54.4 | 74.0 | 86.7 | 96.4 | 5.7 | yes, yes |
| 7I | sin; 150 rpm | 0 | 11.3 | 27.3 | 53.9 | 73.5 | 86.3 | 96.1 | 5.7 | yes, yes |
| 7J | sgn | 0 | 15.5 | 29.2 | 58.4 | 80.9 | 92.1 | 100 | 6.7 | yes, yes |
| 7J | sin | 0 | 13.0 | 23.9 | 49.6 | 71.9 | 86.4 | 96.7 | 5.6 | yes, yes |
| 7K | sin | 0 | 15.4 | 29.7 | 60.1 | 82.5 | 93.4 | 99.4 | 6.8 | yes, yes | sgn means simulated gastric fluid, pH 1.2
sin means simulated intestinal fluid, pH 7.5
*release measured at 1 hour instead of 2 hour
release measured at 20 hours instead of 24 hour Preferred sustained release osmotic dosage forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate contain an osmotic agent producing osmotic pressures similar to or above 38 atmospheres (mannitol, sorbitol), or contain an organic acid such as fumaric, succinic or tartaric acid to enhance initial release performance. Preferred coating levels for the sustained release osmotic dosage forms are formulation and tablet size dependent, and must be less than 20 wt % for Example 7E and 7F. With the exception of Examples 7A, 7F, and 7H, all formulations listed in Table 8-1 demonstrate sustained release of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and are embodiments of this invention.

Example 9

Sustained Release Tablets

This example illustrates a method for making formulations of 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate osmotic tablets comprising a tablet core containing active compound surrounded by a semi-permeable asymmetric membrane coating. The processing of the core tablet comprised (1) blending of core components as designated in Table 9-1, except for magnesium stearate; (2) milling and reblending the same components; (3) adding and blending a portion of the magnesium stearate; (4) dry granulating; (5) milling/screening and reblending; (6) adding and blending the remaining portion of magnesium stearate; (7) compressing core tablets; (8) spraying an asymmetric membrane coating to the core tablets; and (9) drying.

In batch sizes of 2–57 kilograms, 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate was blended with all other components except magnesium stearate for 15 minutes in a suitable sized stainless steel twin-shelled blender [8 quart (7.6 L) to 5 cubic feet (141.9 L)]. Next, the blend was passed through a mill (Fitz model JT or D mill fitted with #1A plate, medium speed, knives forward) and blended again for 30 minutes. Then, magnesium stearate was added and blended for 5 minutes. The partially lubricated blend was dry granulated using a roller compactor (Freund TF-Mini or TF-156 roller compacter, Freund Industrial Co.) with auger screw feed of 8–12 rpm, pressure 40–25 kg/cm$^2$, and roller speed of 5–12 rpm. The roller compactor was fitted with an oscillating roller granulator screen size of 20–30 mesh to mill the compacted ribbons. Next, the granulation was blended for 20 minutes before the last portion of magnesium stearate was added and reblended for 5 minutes.

Using a conventional tablet press (Kilian T100 or LX21, Kilian and Co., Inc, Horsham, Pa.), the final blend was compressed into tablets using 5/16 or 3/8 inch standard round concave (SRC) punches for the 200 or 333.3 mg tablet weights, respectively. A summary of the compositions manufactured by dry granulation of the preferred formulation blend at 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate per tablet is shown in Examples 9A–9C, as detailed in Table 9-1. The more preferred formulation for the core tablet is 9C.

TABLE 9-1

| | | | \multicolumn{5}{c}{Core Composition} | | |
|---|---|---|---|---|---|---|---|---|
| Example No. | Core Wt (mg) | Dose (mgA) | \multicolumn{2}{c}{Acid/Solubilizer} | \multicolumn{2}{c}{Osmogen} | Avicel Wt % | MgSt Wt % |
| | | | Type | Wt % | Type | Wt % | | |
| 9A, 9B | 333.3 | 10 | fumaric | 12 | mannitol | 34 | 48.6 | 1.5 |
| 9C | 200 | 10 | fumaric | 20 | mannitol | 50 | 22.0 | 1.5 |

MgSt means magnesium stearate

A semi-permeable membrane coating (as described in U.S. Pat. No. 5,612,059) was applied to these tablets using a HCT-30 or HCT-60 explosion-proof pan coater (Vector Corporation, Marion, Iowa). The small scale coating pan, HCT-30, was operated at a spray rate of 20 grams per minute, an inlet temperature of 40–45° C. and air flow rate of 30 cfm (14158.43 cm$^3$/sec). The larger coating pan, HCT-60, was operated at a spray rate of 180 grams per minute divided between 2 guns, an inlet temperature of 55° C. and air flow rate of 300 cfm. The asymmetric membrane coating formulations applied to the 10 mgA core tablet provided a short duration which released 80% of the dose in 10–12 hrs and a long duration that released 80% in 20–24 hrs. The short and long duration coatings for the 10 mgA tablets in Example 9A and 9B consisted of cellulose acetate/polyethylene glycol/water/acetone ratios of 6/4123/67 (w/w) coated to an increase in the initial weight of 15.5 and 18.6%, respectively (Table 9-2). For the more preferred 10 mg tablet core (9C), the short duration coating formulation was composed of 9/3/19/69 applied to 19.5 wt % (Table 9-2). The coated tablets were dried in the coater for 15 minutes at an inlet temperature set point of 60° C. and dried in an oven (Gruenberg solvent tray oven, Gruenberg Oven Company, Williamsport, Pa.) for 16 hours at 50° C. before testing for dissolution performance. After drying, the weight of the applied coating material was determined based on a percentage of the initial core tablet weight.

TABLE 9-2

| Example No. | Core | | Osmotic Coating Solution | | | | Coating Weight (dry wt %) |
|---|---|---|---|---|---|---|---|
| | Weight (mg) | Dose (mgA) | CA (wt %) | PEG (wt %) | Water (wt %) | Acetone (wt %) | |
| 9A | 333.3 | 10 | 6 | 4 | 23 | 67 | 15.5 |
| 9B | 333.3 | 10 | 6 | 4 | 23 | 67 | 18.6 |
| 9C | 200.0 | 10 | 9 | 3 | 19 | 69 | 19.5 |

CA means cellulose acetate (Eastman Chemical, CA-398-10, Kingsport, TN)
PEG means polyethylene glycol (BASF, PEG3350, Union Carbide Corporation, Charleston, WV)

Example 10

In Vitro Performance of Sustained Release Tablets

The sustained release asymmetric membrane tablets from Example 9 were tested for active compound release performance using dissolution procedures described in Example 8. The results of the active compound release rate tests performed using those procedures are listed in Table 10-1.

The sustained release in vitro boundaries corresponding to the $C_{max}$ criteria are 5.56–16.67%/hr and corresponding to $\Delta T$ criteria are 5.56–25%/hr for a 10 mg dose. For the 333.3 mg tablet, increased coating level from 15.5 to 18.6% resulted in a reduction in release rate from 5.7 to 4.1%/hr in SIN media. The higher coating level of 18.6% in Example 9B resulted in a failure to meet the in vitro boundaries, and therefore is not an embodiment of this invention.

Preferred coating level is formulation and tablet size dependent, and must be less than 18 wt % for the 333 mg tablet. Examples 9A and 9C listed in Table 10-1 demonstrate sustained release of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and are embodiments of this invention.

The more preferred osmotic dosage form for the 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate asymmetric membrane coated tablet is exemplified by Example 9C, in which the core tablet size is smaller, which allows for use of a coating formulation with higher polymer-to-plasticizer ratio.

TABLE 10-1

| Asymmetric Membrane (AM) Coated Tablet | | Fraction of Active compound Release (%) At Specified Time (hr) | | | | | | | Calcd Release Rate %/hr | Pass In Vitro Criteria $C_{max}$, $\Delta T$ |
|---|---|---|---|---|---|---|---|---|---|---|
| Tablet Ex. No. | In Vitro Media | 0 | 2 | 4 | 8 | 12 | 16 | 24 | | |
| 9A | sgn | 0 | 11.3 | 24.0 | 53.7 | 77.8 | 92.4 | 101 | 6.5 | yes, yes |
| 9A | sin | 0 | 9.8 | 20.4 | 46.8 | 71.1 | 87.5 | 99.9 | 5.7 | yes, yes |
| 9B | sin | 0 | 4.3 | 12.7 | 33.1 | 55.0 | 72.9 | 91.8 | 4.1 | no, no |
| 9C | sgn | 0 | 5.1* | 34.5 | 63.6 | 81.0 | 91.1 | 97.7 | 6.7 | yes, yes |
| 9C | sin | 0 | 4.8* | 31.7 | 58.8 | 77.3 | 89.1 | 98.1 | 5.9 | yes, yes |
| 9C | 0.1N HCl | 0 | 5* | 33 | 61 | 80 | 90 | 96 | 6.7 | yes, yes | sgn means simulated gastric fluid, pH 1.2
sin means simulated intestinal fluid, pH 7.5
*means sample analyzed at 1 hour instead of 2 hours
n = 3–6 tablets

Example 11

Simulated Sustained-release Delivery Input Rates and Doses Which Give Maximum 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Concentrations <80% of Immediate Release and Exceed a Minimum Effective Plasma Concentration, $C_{min}$, of 2 ng/ml.

This example illustrates the process for simulating active compound delivery input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that give maximum plasma concentrations not more than 80% of an equivalent immediate release bolus dose and greater than a minimum effective concentration of 2 ng/ml ($C_{min}$). For some indications, a lower plasma concentration may be adequate for therapy. The sustained release profile is simulated as a zero-order release through hourly pulses of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate over the specified release duration. For example, a hypothetical sustained release (SR) formulation that delivered the dose by zero-order for 6 hours was approximated by the pulsed hourly administration of ⅙ of the total dose at 0, 1, 2, 3, 4, and 5 hours. In these simulations, the two variables studied included the dosage strengths from 4 to 48 mg and sustained release durations from 4 to 18 hours. The resulting maximum 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentration simulated for each of these sustained release dosage forms, $C_{max,sr}$, are reported in Tables 11-1 to 11-7 for dosage strengths of 4, 6, 8, 12, 16, 24, and 48 mg, respectively. These results were evaluated according to the criteria specified above: $C_{max,sr}$ not more than 80% $C_{max,ir}$, and plasma concentration greater than $C_{min}$ at any time. Those examples that meet both criteria, and reported as "yes" in the tables are embodiments of this invention. (IR refers to immediate release dosing, and SR refers to sustained release dosing.)

Methods

A one compartment pharmacokinetic model was constructed using the following equations (I Think, Stella, HPS, Hanover, N.H.):

active compound_at_absn_site(t)=compound_at_absn_site(t−dt)+(dosing−absorption)*dt
INIT active compound_at_absn_site=0
dosing=pulse(dose*ba,0,999)
absorption=active compound_at_absn_site*ka_$_{hr}$1
active compound_in_plasma_mg(t)=active compound_in_plasma_mg(t−dt)+(absorption−elimination)*dt
INIT active compound_in_plasma_mg=0
absorption=active compound_at_absn_site*ka_hr1
elimination=elim_rate_const*active compound_in_plasma_mg
active compound_in_urine(t)=active compound_in_urine(t−dt)+(elimination)*dt
INIT active compound_in_urine=0
elimination=elim_rate_const*active compound_in_plasma_mg
ba=1
dose=0.3
elim_rate_const=0.693/thalf_hr
ka_hr1=1.3
plasma_conc_ugml=active compound_in_plasma_mg/Vdist_liter
thalf_hr=2.5
Vdist_liter=0.75 where ba is bioavailability (1.0), Vdist_liter is volume of distribution in units of liters (0.75), ka_hr1 is absorption rate constant in units of reciprocal hr (1.3), and thalf_hr is the plasma concentration vs. time elimination half-life in units of hr (2.5). All other equations are basic pharmacokinetic relationships (M. Gibaldi and D. Perrier, *Pharmacokinetics*, $2^{nd}$ Ed. "Active Compounds And The Pharmaceutical Sciences", Editor: J. Swarbrick, Vol. 15, 1982, NY, Marcel Dekker, Inc.).

The bioavailability, volume of distribution, half-life and absorption rate constant were varied until the simulated plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate concentrations agreed reasonably well with the average observed plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate concentrations following oral administration of 10, 3 and 0.3 mg doses to humans. These parameters were then fixed to the values noted above for all subsequent simulations.

The validated model was then exported to the software Madonna for Windows (6.0, Robert I. Macey & George F. Oster, Berkeley, Calif.) as a text file. This is a specialized program which can perform multiple simulations using models created in I Think and Stella. Multiple simulations of IR formulations at doses of 4, 8, 12, 16, 18, 24 and 48 mg were completed. The maximum plasma concentration ($C_{max}$) was read from the graph. The times at which the simulated plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate concentration first exceeded 2 ng/ml (T1) and then subsequently fell below 2 ng/ml (T2) were also read from the graph. The difference between these two values represented the time during which plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate concentrations were >2 ng/ml ($\Delta T_{T2−T1}$). These values of $C_{max}$ and $\Delta T_{ir}$ after IR administration were then compared to corresponding values after simulations of SR formulations and after IR/SR hybrid formulations. The remainder of this Example, and Examples 12–14 describe the difference in $C_{max}$ and $\Delta T$ among these formulations.

The model was then further modified to allow the simulation of plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate release following oral administration of hypothetical SR formulations. The zero-order delivery by these hypothetical formulations were approximated through hourly pulses of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate. For example, a hypothetical SR formulation which delivered the dose by zero-order for 6 hr was approximated by the pulsed hourly administration of ⅙ of the total dose at 0, 1, 2, 3, 4 and 5 hr. This was accomplished with the addition of the following equations:

Tend=6
mr=pulse(dose/(Tend),0,1)
dosing=if time<(Tend−1) then mr else 0 where Tend is the hypothetical time when 100% of the dose was delivered (e.g., 6 hr).

Results

The simulation results were evaluated according to the following criteria: i) the maximum concentration following sustained release dosing of 2-amino-N-[2-(3a-(R)-benzyl-2-methyl-3-oxo-2,3,3a ,4,6,7-hexahydro-pyrazolo[4,3-c]pyridin-5-yl)-1-(R)-benzyloxymethyl-2-oxo-ethyl]-isobutyramide L-tartrate must be no more than 80% of an equivalent immediate release bolus; and ii) the plasma concentration must exceed a minimum effective concentration of 2 ng/ml at any time after dosing. Both of these criteria must be satisfied in order for the simulated profile to exemplify an embodiment of this invention.

The data in Tables 11-1 through 11-7 demonstrate the zero order release rates, in mg/kg/hr, of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms, where kg refers to the weight of the patient. The zero order release rate was calculated from the dosing rate for a 70 kg human. The simulation results are illustrated in Tables 11-1 to 11-7 for dosage strengths of 4, 6, 8, 12, 16, 24, and 48 mg, respectively.

For the 4 mg dose, release rates of 4 to 10 hours were simulated and evaluated according to the above specified criteria (Table 11-1). For this case, the above model would simulate the plasma-time profile after the oral administration of 6 hourly pulses of 0.67 mg each. The $C_{max}$ simulated for a 6 hr SR formulation of 4 mg was 2.5 ng/ml. The dosing rate per 70 kg human for this 4 mg dose delivered over 6 hr=4 mg/6 hr/70 kg=0.010 mg/hr/kg. For the 4 mg dose, zero order release rates of 0.007 to 0.010 mg/kg/hr, or 6 to 8 hr SR durations, meet both the in vivo criteria and are embodiments of this invention.

TABLE 11-1

Zero Order Release Rates Of 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate From Sustained Release Dosage Forms That Result In No More Than 80% Of The Maximum Plasma Concentration Produced By An Equivalent Dose Of Immediate Release Bolus (IR Dose = 4 mg With $C_{max}$ = 3.5 ng/ml) And Above $C_{min}$ (2 ng/ml).

| Zero-Order Release Rate (mg/hr/kg) | Sustained Release Duration (hrs) | $C_{max, sr}$ (ng/ml) | $C_{max, sr}$ < 80% $C_{max, ir}$ | C > $C_{min}$ |
|---|---|---|---|---|
| 0.006 | 10 | 1.8 | yes | no |
| 0.007 | 8 | 2.1 | yes | yes |
| 0.010 | 6 | 2.5 | yes | yes |
| 0.014 | 4 | 2.9 | no | yes |

Similarly, simulations for the 6 mg dose delivered over 4 to 14 hour resulted in the values of $C_{max}$ listed in Table 11-2. For the 6 mg dose, zero order release rates of 0.007 to 0.014 mg/kg/hr, or 12 to 6 hr SR durations, meet both the in vivo criteria and are embodiments of this invention.

TABLE 11-2

Zero Order Release Rates Of 2-Amino-N-2-[3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate From Sustained Release Dosage Forms That Result In No More Than 80% Of The Maximum Plasma Concentration As An Equivalent Dose Of Immediate Release Bolus (IR Dose = 6 mg With $C_{max}$ = 5.4 ng/ml) And Above $C_{min}$ (2 ng/ml).

| Zero-Order Release Rate (mg/hr/kg) | Sustained Release Duration (hrs) | $C_{max,sr}$ (ng/ml) | $C_{max,sr}$ < 80% $C_{max,ir}$ | C > $C_{min}$ |
|---|---|---|---|---|
| 0.0061 | 14 | 1.9 | yes | no |
| 0.0071 | 12 | 2.3 | yes | yes |
| 0.009 | 10 | 2.7 | yes | yes |
| 0.011 | 8 | 3.2 | yes | yes |
| 0.014 | 6 | 3.7 | yes | yes |
| 0.021 | 4 | 4.4 | no | yes |

Similarly, simulations for the 8 mg dose delivered over 4 to 20 hr resulted in the values of $C_{max}$ listed in Table 11-3. For the 8 mg dose, zero order release rates of 0.0063 to 0.019 mg/kg/hr, or 18 to 6 hr SR durations, meet both the in vivo criteria and are embodiments of this invention.

TABLE 11-3

Zero Order Release Rates Of 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate From Sustained Release Dosage Forms That Result In No More Than 80% Of The Maximum Plasma Concentration As An Equivalent Dose Of Immediate Release Bolus (IR Dose = 8 mg With $C_{max}$ = 7.0 ng/ml) And Above $C_{min}$ (2 ng/ml).

| Zero-Order Release Rate (mg/hr/kg) | Sustained Release Duration (hrs) | $C_{max,sr}$ (ng/ml) | $C_{max,sr}$ < 80% $C_{max,ir}$ | C > $C_{min}$ |
|---|---|---|---|---|
| 0.0057 | 20 | 1.8 | yes | no |
| 0.0063 | 18 | 2.2 | yes | yes |
| 0.008 | 14 | 2.7 | yes | yes |
| 0.011 | 10 | 3.6 | yes | yes |
| 0.019 | 6 | 5.0 | yes | yes |
| 0.029 | 4 | 5.9 | no | yes |

Similarly, simulations for the 12 mg dose delivered over 4 to 18 hr resulted in the values of $C_{max}$ listed in Table 11-4. For the 12 mg dose, zero order release rates of 0.010 to 0.029 mg/kg/hr, or 18 to 6 hr SR durations, meet both the in vivo criteria and are embodiments of this invention. In this case, some lower release rates will also embody the invention. These lower release rates may be determined using the simulation methodology described in these Examples.

TABLE 11-4

Zero Order Release Rates Of 2-Amino-N-[2-(3a-(R)-benzyl-2-methyl-3-oxo-2,3,3a,4,6,7-hexahydro-pyrazolo[4,3-C]pyridin-5-yl)-1-(R)-benzyloxymethyl-2-oxo-ethyl]-isobutyramide L-tartrate From Sustained Release Dosage Forms That Result In No More Than 80% Of The Maximum Plasma Concentration As An Equivalent Dose Of Immediate Release Bolus (IR Dose = 12 mg With $C_{max}$ = 10.8 ng/ml) And Above $C_{min}$ (2 ng/ml).

| Zero-Order Release Rate (mg/hr/kg) | Sustained Release Duration (hrs) | $C_{max,sr}$ (ng/ml) | $C_{max,sr}$ < 80% $C_{max,ir}$ | C > $C_{min}$ |
|---|---|---|---|---|
| 0.010 | 18 | 3.2 | yes | yes |
| 0.012 | 14 | 4.1 | yes | yes |

TABLE 11-4-continued

Zero Order Release Rates Of 2-Amino-N-[2-(3a-(R)-benzyl-2-methyl-
3-oxo-2,3,3a,4,6,7-hexahydro-pyrazolo[4,3-C]pyridin-5-yl)-1-(R)-
benzyloxymethyl-2-oxo-ethyl]-isobutyramide L-tartrate From Sustained
Release Dosage Forms That Result In No More Than 80% Of The
Maximum Plasma Concentration As An Equivalent
Dose Of Immediate Release Bolus
(IR Dose = 12 mg With $C_{max}$ = 10.8 ng/ml) And Above $C_{min}$(2 ng/ml).

| Zero-Order Release Rate (mg/hr/kg) | Sustained Release Duration (hrs) | $C_{max,sr}$ (ng/ml) | $C_{max,sr} <$ 80% $C_{max,ir}$ | $C > C_{min}$ |
|---|---|---|---|---|
| 0.017 | 10 | 5.4 | yes | yes |
| 0.029 | 6 | 7.5 | yes | yes |
| 0.043 | 4 | 8.9 | no | yes |

Similarly, simulations for the 16 mg dose delivered over 4 to 18 hr resulted in the values of $C_{max}$ listed in Table 11-5. For the 16 mg dose, zero order release rates of 0.013 to 0.038 mg/kg/hr, or 18 to 6 hr SR durations, meet both the in vivo criteria and are embodiments of this invention. In this case, some lower release rates will also embody the invention. These lower rates may be determined using the simulation methodology described in these Examples.

TABLE 11-5

Zero Order Release Rates Of 2-Amino-n-[2-(3a-(R)-benzyl-2-methyl-
3-oxo-2,3,3a,4,6,7-hexahydro-pyrazolo[4,3-c]pyridin-5-yl)-1-(R)-
benzylozmethyl-2-oxo-ethyl]-isobutyramide L-tartrate From
Sustained Release Dosage Forms That Results In No More Than
80% Of The Maximum Plasma Concentration As An Equivalent
Dose Of Immediate Release Bolus
(IR dose = 16 mg with $C_{max}$ = 14.0 ng/ml) and above $C_{min}$(2 ng/ml).

| Zero-Order Release Rate (mg/hr/kg) | Sustained Release Duration (hrs) | $C_{max,sr}$ (ng/ml) | $C_{max,sr} <$ 80% $C_{max,ir}$ | $C > C_{min}$ |
|---|---|---|---|---|
| 0.013 | 18 | 4.3 | yes | yes |
| 0.016 | 14 | 5.4 | yes | yes |
| 0.023 | 10 | 7.2 | yes | yes |
| 0.038 | 6 | 10.0 | yes | yes |
| 0.057 | 4 | 11.8 | no | yes |

Similarly, simulations for the 24 mg dose delivered over 4 to 18 hr resulted in the values of $C_{max}$ listed in Table 11-6. For the 24 mg dose, zero order release rates of at least 0.019 to 0.057 mg/kg/hr, or 18 to 6 hr SR durations, meet both the in vivo criteria and are embodiments of this invention. In this case, some lower release rates will also embody the invention. These lower rates may be determined using the simulation methodology described in these Examples.

TABLE 11-6

Zero Order Release Rates Of 2-Amino-n-[2-(3a-(R)-benzyl-2-
methyl-3-oxo-2,3,3a,4,6,7-hexahydro-pyrazolo[4,3-c]pyridin-5-yl)-
1-(R)-benzyloxymethyl-2-oxo-ethyl]-isobutyramide L-tartrate From
Sustained Release Dosage Forms That Results In No More Than
80% Of The Maximum Plasma Concentration As An Equivalent
Dose Of Immediate Release Bolus
(IR dose = 24 mg with $C_{max}$ = 21.6 ng/ml) and above $C_{min}$(2 ng/ml).

| Zero-Order Release Rate (mg/hr/kg) | Sustained Release Duration (hrs) | $C_{max,sr}$ (ng/ml) | $C_{max,sr} <$ 80% $C_{max,ir}$ | $C > C_{min}$ |
|---|---|---|---|---|
| 0.019 | 18 | 6.4 | yes | yes |
| 0.024 | 14 | 8.1 | yes | yes |
| 0.034 | 10 | 10.8 | yes | yes |

TABLE 11-6-continued

Zero Order Release Rates Of 2-Amino-n-[2-(3a-(R)-benzyl-2-
methyl-3-oxo-2,3,3a,4,6,7-hexahydro-pyrazolo[4,3-c]pyridin-5-yl)-
1-(R)-benzyloxymethyl-2-oxo-ethyl]-isobutyramide L-tartrate From
Sustained Release Dosage Forms That Results In No More Than
80% Of The Maximum Plasma Concentration As An Equivalent
Dose Of Immediate Release Bolus
(IR dose = 24 mg with $C_{max}$ = 21.6 ng/ml) and above $C_{min}$(2 ng/ml).

| Zero-Order Release Rate (mg/hr/kg) | Sustained Release Duration (hrs) | $C_{max,sr}$ (ng/ml) | $C_{max,sr} <$ 80% $C_{max,ir}$ | $C > C_{min}$ |
|---|---|---|---|---|
| 0.057 | 6 | 15.0 | yes | yes |
| 0.086 | 4 | 17.7 | no | yes |

Similarly, simulations for the 48 mg dose delivered over 4 to 18 hr resulted in the values of $C_{max}$ listed in Table 11-7. For the 48 mg dose, zero order release rates of at least 0.038 to 0.114 mg/kg/hr, or 18 to 6 hr SR durations, meet both the in vivo criteria and are embodiments of this invention. In this case, some lower release rates will also embody the invention. These lower rates may be determined using the simulation methodology described in these Examples.

TABLE 11-7

Zero Order Release Rates Of 2-Amino-n-[2-(3a-(R)-benzyl-2-methyl-
3-oxo-2,3,3a,4,6,7-hexahydro-pyrazolo[4,3-c]pyridin-5-yl)-1-(R)-
benzyloxymethyl-2-oxo-ethyl]-isobutyramide L-tartrate From Sustained
Release Dosage Forms That Result In No More Than 80% Of The
Maximum Plasma Concentration As An Equivalent
Dose Of Immediate Release Bolus
(IR dose = 48 mg with $C_{max}$ = 42.2 ng/ml) and above $C_{min}$(2 ng/ml).

| Zero-Order Release Rate (mg/hr/kg) | Sustained Release Duration (hrs) | $C_{max,sr}$ (ng/ml) | $C_{max,sr} <$ 80% $C_{max,ir}$ | $C > C_{min}$ |
|---|---|---|---|---|
| 0.038 | 18 | 13.0 | yes | yes |
| 0.049 | 14 | 16.4 | yes | yes |
| 0.069 | 10 | 21.7 | yes | yes |
| 0.114 | 6 | 30.0 | yes | yes |
| 0.171 | 4 | 35.4 | no | yes |

Exemplary sustained release durations of 2-amino-N-[2-(3a-(R)-benzyl-2-methyl-3-oxo-2,3,3a ,4,6,7-hexahydro-pyrazolo[4,3-c]pyridin-5-yl)-1-(R)-benzyloxymethyl-2-oxo-ethyl]-isobutyramide L-tartrate delivered from sustained release dosage forms, based on these simulations, are about 6 to about 8 hours for about a 4 mg dose, about 6 to about 12 hours for about a 6 mg dose, about 6 to about 18 hours for doses of about 8,12, 16, 24 and 48 mg.

Exemplary in vivo input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from sustained release dosage forms, based on these simulations, are about 0.007 to about 0.010 mg/hr/kg for about a 4 mg dose, about 0.007 to about 0.014 mg/hr/kg for about a 6 mg dose, about 0.006 to about 0.019 mg/hr/kg for about an 8 mg dose, about 0.010 to about 0.029 mg/hr/kg for about a 12 mg dose, about 0.013 to about 0.038 mg/hr/kg for about a 16 mg dose, about 0.019 to about 0.057 mg/hr/kg for about a 24 mg dose, and about 0.038 to about 0.114 mg/hr/kg for about a 48 mg dose.

Exemplary zero order in vitro release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from sustained release dosage forms, based on these simulations, are about 0.50 to about 0.67 mg/hr for about a 4 mg dose, about 0.50 to about 1.00 mg/hr for about a 6 mg dose, about 0.44 to about 1.33 mg/hr for about an 8 mg dose, about 0.67 to about 2.00 mg/hr for about a 12 mg dose, about 0.89 to about 2.67 mg/hr for about a 16 mg dose, about 1.33 to about 4.00 mg/hr for about a 24 mg dose, and about 2.67 to about 8.00 mg/hr for about a 48 mg dose, for a 70 kg patient, such as a human patient. Exemplary release rates may be computed similarly for patients with different weights.

Example 12

Simulated Sustained-release Delivery Input Rates and Doses Which Maintain 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Concentrations Above 2 ng/ml for a Length of Time Longer Than Immediate Release This example illustrates the process for simulating active compound delivery input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms which maintain concentrations above 2 ng/ml for a length of time longer than an equivalent immediate release dose by at least 30 minutes. The sustained release profile is simulated as a zero-order release through hourly pulses of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate over the specified release duration. In these simulations, the two variables studied included the dosage strengths from 6 to 48 mg and sustained release durations from 4 to 18 hours. The resulting duration over which 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentrations exceed the $C_{min}$, $\Delta T_{sr}$, is reported in Tables 12-1 to 12-6 for dosage strengths of 6, 8, 12, 16, 24, and 48 mg, respectively. These results were evaluated according to the criteria specified above: $\Delta T_{sr}$ not less than 30 minutes longer than $\Delta T_{ir}$. The examples that meet this criteria, and reported as 'yes' in the tables are embodiments of this invention.

For some therapeutic indications, the minimum effective 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentration may be lower than 2 ng/ml, e.g., 1 ng/ml. The simulation methodology may be used to determine active compound delivery rates which meet the $\Delta T$ criterion for any appropriate minimum effective concentration.

Methods

Using the same methods as described to create the simulations for Example 11, the difference between the time at which the simulated plasma 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate concentration first exceeded 2 ng/ml and then subsequently fell below 2 ng/ml ($\Delta T_{sr}$) were tabulated for the sustained release input rates.

Results

The simulation results were evaluated according to the following criterion. The time during which 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentrations were above the minimum effective concentration of 2 ng/ml for the sustained release dosage form exceeded an equivalent dose of immediate release bolus by at least 30 minutes.

The data in Tables 12-1 through 12-6 demonstrate the zero order release rates, in mg/kg/hr, of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms. The zero order release rate was calculated from the dosing rate for a 70 kg human. The simulation results are illustrated in Tables 12-1 to 12-6 for dosage strengths of 6, 8, 12, 16, 24, and 48 mg, respectively.

For the 6 mg dose, release rates of 2 to 14 hours were simulated and evaluated according to the above specified criteria (Table 12-1). The $\Delta T_{sr}$ simulated for a 6 hr SR duration was 6.5 hrs, which exceeded the $\Delta T_{ir}$=5.6 hr by 0.9 hrs. For the 6 mg dose, zero order release rates of 0.009 to 0.021 mg/kg/hr, or 10 to 4 hr SR durations, meet both the in vivo criteria and are embodiments of this invention.

TABLE 12-1

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 6 mg with $\Delta T_{ir}$ = 5.6 hr and $\Delta T_{sr}$ > 6.1 hr) and above $C_{min}$(2 ng/ml).

| Zero-Order Release Rate (mg/hr/kg) | Sustained Release Duration (hrs) | $\Delta T_{sr}$ C > Cmin (hrs) | $\Delta T_{sr}$ > $\Delta T_{ir}$ + 0.5 |
|---|---|---|---|
| 0.006 | 14 | 0.7 | no |
| 0.009 | 10 | 6.9 | yes |
| 0.011 | 8 | 6.8 | yes |
| 0.014 | 6 | 6.5 | yes |
| 0.021 | 4 | 6.2 | yes |
| 0.043 | 2 | 5.9 | no |

For the 8 mg dose, release rates of 2 to 20 hours were simulated and evaluated according to the above specified criteria (Table 12-2). The zero order release rates for the 8 mg dose of 0.0063 to 0.029 mg/kg/hr, or 18 to 4 hr SR durations, meet both the in vivo criteria and are embodiments of this invention.

TABLE 12-2

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 8 mg with $\Delta T_{ir}$ = 6.8 hr and $\Delta T_{sr}$ > 7.3 hr) and above $C_{min}$(2 ng/ml).

| Zero-Order Release Rate (mg/hr/kg) | Sustained Release Duration (hrs) | $\Delta T_{sr}$ C > Cmin (hrs) | $\Delta T_{sr}$ > $\Delta T_{ir}$ + 0.5 |
|---|---|---|---|
| 0.0057 | 20 | 6 | no |
| 0.0063 | 18 | 10.4 | yes |
| 0.008 | 14 | 10.2 | yes |
| 0.011 | 10 | 9.5 | yes |
| 0.014 | 8 | 8.9 | yes |
| 0.029 | 4 | 7.4 | yes |
| 0.057 | 2 | 7.2 | no |

For the 12 mg dose, release rates of 4 to 18 hours were simulated and evaluated according to the above specified criteria (Table 12-3). The zero order release rates for the 12 mg dose of at least 0.010 to 0.043 mg/kg/hr, or 18 to 4 hr SR durations, meet both the in vivo criteria and are embodiments of this invention. Some release rates and durations outside this range will also embody the invention. These may be determined using the simulation methodology described here.

TABLE 12-3

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 12 mg with $\Delta T_{ir}$ = 8.3 hr and $\Delta T_{sr}$ > 8.8 hr) and above $C_{min}$ (2 ng/ml).

| Zero-Order Release Rate (mg/hr/kg) | Sustained Release Duration (hrs) | $\Delta T_{sr}$ C > Cmin (hrs) | $\Delta T_{sr}$ > $\Delta T_{ir}$ + 0.5 |
|---|---|---|---|
| 0.010 | 18 | 16.0 | yes |
| 0.012 | 14 | 14.2 | yes |
| 0.017 | 10 | 12.0 | yes |
| 0.021 | 8 | 11.3 | yes |
| 0.043 | 4 | 9.4 | yes |

For the 16 mg dose, release rates of 4 to 18 hours were simulated and evaluated according to the above specified criteria (Table 12-4). The zero order release rates for the 16 mg dose of at least 0.013 to 0.057 mg/kg/hr, or 18 to 4 hr SR durations, meet both the in vivo criteria and are embodiments of this invention. Some release rates and durations outside this range will also embody the invention. These may be determined using the simulation methodology described here.

TABLE 12-4

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 16 mg with $\Delta T_{ir}$ = 9.3 hr and $\Delta T_{sr}$ > 9.8 hr) and above $C_{min}$ (2 ng/ml).

| Zero-Order Release Rate (mg/hr/kg) | Sustained Release Duration (hrs) | $\Delta T_{sr}$ C > $C_{min}$ (hrs) | $\Delta T_{sr}$ > $\Delta T_{ir}$ + 0.5 |
|---|---|---|---|
| 0.013 | 18 | 18.5 | yes |
| 0.016 | 14 | 15.9 | yes |
| 0.023 | 10 | 13.7 | yes |
| 0.029 | 8 | 12.5 | yes |
| 0.057 | 4 | 10.6 | yes |

For the 24 mg dose, release rates of 4 to 18 hours were simulated and evaluated according to the above specified criteria (Table 12-5). The zero order release rates for the 24 mg dose of at least 0.019 to 0.086 mg/kg/hr, or 18 to 4 hr SR durations, meet both the in vivo criteria and are embodiments of this invention. Some release rates and durations outside this range will also embody the invention. These may be determined using the simulation methodology described here.

TABLE 12-5

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 24 mg with $\Delta T_{ir}$ = 10.8 hr and $\Delta T_{sr}$ > 11.3 hr) and above $C_{min}$ (2 ng/ml).

| Zero-Order Release Rate (mg/hr/kg) | Sustained Release Duration (hrs) | $\Delta T_{sr}$ C > $C_{min}$ (hrs) | $\Delta T_{sr}$ > $\Delta T_{ir}$ + 0.5 |
|---|---|---|---|
| 0.019 | 18 | 20.9 | yes |
| 0.024 | 14 | 18.2 | yes |
| 0.034 | 10 | 15.4 | yes |
| 0.043 | 8 | 14.4 | yes |
| 0.086 | 4 | 12.3 | yes |

For the 48 mg dose, release rates of 2 to 20 hours were simulated and evaluated according to the above specified criteria (Table 12-6). The zero order release rates for the 48 mg dose of at least 0.034 to 0.343 mg/kg/hr, or 20 to 2 hr SR durations, meet both the in vivo criteria and are embodiments of this invention. Some release rates and durations outside this range will also embody the invention. These may be determined using the simulation methodology described here.

TABLE 12-6

Zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from sustained release dosage forms that result in plasma concentrations above 2 ng/ml for durations exceeding an equivalent dose of immediate release bolus by at least 30 minutes (dose = 48 mg with $\Delta T_{ir}$ = 13.4 hr and $\Delta T_{sr}$ > 13.9 hr) and above $C_{min}$ (2 ng/ml).

| Zero-Order Release Rate (mg/hr/kg) | Sustained Release Duration (hrs) | $\Delta T_{sr}$ C > $C_{min}$ (hrs) | $\Delta T_{sr}$ > $\Delta T_{ir}$ + 0.5 |
|---|---|---|---|
| 0.034 | 20 | 26.0 | yes |
| 0.038 | 18 | 24.4 | yes |
| 0.049 | 14 | 21.4 | yes |
| 0.069 | 10 | 18.7 | yes |
| 0.086 | 8 | 17.4 | yes |
| 0.171 | 4 | 14.9 | yes |
| 0.343 | 2 | 14.1 | yes |

Exemplary sustained release durations of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxmethyl-2-oxo-ethyl]-isobutyramide L-tartrate delivered from sustained release dosage forms, based on these simulations, are about 4 to about 10 hours for about a 6 mg dose, about 4 to about 18 hours for about 8, 12, 16, and 24 mg doses, and about 2 to about 20 hours for about a 48 mg dose.

Exemplary zero order release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from sustained release dosage forms, based on these simulations, are about 0.009 to about 0.021 mg/hr/kg for about a 6 mg dose, about 0.006 to about 0.029 mg/hr/kg for about an 8 mg dose, about 0.010 to about 0.043 mg/hr/kg for about a 12 mg dose, about 0.013 to about 0.057 mg/hr/kg for about a 16 mg dose, about 0.019 to about 0.086 mg/hr/kg for about a 24 mg dose, and about 0.034 to about 0.343 mg/hr/kg for about a 48 mg dose Exemplary zero order in vitro release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from sustained release dosage forms, based on these simulations, are about 0.60 to about 1.50 mg/hr for about a 6 mg dose, about 0.44 to about 2.00 mg/hr for an 8 mg dose, about 0.67 to about 3.00 mg/hr for about a 12 mg dose, about 0.89 to about 4.00 mg/hr for about a 16 mg dose, about 1.33 to about 6.00 mg/hr for about a 24 mg dose, and about 2.40 to about 24.00 mg/hr for about a 48 mg dose, when computed for a 70 kg patient, such as a human patient. Exemplary release rates may be computed similarly for patients of different weights.

Example 13

Simulated Immediate Release Plus Sustained-release Delivery Input Rates and Doses Which Give Maximum 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Concentrations <80% of Immediate Release and Exceed a Minimum Therapeutic Plasma Concentration, $C_{min}$, of 2 ng/ml This example illustrates the process for simulating delivery input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from immediate plus sustained release dosage forms that give maximum plasma concentrations not more than 80% of an equivalent immediate release bolus dose and greater than a minimum therapeutic concentration of 2 ng/ml. For some indications, a lower minimum plasma concentration, e.g., 1 ng/ml, may be efficacious. The sustained release profile is simulated as a zero-order release through hourly pulses of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate over the specified release duration. The immediate release portion of the dose is completely input at time zero. In these simulations, the three variables studied included the fraction of dose delivered as an immediate release bolus from about 5.0 to about 75%, the dosage strengths from about 4 to about 48 mg, and the sustained release durations from about 4 to about 18 hours. The resulting maximum 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentration simulated for each of these immediate plus sustained release dosage forms, $C_{max,ir+sr}$, are reported in Tables 13-1 to 13-4 for dosage strengths of 4, 6, 12, and 48 mg, respectively. These results were evaluated according to the criteria specified above: $C_{max,ir+sr}$ not more than 80% $C_{max,ir}$, and plasma concentration greater than $C_{min}$ at any time. Those examples that meet both criteria, and reported as 'yes' in the tables are embodiments of this invention.

Methods

Using the same methods as described to create the simulations for example 11, the following equations were added to the model to allow simultaneous input of both IR and SR components:

dose=10
Tend=4
ir_fraction=0.75
ir_dose=ir_fraction*dose
mr_dose=dose*(1−ir_fraction)
ir=pulse(be*ir_dose,0,999)

interval_dose=mr_dose/Tend
mr=pulse(interval_dose,0,1)

dosing=if time<Tend−1 then ir+mr else 0 where dose and Tend are defined above, ir_fraction is the fraction of the total dose which was formulated as IR, ir_dose is that IR dose, mr_dose is the remainder of the dose formulated as SR, ir is the pulse dosing of the entire IR dose (at time=0, i.e. immediately upon administration), interval_dose is the hourly dose administered as an hourly pulse during the period the SR formulation delivers, mr is the hourly pulse dosing during which time the SR formulation delivers, dosing is the combined delivery of the IR and SR formulations. In the above example, a 10 mg dose is simulated with 7.5 mg as IR, and 2.5 mg as SR delivered over 4 hr.

Results

The simulation results were evaluated according to the following criteria: i) the maximum concentration following immediate plus sustained release dosing of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate must be no more than 80% of the maximum active compound plasma concentration after dosing an immediate release bolus at the same dose; and ii) the plasma concentration must exceed a minimum effective concentration of 2 ng/ml at any time after dosing. Both of these criteria must be satisfied in order for the simulated profile to exemplify an embodiment of this invention, for indications requiring a 2 ng/ml minimum plasma active compound concentration for efficacy. For some therapeutic indications, a lower active compound plasma concentration, e.g., 1 ng/ml, may be sufficient for efficacy. The simulation methodology can be used to determine IR/SR dosage form characteristics for such therapeutic indications.

As described for Example 11, the maximum plasma concentration ($C_{max}$) was tabulated. Table 13-1 lists the $C_{max}$ values for simulations where a 4 mg dose was delivered from a hybrid IR/SR dosage form with varying fractions of dose delivered by IR and SR. For the 4 mg dose in which sustained release duration is 4 hours, the zero order sustained release rates of 0.007 to 0.014 mg/hr/kg obtained from IR percentages of about 50 to about 5% meet both of the in vivo criteria and are embodiments of this invention. Sustained release durations of 6, 8, 10, 12, 16 and 18 hours were also simulated according to the method described above. For each SR release duration, the % of IR dose and SR release rates that meet the specified criteria vary and are detailed in Table 13-1. For the 6 hr SR duration, the SR release rates of about 0.005 to about 0.009 mg/hr/kg obtained from IR percentages of about 50 to about 5% meet the criteria and are embodiments of this invention. For the 8 and 10 hr SR durations, the zero order release rates of about 0.002–0.004 and about 0.001–0.003 mg/hr/kg obtained from IR percentages of about 75 to about 50% meet the criteria and are embodiments of this invention. For the 12, 16, and 18 hr SR durations, of the simulated IR percentages, only the 75% IR dosing meet the criteria.

TABLE 13-1

Fraction of
2-amino-N-[2-(3a-(R)-benzyl-2-methyl-3-oxo-2,3,3a,4,6,7-hexahydro-
pyrazolo[4,3-c]pyridin-5-yl)-
1-(R)-benzyloxymethyl-2-oxo-ethyl]-isobutyramide L-
tartrate dose delivered as immediate
release from a IR/SR hybrid dosage form that results
in plasma concentrations no more than 80% of the maximum plasma
concentration produced by an equivalent dose of immediate release bolus
(dose = 4 mg with $C_{max}$ = 3.5 ng/ml).

| SR Duration (hrs) | Fraction of Dose as IR | Sustained Release Rate (mg/hr/kg) | $C_{max,ir+sr}$ (ng/ml) | $C_{max,ir+sr} <= 80\% \, C_{max,ir}$ | $C > C_{min}$ |
|---|---|---|---|---|---|
| 4  | 0.05 | 0.014 | 2.2  | yes | yes |
| 4  | 0.50 | 0.007 | 2.7  | yes | yes |
| 4  | 0.75 | 0.004 | 3.0  | no  | yes |
| 6  | 0.05 | 0.009 | 2.4  | yes | yes |
| 6  | 0.50 | 0.005 | 2.3  | yes | yes |
| 6  | 0.75 | 0.002 | 2.9  | no  | yes |
| 8  | 0.05 | 0.007 | 2    | yes | no  |
| 8  | 0.50 | 0.004 | 2.1  | yes | yes |
| 8  | 0.63 | 0.003 | 2.5  | yes | yes |
| 8  | 0.75 | 0.002 | 2.8  | yes | yes |
| 10 | 0.05 | 0.005 | 1.7  | yes | no  |
| 10 | 0.50 | 0.003 | 2.1  | yes | yes |
| 10 | 0.75 | 0.001 | 2.8  | yes | yes |
| 12 | 0.05 | 0.005 | <2.0 | yes | no  |
| 12 | 0.50 | 0.002 | 2    | yes | no  |
| 12 | 0.75 | 0.001 | 2.8  | yes | yes |
| 16 | 0.50 | 0.002 | <2.0 | yes | no  |
| 16 | 0.75 | 0.001 | 2.7  | yes | yes |
| 18 | 0.50 | 0.002 | <2.0 | yes | no  |
| 18 | 0.75 | 0.001 | 2.7  | yes | yes |

Table 13-2 lists the $C_{max}$ values for simulations where a 6 mg dose was delivered as a hybrid IR/SR formulation. For the 6 mg dose in which sustained release duration is 4 hours, the zero order sustained release rate of 0.013 mg/hr/kg obtained from an IR percentage of 40% meets both of the in vivo criteria and is an embodiment of this invention. Sustained release durations of 6, 8, 10, 12, 14, 16 and 18 hours were also simulated. For each SR release duration, the % of IR dose and SR release rates that meet the specified criteria vary and are detailed in Table 13-2.

For the 6 mg dose and 6 hr SR duration, the IR percentages of 40 to 5% resulting in SR rates of 0.009–0.014 mg/kg/hr meet the criteria and are embodiments of this invention. For the 8, 10, and 12 hr SR duration, the IR percentages of 75 to 5% result maximum plasma levels that meet the criteria and are embodiments of this invention. For SR durations of 14, 16, and 18 hr, the IR percentages of 75–40% meet the specified criteria.

TABLE 13-2

Fraction of
2-amino-N-[2-(3a-(R)-benzyl-2-methyl-3-oxo-2,3,3a,4,6,7-hexahydro-
pyrazolo[4,3-c]pyridin-5-yl)-
1-(R)-benzyloxymethyl-2-oxo-ethyl]-isobutyramide L-
tartrate dose delivered as immediate
release from a IR/SR hybrid dosage form that results
in plasma concentrations no more than 80% of the maximum plasma
concentration produced by an equivalent dose of immediate release bolus
(dose = 6 mg $C_{max}$ = 5.3 ng/ml).

| SR Duration (hrs) | Fraction of Dose as IR | Sustained Release Rate (mg/hr/kg) | $C_{max,ir+sr}$ (ng/ml) | $C_{max,ir+sr} <= 80\% \, C_{max,ir}$ | $C > C_{min}$ |
|---|---|---|---|---|---|
| 4  | 0.05  | 0.020 | 4.4  | no  | yes |
| 4  | 0.40  | 0.013 | 4.1  | yes | yes |
| 4  | 0.75  | 0.005 | 4.5  | no  | yes |
| 6  | 0.05  | 0.014 | 3.7  | yes | yes |
| 6  | 0.40  | 0.009 | 3.3  | yes | yes |
| 6  | 0.75  | 0.004 | 4.4  | no  | yes |
| 8  | 0.05  | 0.010 | 3.1  | yes | yes |
| 8  | 0.25  | 0.008 | 2.7  | yes | yes |
| 8  | 0.375 | 0.007 | 2.8  | yes | yes |
| 8  | 0.50  | 0.005 | 3.2  | yes | yes |
| 8  | 0.625 | 0.004 | 3.7  | yes | yes |
| 8  | 0.75  | 0.003 | 4.2  | yes | yes |
| 10 | 0.05  | 0.008 | 2.6  | yes | yes |
| 10 | 0.40  | 0.005 | 2.7  | yes | yes |
| 10 | 0.75  | 0.002 | 4.2  | yes | yes |
| 12 | 0.05  | 0.007 | 2.2  | yes | yes |
| 12 | 0.40  | 0.004 | 2.6  | yes | yes |
| 12 | 0.75  | 0.002 | 4.1  | yes | yes |
| 14 | 0.05  | 0.006 | 1.9  | yes | no  |
| 14 | 0.40  | 0.004 | 2.5  | yes | yes |
| 14 | 0.75  | 0.002 | 4.1  | yes | yes |
| 16 | 0.05  | 0.005 | <2.0 | yes | no  |
| 16 | 0.40  | 0.003 | 2.5  | yes | yes |
| 16 | 0.75  | 0.001 | 4.1  | yes | yes |
| 18 | 0.05  | 0.005 | <2.0 | yes | no  |
| 18 | 0.40  | 0.003 | 2.4  | yes | yes |
| 18 | 0.75  | 0.001 | 4.1  | yes | yes |

Table 13-3 lists the $C_{max}$ values for simulations where a 12 mg dose was delivered as a hybrid IR/SR formulation. For the 12 mg dose in which sustained release duration is 4 hours, the zero order sustained release rate of 0.026 mg/hr/kg obtained from an IR percentage of 40% meets both of the in vivo criteria and is an embodiment of this invention. Sustained release durations of 6, 8, 10, 12, 14, 16 and 18 hours were also simulated. For each SR release duration, the % of IR dose and SR release rates that meet the specified criteria vary and are detailed in Table 13-3.

TABLE 13-3

Fraction of 2-amino-N-[2-(3a-(R)-benzyl-2-methyl-3-oxo-2,3,3a,4,6,7-
hexahydropyrazolo[4,3-c]pyridin-5-yl)-1-(R)-benzyloxymethyl-2-oxo-
ethyl]-isobutyramide L-tartrate dose delivered as immediate release
from a IR/SR hybrid dosage form that results in plasma concen-
trations no more than 80% of the maximum plasma concentration
produced by an equivalent dose of immediate release bolus (dose =
12 mg $C_{max}$ = 10.6 ng/ml).

| SR Duration (hrs) | Fraction of Dose as IR | Sustained Release Rate (mg/hr/kg) | $C_{max,ir+sr}$ (ng/ml) | $C_{max,ir+sr} <= 80\% \, C_{max,ir}$ | $C > C_{min}$ |
|---|---|---|---|---|---|
| 4 | 0.05  | 0.041 | 8.7 | no  | yes |
| 4 | 0.40  | 0.026 | 8.2 | yes | yes |
| 4 | 0.75  | 0.011 | 9.0 | no  | yes |
| 6 | 0.05  | 0.027 | 7.4 | yes | yes |
| 6 | 0.40  | 0.017 | 6.5 | yes | yes |
| 6 | 0.75  | 0.007 | 8.7 | no  | yes |
| 8 | 0.05  | 0.020 | 6.1 | yes | yes |
| 8 | 0.25  | 0.016 | 5.4 | yes | yes |
| 8 | 0.375 | 0.013 | 5.6 | yes | yes |

TABLE 13-3-continued

Fraction of 2-amino-N-[2-(3a-(R)-benzyl-2-methyl-3-oxo-2,3,3a,4,6,7-hexahydropyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations no more than 80% of the maximum plasma concentration produced by an equivalent dose of immediate release bolus (dose = 12 mg $C_{max}$ = 10.6 ng/ml).

| SR Duration (hrs) | Fraction of Dose as IR | Sustained Release Rate (mg/hr/kg) | $C_{max,ir+sr}$ (ng/ml) | $C_{max,ir+sr} \leq 80\% C_{max,ir}$ | $C > C_{min}$ |
|---|---|---|---|---|---|
| 8 | 0.50 | 0.011 | 6.5 | yes | yes |
| 8 | 0.625 | 0.008 | 7.4 | yes | yes |
| 8 | 0.75 | 0.005 | 8.5 | no | yes |
| 12 | 0.05 | 0.014 | 4.5 | yes | yes |
| 12 | 0.40 | 0.009 | 5.2 | yes | yes |
| 12 | 0.75 | 0.004 | 8.3 | yes | yes |
| 16 | 0.05 | 0.010 | 3.5 | yes | yes |
| 16 | 0.40 | 0.006 | 4.9 | yes | yes |
| 16 | 0.75 | 0.003 | 8.2 | yes | yes |
| 18 | 0.05 | 0.009 | 3.1 | yes | yes |
| 18 | 0.40 | 0.006 | 4.8 | yes | yes |
| 18 | 0.75 | 0.002 | 8.2 | yes | yes |

Table 13-4 lists the $C_{max}$ values for simulations where a 48 mg dose was delivered as a hybrid IR/SR formulation. For the 48 mg dose in which sustained release duration is 16 hours, the zero order sustained release rates of 0.011 to 0.041 mg/hr/kg obtained from an IR percentage of 75–5% meet both of the in vivo criteria and are an embodiment of this invention.

TABLE 13-4

Fraction of 2-amino-N-[2-(3a-(R)-benzyl-2-methyl-3-oxo-2,3,3a,4,6,7-hexahydropyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations no more than 80% of the maximum plasma concentration produced by an equivalent dose of immediate release bolus (dose = 48 mg $C_{max}$ = 42.2 ng/ml).

| SR Duration (hrs) | Fraction of Dose as IR | Sustained Release Rate (mg/hr/kg) | $C_{max,ir+sr}$ (ng/ml) | $C_{max,ir+sr} \leq 80\% C_{max,ir}$ | $C > C_{min}$ |
|---|---|---|---|---|---|
| 16 | 0.05 | 0.041 | 13.8 | yes | yes |
| 16 | 0.40 | 0.026 | 19.7 | yes | yes |
| 16 | 0.75 | 0.011 | 32.8 | yes | yes |

Exemplary immediate release percentages and sustained release durations of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from immediate plus sustained release dosage forms, based on these simulations, are dependent on dose, sustained release duration and % IR dose. For the about 4 mg dose, exemplary IR percentages and SR durations are about 5 to about 50% for about 4 to about 6 hr SR, about 50 to about 75% for about 8 to about 10 hr SR and about 75% for about 12, 16, and 18 hr SR, respectively. For the about 6 mg dose, exemplary IR percentages and SR durations are about 40% for about 4 hr SR, about 5 to about 40% for about 6 hr SR, about 5 to about 75% for the about 8, 10, and 12 hr SR and about 40 to about 75% for about 14, 16, and 18 hr SR, respectively. For the about 12 mg dose, exemplary IR percentages and SR durations are about 40% for about 4 hr SR, about 5 to about 40% for about 6 hr SR, about 5 to about 62.5% for about 8 hr SR, and about 5 to about 75% for about 12, 16, and 18 hr SR, respectively. For the about 48 mg dose, exemplary IR percentages for the about 16 hr SR duration is about 5 to about 75%.

Exemplary in vivo input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from immediate plus sustained release dosage forms, based on these simulations, are dependent on dose, sustained release duration and % IR dose. For the about 4 mg dose, exemplary in vivo SR input rates are about 0.007 to about 0.014 mg/hr/kg for the about 4 hr SR duration, about 0.005 to about 0.009 mg/hr/kg for the about 6 hr SR duration, about 0.002 to about 0.004 mg/hr/kg for the about 8 hr SR duration, about 0.001 to about 0.003 mg/hr/kg for the about 10 hr SR duration, about 0.001 mg/hr/kg for the about 12, 16, and 18 hr SR duration. For the about 6 mg dose, exemplary in vivo SR input rates are about 0.013 mg/hr/kg for the about 4 hr SR duration, about 0.009 to about 0.014 mg/hr/kg for the about 6 hr SR duration, about 0.003 to about 0.010 mg/hr/kg for the about 8 hr SR duration, about 0.002 to about 0.008 mg/hr/kg for the about 10 hr SR duration, about 0.002 to about 0.007 mg/hr/kg for the about 12 hr SR duration, about 0.002 to about 0.004 mg/hr/kg for the about 14 hr SR duration, about 0.001 to about 0.003 mg/hr/kg for the about 16 and about 18 hr SR durations. For the about 12 mg dose, exemplary in vivo SR input rates are about 0.026 mg/hr/kg for the about 4 hr SR duration, about 0.017 to about 0.027 mg/hr/kg for the about 6 hr SR duration, about 0.008 to about 0.020 mg/hr/kg for the about 8 hr SR duration, about 0.004 to about 0.014 mg/hr/kg for the about 12 hr SR duration, about 0.003 to about 0.010 mg/hr/kg for the about 16 hr SR duration, about 0.002 to about 0.009 mg/hr/kg for the about 18 hr SR duration. For the about 48 mg dose, exemplary in vivo SR input rates for the about 16 hr SR duration are about 0.011 to about 0.041 mg/hr/kg.

Exemplary zero order in vitro release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from immediate plus sustained release dosage forms, are dependent on dose, sustained release duration and % IR dose. The following exemplary % IR dose and in vitro SR active compound release rates are computed for a 70 kg patient. For the about 4 mg dose, exemplary in vitro SR rates are about 0.050 to about 0.95 mg/hr for the about 4 hr SR duration, about 0.33 to about 0.63 mg/hr for the about 6 hr SR duration, about 0.13 to about 0.25 mg/hr for the about 8 hr SR duration, about 0.10 to about 0.20 mg/hr for the about 10 hr SR duration, about 0.08 mg/hr for the about 12, and about 0.06 mg/hr for the about 16, and about 18 hr SR duration. For the about 6 mg dose, exemplary SR rates are about 0.90 mg/hr/kg for the about 4 hr SR duration, about 0.60 to about 0.95 mg/hr for the about 6 hr SR duration, about 0.19 to about 0.71 mg/hr for the about 8 hr SR duration, about 0.15 to about 0.57 mg/hr for the about 10 hr SR duration, about 0.13 to about 0.48 mg/hr for the about 12 hr SR duration, about 0.11 to about 0.26 mg/hr for the about 14 hr SR duration, about 0.09 to about 0.23 mg/hr for the about 16 hr duration and about 0.08 to about 0.20 mg/hr for the about 18 hr SR duration. For the about 12 mg dose, exemplary SR rates are about 1.80 mg/hr for the about 4 hr SR duration, about 1.20 to about 1.90 mg/hr for the about 6 hr SR duration, about 0.56 to about 1.43 mg/hr for the about 8 hr SR duration, about 0.25 to about 0.95 mg/hr for the about 12 hr SR duration, about 0.19 to about 0.71 mg/hr for the about 16 hr SR duration, about 0.17 to about 0.63 mg/hr for the about 18 hr SR duration. For the about 48 mg dose, exemplary SR rates for the about 16 hr SR duration are about 0.75 to about 2.85 mg/hr.

Other exemplary % IR and SR release rate combinations may be identified by utilizing the methodology in this example, for any dose and for a patient of any weight.

Example 14

Simulated Immediate Release Plus Sustained-release Delivery Input Rates and Doses Which Maintain 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Concentrations Above 2 ng/ml for a Length of Time Longer Than Immediate Release This example illustrates the process for simulating active compound delivery input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate from immediate release plus sustained release dosage forms which maintain concentrations above 2 ng/ml for a length of time longer than an equivalent immediate release dose by at least 30 minutes. The sustained release profile is simulated as a zero-order release through hourly pulses of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate over the specified release duration. The immediate release portion of the dose is completely input at time zero. In these simulations, the three variables studied included the fraction of dose delivered as an immediate release bolus from 5.0 to 75%, the dosage strengths from 4 to 48 mg, and the sustained release durations from 4 to 18 hours. The resulting duration that 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentrations exceed the $C_{min}$, $\Delta T_{ir+sr}$, is reported in Tables 14-1 to 14-4 for dosage strengths of 4, 6, 12 and 48 mg, respectively. These results were evaluated according to the criteria specified above: $\Delta T_{ir+sr}$ not less than 30 minutes longer than $\Delta T_{ir}$. The examples that satisfy this criteria, and reported as "yes" in the tables are embodiments of this invention.

Methods

Using the same methods to create the simulations as described for Example 12, the difference between the time at which the 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxmethyl-2-oxo-ethyl]-isobutyramide L-tartrate plasma concentration first exceeded 2 ng/ml and then subsequently fell below 2 ng/ml were tabulated for the immediate plus sustained release input rates ($\Delta T_{ir+sr}$).

Results

The simulation results were evaluated according to the following criterion: the time duration for which 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate plasma concentrations were above the minimum effective plasma concentration of 2 ng/ml for the immediate plus sustained release dosage form exceeded the time above 2 ng/ml for an equivalent dose of immediate release bolus by at least 30 minutes.

For the 4 mg dose, sustained release rates of 4 to 8 hours were simulated with IR dose fractions from 5–75% (Table 14-1). The $\Delta T_{ir+sr}$ simulated for the 4 hr SR duration with 5–50% IR dose fraction was 1.6–4.3 hrs, which fell below the required 4.4 hrs. Therefore, the 4 mg dose delivered as an IR plus SR dosage form with 5–75% IR and 4–8 hr SR duration do not meet the criterion of maintaining active compound plasma concentrations at >2 ng/ml for 30 minutes longer than an immediate release bolus dose. However, some IR/SR combinations in the range of Table 14-1 embody the invention because they meet the $C_{max}$ criterion in Example 13.

TABLE 14-1

Fraction of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations above 2 ng/ml for durations exceeding that for an equivalent dose of immediate release bolus by at least 30 minutes
(dose = 4 mg with $\Delta T_{ir}$ = 3.9 hr and $\Delta T_{ir+sr}$ > 4.4 hr; SR release rate 4, 6, and 8 hr).

| SR Duration (hrs) | Fraction of Dose as IR | Sustained Release Rate (mg/hr/kg) | $\Delta T_{ir+sr}$ C > $C_{min}$ (hrs) | $\Delta T_{ir+sr}$ > $\Delta T_{ir}$ + 0.5 |
|---|---|---|---|---|
| 4 | 0.05 | 0.014 | 1.6 | no |
| 4 | 0.50 | 0.007 | 4.3 | no |
| 6 | 0.05 | 0.009 | 3 | no |
| 6 | 0.50 | 0.005 | 3.8 | no |
| 8 | 0.50 | 0.004 | 2.1 | no |
| 8 | 0.63 | 0.003 | 3.1 | no |
| 8 | 0.75 | 0.002 | 1.5 | no |

Table 14-2 lists the $\Delta T_{ir+sr}$ values for simulations where a 6 mg dose was delivered as a hybrid IR/SR formulation. For the 6 mg dose, release rates of 4 to 12 hours were simulated and evaluated according-to the above specified criteria (Table 14-2). The $\Delta T_{ir+sr}$ simulated for a 4 hr SR duration with 5–40% IR was 6.3–6.5 hrs, which exceeded the $\Delta T_{ir}$=5.6 hr by 0.7–0.9 hrs. The corresponding zero order sustained release rates of 0.013–0.020 mg/hr/kg satisfy the in vivo criteria and are embodiments of this invention. For the 6 hr SR duration with 5–75% IR, the $\Delta T_{ir+sr}$ was 6.4–7.2 hrs and exceeded the minimum requirement of 6.1 hrs. The corresponding in vivo sustained release rates were 0.004–0.014 mg/hr/kg. For the 8 hr SR duration with 5–62.5% IR, the $\Delta T_{ir+sr}$ was 6.7–8.1 hrs and exceeded the minimum requirement of 6.1 hrs. The corresponding in vivo sustained release rates were 0.004–0.010 mg/hr/kg. The $\Delta T_{ir+sr}$ simulated for a 10 hr SR duration with 5–40% IR was 6.7–6.8 hrs, which exceeded the $\Delta T_{ir}$=5.6 hr by 1.1–1.2 hrs. The corresponding zero order sustained release rates of 0.005–0.008 mg/hr/kg satisfy the in vivo $\Delta T$ criterion and are embodiments of this invention.

TABLE 14-2

Fraction of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations above 2 ng/ml for durations exceeding that for an equivalent dose of immediate release bolus by at least 30 minutes
(dose = 6 mg with $\Delta T_{ir}$ = 5.6 hr and $\Delta T_{ir+sr}$ > 6.1 hr; SR release rate 4, 6, 8, 10, and 12 hr).

| SR Duration (hrs) | Fraction of Dose as IR | Sustained Release Rate (mg/hr/kg) | $\Delta T_{ir+sr}$ C > $C_{min}$ (hrs) | $\Delta T_{ir+sr}$ > $\Delta T_{ir}$ + 0.5 |
|---|---|---|---|---|
| 4 | 0.05 | 0.020 | 6.3 | yes |
| 4 | 0.40 | 0.013 | 6.5 | yes |
| 4 | 0.75 | 0.005 | 6.0 | no |

TABLE 14-2-continued

Fraction of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations above 2 ng/ml for durations exceeding that for an equivalent dose of immediate release bolus by at least 30 minutes
(dose = 6 mg with $\Delta T_{ir}$ = 5.6 hr and $\Delta T_{ir+sr}$ > 6.1 hr; SR release rate 4, 6, 8, 10, and 12 hr).

| SR Duration (hrs) | Fraction of Dose as IR | Sustained Release Rate (mg/hr/kg) | $\Delta T_{ir+sr}$ C > $C_{min}$ (hrs) | $\Delta T_{ir+sr}$ > $\Delta T_{ir}$ + 0.5 |
|---|---|---|---|---|
| 6 | 0.05 | 0.014 | 6.4 | yes |
| 6 | 0.40 | 0.009 | 7.2 | yes |
| 6 | 0.75 | 0.004 | 6.5 | yes |
| 8 | 0.05 | 0.010 | 6.7 | yes |
| 8 | 0.25 | 0.008 | 8 | yes |
| 8 | 0.375 | 0.007 | 8.1 | yes |
| 8 | 0.50 | 0.005 | 7.7 | yes |
| 8 | 0.625 | 0.004 | 6.9 | yes |
| 8 | 0.75 | 0.003 | 6.1 | no |
| 10 | 0.05 | 0.008 | 6.8 | yes |
| 10 | 0.40 | 0.005 | 6.7 | yes |
| 10 | 0.75 | 0.002 | 5.5 | no |
| 12 | 0.05 | 0.007 | 5.2 | no |
| 12 | 0.40 | 0.004 | 4.7 | no |
| 12 | 0.75 | 0.002 | 5.5 | no |

Table 14-3 lists the $\Delta T_{ir+sr}$ values for simulations where a 12 mg dose was delivered as a hybrid IR/SR formulation. For the 12 mg dose, release rates of 4 to 18 hours were simulated and evaluated according to the above specified criteria (Table 14-3). The $\Delta T_{ir+sr}$ simulated for a 4 hr SR duration with 5–40% IR was 9.2–9.4 hrs, which exceeded the 8.8 hr requirement. The corresponding zero order sustained release rates of 0.026–0.041 mg/hr/kg satisfy the in vivo criteria and are embodiments of this invention. For the 6, 8, 12, and 16 hr SR duration with 5–75% IR, the $\Delta T_{ir+sr}$ values ranged from 9.2–16.2 hrs and are embodiments of this invention. The in vivo sustained release rates for the 6, 8, 12, and 16 hr SR duration with 75–5% IR were 0.027–0.007, 0.020–0.005, 0.014–0.004, 0.010–0.003 mg/hr/kg, respectively. For the 18 hr SR duration with 5–40% IR, the $\Delta T_{ir+sr}$ was 16.7–17.7 hrs and exceeded the minimum effective concentration. The corresponding in vivo sustained release rates were 0.009–0.006 mg/hr/kg.

TABLE 14-3

Fraction of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations above 2 ng/ml for durations exceeding that for an equivalent dose of immediate release bolus by at least 30 minutes
(dose = 12 mg with $\Delta T_{ir}$ = 8.3 hr and $\Delta T_{ir+sr}$ > 8.8 hr; SR release rate 4, 6, 8, 12, 16, and 18 hr).

| SR Duration (hrs) | Fraction of Dose as IR | Sustained Release Rate (mg/hr/kg) | $\Delta T_{ir+sr}$ C > $C_{min}$ (hrs) | $\Delta T_{ir+sr}$ > $\Delta T_{ir}$ + 0.5 |
|---|---|---|---|---|
| 4 | 0.05 | 0.041 | 9.4 | yes |
| 4 | 0.40 | 0.026 | 9.2 | yes |
| 4 | 0.75 | 0.011 | 8.7 | no |
| 6 | 0.05 | 0.027 | 10.3 | yes |
| 6 | 0.40 | 0.017 | 10.2 | yes |
| 6 | 0.75 | 0.007 | 9.2 | yes |
| 8 | 0.05 | 0.020 | 11.3 | yes |
| 8 | 0.25 | 0.016 | 11.5 | yes |
| 8 | 0.375 | 0.013 | 11.2 | yes |
| 8 | 0.50 | 0.011 | 10.8 | yes |
| 8 | 0.625 | 0.008 | 10.3 | yes |
| 8 | 0.75 | 0.005 | 9.8 | yes |
| 12 | 0.05 | 0.014 | 13.6 | yes |
| 12 | 0.40 | 0.009 | 13.5 | yes |
| 12 | 0.75 | 0.004 | 10.2 | yes |
| 16 | 0.05 | 0.010 | 15.7 | yes |
| 16 | 0.40 | 0.006 | 16.2 | yes |
| 16 | 0.75 | 0.003 | 9.2 | yes |
| 18 | 0.05 | 0.009 | 16.7 | yes |
| 18 | 0.40 | 0.006 | 17.7 | yes |
| 18 | 0.75 | 0.002 | 8.7 | no |

Table 14-4 lists the $\Delta T_{ir+sr}$ values for simulations where a 48 mg dose was delivered as a hybrid IR/SR formulation. The $\Delta T_{ir+sr}$ simulated for a 16 hr SR duration with 75–5% IR was 19.0–23.5 hrs, which exceeded the 13.9 hr requirement. The corresponding zero order sustained release rates of 0.011–0.041 mg/hr/kg satisfy the in vivo criteria and are embodiments of this invention.

TABLE 14-4

Fraction of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose delivered as immediate release from a IR/SR hybrid dosage form that results in plasma concentrations above 2 ng/ml for durations exceeding that for an equivalent dose of immediate release bolus by at least 30 minutes
(dose = 48 mg with $\Delta T_{ir}$ = 13.4 hr and $\Delta T_{ir+sr}$ > 13.9 hr; SR release rate 16 hrs).

| SR Duration (hrs) | Fraction of Dose as IR | Sustained Release Rate (mg/hr/kg) | $\Delta T_{ir+sr}$ C > $C_{min}$ (hrs) | $\Delta T_{ir+sr}$ > $\Delta T_{ir}$ + 0.5 |
|---|---|---|---|---|
| 16 | 0.05 | 0.041 | 23.5 | yes |
| 16 | 0.40 | 0.026 | 21.9 | yes |
| 16 | 0.75 | 0.011 | 19.0 | yes |

Exemplary immediate release percentages and sustained release durations of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from immediate plus sustained release dosage forms, based on these simulations, are dependent on dose, sustained release duration and % IR dose. For the about 6 mg dose, exemplary IR percentages and SR durations are about 5 to about 40% for about 4 hr SR, about 5 to about 75% for about 6 hr SR, about 5 to about 62.5% for the about 8 hr SR, and about 5 to about 40% for about 10 hr SR, respectively. For the about 12 mg dose, exemplary IR percentages and SR durations are about 5 to about 40% for about 4 hr SR, about 5 to about 75% for about 6, 8, 12, and 16 hr SR, and about 5 to about 40% for about 18 hr SR, respectively. For the about 48 mg dose, exemplary IR percentages for the about 16 hr SR duration is about 5 to about 75%.

Exemplary in vivo input rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate delivered from immediate plus sustained release dosage forms, based on these simulations, are dependent on dose, sustained release duration and % IR dose. For the about 6 mg dose, exemplary in vivo SR input rates are about 0.013 to about 0.020 mg/hr/kg for the about 4 hr SR duration, about 0.004 to about 0.014 mg/hr/kg for the about 6 hr SR duration, about 0.004 to about 0.010 mg/hr/kg for the about 8 hr SR duration, and about 0.005 to about 0.008 mg/hr/kg for the about 10 hr SR duration. For the about 12 mg dose, exemplary in vivo SR input rates are about 0.026 to about 0.041 mg/hr/kg for the about 4 hr SR duration, about 0.007 to about 0.027 mg/hr/kg for the about 6 hr SR duration, about 0.005 to about 0.020 mg/hr/kg for the about 8 hr SR duration, about 0.004 to about 0.014 mg/hr/kg for the about 12 hr SR duration, about 0.003 to about 0.010 mg/hr/kg for the about 16 hr SR duration, about 0.006 to about 0.009 mg/hr/kg for the about 18 hr SR duration. For the about 48 mg dose, exemplary in vivo SR input rates for the about 16 hr SR duration are about 0.011 to about 0.041 mg/hr/kg.

Exemplary zero order in vitro release rates of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxmethyl-2-oxo-ethyl]-isobutyramide L-tartrate delivered from sustained release dosage forms, are dependent on dose, sustained release duration and % IR dose. Exemplary SR rates for dosing a 70 kg human or other mammal are as follows. For the about 6 mg dose, exemplary SR rates are about 0.90 to about 1.42 mg/hr for the about 4 hr SR duration, about 0.25 to about 0.95 mg/hr for the about 6 hr SR duration, about 0.28 to about 0.71 mg/hr for the about 8 hr SR duration, and about 0.36 to about 0.57 mg/hr for the about 10 hr SR duration. For the about 12 mg dose, exemplary SR rates are about 1.80 to about 2.85 mg/hr for the about 4 hr SR duration, about 0.50 to about 1.9 mg/hr for the about 6 hr SR duration, about 0.38 to about 1.43 mg/hr for the about 8 hr SR duration, about 0.25 to about 0.95 mg/hr for the about 12 hr SR duration, about 0.19 to about 0.71 mg/hr for the about 16 hr SR duration, about 0.40 to about 0.63 mg/hr for the about 18 hr SR duration. For the about 48 mg dose, exemplary SR rates for the about 16 hr SR duration are about 0.75 to about 2.85 mg/hr.

Example 15

Immediate Plus Sustained Release Tablets

This example illustrates a process for making a combination immediate release plus sustained release product comprised of an active compound layer compression coated onto an osmotic 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate tablet. The processing of the osmotic sustained release tablet was previously described in Examples 7 and 9. The processing of the compression coating active compound layer comprised (1) blending of compression coating components as designated in Table 15-1, except for magnesium stearate; (2) adding and blending magnesium stearate; (3) placing half of the compression coating blend into the tablet press die, leveling, and centering the asymmetric membrane (AM) tablet on top of the powder layer, and adding the remaining half of the compression coating blend into the tablet press die; (4) compressing the powder active compound layer onto the asymmetric membrane (AM) coated tablets to form a composite tablet.

In batch sizes of 500 grams, 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate was blended in a suitable jar with all other components except magnesium stearate for 10 minutes using a Turbula shaker system (Willy A. Bachofen, Basel, Switzerland). Then, magnesium stearate was added and blended for 5 minutes. Using a conventional tablet press (Manesty F-Press, Manesty Machines, Liverpool, England), the final blend was compressed into tablets using 5/32 inch standard round concave (SRC) punches for the 350 mg compression coating layer weight. A summary of the compositions manufactured by compression coating of the formulation blend at 3 and 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate is shown in Examples 15A–15B, as detailed in Table 15-1. These combination immediate plus sustained release tablets contained a sustained release 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate AM tablet from Example 9C. The compression coating layers consisted of a 3 or 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate dose. The combination immediate plus sustained release tablets are embodiments of this invention.

TABLE 15-1

| Compression Coating Composition | | | | | |
|---|---|---|---|---|---|
| Example (No.) | Coating Wt (mg) | Active compound (mgA) | Content (wt %) | Avicel (wt %) | MgSt (wt %) |
| 15A | 350 | 3 | 1.1 | 97.9 | 1.0 |
| 15B | 350 | 10 | 3.8 | 95.2 | 1.0 |

Avicel ® means microcrystalline cellulose
MgSt means magnesium stearate

Example 16

In Vitro Performance of Immediate Plus Sustained Release Tablets

The immediate plus sustained release tablets from Example 15 were tested for active compound release performance using dissolution procedures described in Example 8 using 900 ml 0.1N HCl or SIN media. Additional samples were withdrawn at early time points to monitor the immediate release portion of the dissolution profile (i.e., 15, 30, 45, and 60 minutes). The results of the active compound release rate tests performed using those procedures are listed in Table 16-1.

TABLE 16-1

| Example Number- Media | Amount Of Active Compound Release (mgA) At Specified Time in Hours | | | | | | | | | | |
|---|---|---|---|---|---|---|---|---|---|---|---|
| | 0 | 0.25 | 0.50 | 0.75 | 1 | 2 | 4 | 8 | 12 | 16 | 24 |
| 9C - SIN | 0 | n.d. | n.d. | n.d. | 0.5 | 3.2 | 4.6 | 5.9 | 7.7 | 8.9 | 9.8 |
| 15A - SIN | 0 | 2.2 | 2.6 | 2.8 | 3.0 | 3.9 | 5.6 | 8.2 | 10.1 | 11.2 | 12.3 |
| 15B - SIN | 0 | 8.9 | 9.5 | 9.7 | 10.0 | 10.8 | 12.5 | 15.0 | 17.0 | 18.2 | 19.4 |
| 9C - HCl | 0 | n.d. | n.d. | n.d. | 0.5 | 1.4 | 3.3 | 6.1 | 8.0 | 9.0 | 9.6 |
| 15A - HCl | 0 | 2.6 | 2.8 | 3.0 | 3.1 | 4.0 | 5.8 | 8.5 | 10.4 | 11.5 | 12.4 |
| 15B - HCl | 0 | 9.1 | 9.9 | 10.2 | 10.4 | 11.5 | 13.4 | 16.1 | 17.9 | 18.9 | 19.7 |

9C consists of a 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate AM tablet without an immediate release active compound layer.
15A consists of a 3 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate active compound layer compression coated onto AM tablet #9C for a total dose of 13 mgA (23% IR).
15B consists of a 10 mg 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate active compound layer compression coated onto AM tablet #9C for a total dose of 20 mgA (50% IR).
SIN means simulated intestinal fluid without enzyme.
HCl means 0.1N HCl.

The sustained release in vitro boundaries corresponding to a 16 hr SR duration dosage form, exemplified by Example 9C, are 0.19–0.71 mg/hr for both $C_{max}$ and $\Delta T$ criteria for a total dose between 12–48 mg and 5–75% immediate release percentage.

Preferred immediate plus sustained release dosage forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate contain 5–75% dose delivered as immediate release from a 16 hr SR dosage form. Examples 15A and 15B demonstrate immediate plus sustained release of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate and are embodiments of this invention.

What is claimed is:

1. A sustained release dosage form for oral administration to a mammal, the dosage form comprising a growth hormone secretagogue and a pharmaceutically acceptable carrier, which dosage form results in a maximum growth hormone secretagogue plasma concentration, $C_{max}$, which is less than 80% of the $C_{max}$ that occurs when an equal dose of the growth hormone secretagogue is orally administered using an immediate release dosage form, wherein the dosage form is an osmotic tablet that comprises a core that is coated with an asymmetric membrane, the core comprising:

1) about 4 to about 10 mg of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl-]-isobutyramide L-tartate;
2) about 12 to about 50 wt % of the core of an acid selected from fumaric acid, tartaric acid, succinic acid, citric acid, L-aspartic acid, ascorbic acid, or combinations thereof;
3) about 20 to about 63 wt % of the core of an osmotic agent selected from mannitol, sorbitol, lactose, or combinations thereof;
4) about 22 to about 49 wt % of the core microcrysalline cellulose binder, and
5) about 0.5 to about 1.5 wt % of the core magnesium stearate, and the asymmetric membrane comprising cellulose acetate and polyethylene glycol which adds about 10 to about 18 wt % to the core for a core tablet having a weight of about 200 mg or less or about 8 to about 17 wt % to the core tablet for core tablets having a weight of about 300 mg.

2. A sustained release dosage form for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate to a mammal, the dosage form comprising:

| Component | Weight (mg/tablet) |
|---|---|
| 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate | about 3.89 |
| Mannitol | about 34.00 |
| Fumaric acid | about 12.00 |
| Microcrystalline cellulose | about 48.61 |
| Magnesium stearate | about 1.50 |
| Cellulose acetate | about 11.90 |
| Polyethylene glycol | about 5.10. |

3. A sustained release dosage form for oral administration of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxmethyl-2-oxo-ethyl]-isobutyramide L-tartrate to a mammal, the dosage form comprising:

| Component | Weight (mg/tablet) |
|---|---|
| 2-amino-N-[2-(3a-(R)-benzyl-2-methyl-3-oxo-2,3,3a,4,6,7-hexahydro-pyrazolo[4,3-c]pyridin-5- | about 12.97 |

-continued

| Component | Weight (mg/tablet) |
|---|---|
| yl)-1-(R)-benzyloxymethyl-2-oxo-ethyl]-isobutyramide L-tartrate | |
| Mannitol | about 113.32 |
| Fumaric acid | about 40.00 |
| Microcrystalline cellulose | about 162.01 |
| Magnesium stearate | about 5.00 |

-continued

| Component | Weight (mg/tablet) |
|---|---|
| Cellulose acetate | about 33.00 |
| Polyethylene glycol | about 22.00. |

* * * * *